United States Patent [19]
Roth

[11] Patent Number: 5,890,997
[45] Date of Patent: *Apr. 6, 1999

[54] COMPUTERIZED SYSTEM FOR THE DESIGN, EXECUTION, AND TRACKING OF EXERCISE PROGRAMS

[76] Inventor: Eric S. Roth, 2445 28th St. Suite #D, Santa Monica, Calif. 90405

[ * ] Notice: This patent issued on a continued prosecution application filed under 37 CFR 1.53(d), and is subject to the twenty year patent term provisions of 35 U.S.C. 154(a)(2).

[21] Appl. No.: 802,409

[22] Filed: Feb. 18, 1997

Related U.S. Application Data

[63] Continuation of Ser. No. 285,308, Aug. 3, 1994, abandoned.

[51] Int. Cl.$^6$ .................................................. A63B 71/00
[52] U.S. Cl. ............................. 482/8; 482/9; 482/902; 73/379.01; 601/23; 705/7
[58] Field of Search ........................... 434/247; 482/1–9, 482/900–902; 73/379.01; 340/323 R; 600/520; 601/1, 23; 705/7

[56] References Cited

U.S. PATENT DOCUMENTS

| | | | |
|---|---|---|---|
| 4,408,183 | 10/1983 | Wills | 340/323 R |
| 4,409,992 | 10/1983 | Sidorenko et al. | 482/901 |
| 4,493,485 | 1/1985 | Jones | 73/379.01 X |
| 4,493,488 | 1/1985 | Panaia et al. | 280/42 |
| 4,817,940 | 4/1989 | Shaw et al. | 482/9 |
| 4,828,257 | 5/1989 | Dyer et al. | 482/9 X |
| 4,911,427 | 3/1990 | Matsumoto et al. | 482/9 |
| 5,387,164 | 2/1995 | Brown, Jr. | 482/8 X |
| 5,410,472 | 4/1995 | Anderson | 482/9 X |

*Primary Examiner*—Joe H. Cheng
*Attorney, Agent, or Firm*—Matthew F. Jodziewicz

[57] ABSTRACT

A computerized system and method for the design, execution and tracking of exercise programs including portable microprocessor controlled data controllers to instruct and record the actual computed workout for the user. A data communication link transfers data between the data controllers and a computer hosting application software and database files for the particular user, exercise and exercise regimen to create and display a customizable and comprehensive exercise system designed for the particular user.

23 Claims, 35 Drawing Sheets

FIG. 27

COMPUTERIZED SYSTEM FOR THE DESIGN, EXECUTION, AND TRACKING OF EXERCISE PROGRAMS

This is a continuation of application Ser. No. 08/285,308 filed on Aug. 9, 1994, now abandoned.

NOTICE REGARDING COPYRIGHTED MATERIAL

A portion of the disclosure of this patent document contains materials which are subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF THE INVENTION

The invention relates to a computerized exercise fitness program designing system and method for assisting in execution and recording of performance information.

BACKGROUND OF THE INVENTION

A consistent fitness regiment is universally accepted by medical authorities as being instrumental to longevity and good health. There are currently several devices available that monitor an individual exercising on an exercise apparatus. Examples of these are U.S. Pat. Nos. 4,493,485, 4,409,992, and 4,408,183. The problem with these devices is that they are limited to recording the performance the user decides to achieve and provide no instruction on the performance the user should achieve. For example, U.S. Pat. No. 4,493,488 provides a predetermined pace for the user regardless of the user's actual fitness level. Additionally, the aforementioned devices provide no indication of past performance from which a trend can be interpolated. U.S. Pat. No. 4,817,940 does provide the capability to record past performance but makes no provision to automatically calculate future performance requirements based upon that stored information. Additionally U.S. Pat. No. 4,817,940 requires that each piece of exercise equipment be instrumented in order to be accessible by the device.

A key element to a fitness program is the ability to continually challenge the body physically. When a person has performed an exercise at a consistent level, the muscles tend to acclimate to the particular exercise and plateau at the level of development required to maintain the exertion level. In order to advance the development of the muscles involved, the exertion level must be increased at specific intervals. Without continual professional instruction, most amateur fitness enthusiasts lack the basic knowledge to determine when and by how much to advance their workout parameters to achieve maximum effectiveness.

The System described herein allows the Trainer to impart a training philosophy to each exercise. The Trainer can specify up to four actions to be performed, automatically, on specified exercise dependent parameters (pounds of weight, repetitions, sets, etc.) when specified events (completed routines, elapsed days, etc.) occur. The Trainer can have a parameter increase, decrease, or the exercise completely removed from the workout when the specified event occurs. The events are user selectable using dynamically compiled lists and numeric entry fields. Each time client's daily workout routine is requested, the System will compute the new parameters for each exercise using the exercise's philosophy settings, the performance of the last workout session, and the current date. The end result is a workout program that adapts to the client's actual workout performance achieving the desired result without the client possessing a prerequisite knowledge of exercise training or cost of a private trainer each workout session.

The current most popular method of displaying and recording an exercise fitness program involves a cardboard sheet depicting a list of exercises, initial setup parameters, and columns representing workout sessions. The user must manually mark the repetitions, sets, or other work performed for each corresponding exercise. The end result is a very crowded matrix that reveals little trend information and requires manual computation to determine future performance goals. Storage of these sheets may become cumbersome, especially for a large client population.

The System will eliminate the paper workout sheet and replace it with compact portable battery powered computerized Digital Training Assistants (DTAs). Each DTA is dynamically programmed with the user's own fitness routine calculated for the specific workout session. The DTA unit will interactively instruct the user on both the sequence of exercises to be performed as well as the exercises setup and desired performance parameters. A keypad interface to modify parameters is provided to permit recording of the actual work performed. The resultant exercise information is downloaded back to the System where it becomes a permanent part of the user's individual workout performance history database file. The file's data will be used in the computation of the next workout session's exercise performance parameters.

Determining past performance trends using the traditional paper method of parameter recording requires manually graphing data points. This becomes increasingly impractical with increasing number of workouts. The user will often not increase the workout parameters over time or even worse, increment parameters regardless of the actual fitness level attained.

By utilizing the detailed exercise data in the client's individual workout performance history database file, several reports and graphs can be produced with the speed and accuracy of a computerized system. This gives a new level of instant feedback not previously available in the Fitness Club environment. The client is now able to determine the apparent effectiveness of his workout routine and become more connected to his workout by virtue of the near real-time reporting capability of the System. Enthusiasm and involvement are both enhanced.

A common problem with personal trainers at a fitness club is that each trainer will impart their own individual exercise fitness philosophy onto a client. The result being that any two clients trained by different trainers will have differing fitness programs and varied results. There is a loss of standardization within the club and each new trainer adds to the problem. A method of standardizing the training philosophies using a collective expertise is needed within the industry.

The proposed system will allow the Head Trainer to impart his/her training expertise to each Assistant Trainer by mandating that the trainers implement one of the stored exercise routine templates when training a client. The System will allow different exercise templates to be constructed using the equipment and exercises found at the facility. Each template's exercises may have corresponding parameter increasing/decreasing philosophies designed by the Head Trainer as well.

Accuracy in reporting a client's workout performance is another problem encountered by trainers. When a client is not being monitored personally by a trainer, the client is then responsible for remembering and recording the actual work performed. The client must also be aware of the parameters to record and the correct terminology. The Trainer must then be apprised of the client's performance so that he/she may make adjustments as required.

The DTA units allow the client to easily record the actual work performed. Even if a client is unable to complete the exercise as prescribed and displayed, the actual work performed is easily input to the DTA using a numeric keypad and associated function keys. The DTA will prompt the client to make the entry and alert him of any input errors with the required corrective action. The edited workout routine is then downloaded, with computer accuracy, to the System. The changes are instantly noted by the System and adjustments are automatically made.

Currently, at a moderate sized fitness club, the client to trainer ratio is worse than 40 to 1. Most client's are reluctant to incur the additional cost of a Personal Trainer at each session as well as the inconvenience of having to schedule workouts around a trainer's availability. The result is a vast majority of a club's clientele are not taking advantage of the trainers. A potential loss of revenue for the club.

When utilizing the System, the trainers effectively multiply their presence and utility. This is accomplished by having many clients operating the System and DTAs, following the trainer's designed workout program. The automatic parameter philosophy incrementing/decrementing function will ensure that the client is receiving the maximum benefit of the exercise program as if the trainer were always present to make those adjustments in person. An initial trainer/client session for setup and instruction on usage will increase facility's trainer exposure and periodic fitness program checkups ensure further trainer usage.

Currently, a trainer would have to interview and review the workout sheets for several clients to determine if a particular training regiment is performing as prescribed. This is a labor intensive endeavor demanding a large portion of the trainer's work hours. It is to both the trainer's and client's benefit to maximize the effectiveness of a workout routine.

The system will allow the trainer to asses the effectiveness of a workout program by virtue of the system's recording and reporting capabilities combined with the ability to simultaneously look at several different client's and their corresponding demographics. Performance graphs give easily understandable trend analysis useful in determining the effectiveness of the regiment. The trainer may now fine tune the routine to achieve maximum effectiveness.

The comprehensive database capabilities of the system will allow the creation of equipment usage reports charting the number of clients using a particular piece of exercise equipment during a particular week throughout a calendar year this will provide more accurate maintenance scheduling and equipment utilization data.

Demographic and medical information for a client is instantly available to the Trainer as well as the ability to create reports for membership analysis. Such information is very useful in planning promotions and configuration of the facility to better match the client's requirements.

SUMMARY OF THE INVENTION

The System is composed of both a computer software application program and custom computer hardware. The application software, as it currently exists, operates under the Microsoft® Windows™ 3.1 (or above) personal computer operating system. The software constructs and utilizes a variety of Xbase™ type database files to store and retrieve information about clients, Trainers, facility configuration, system preferences, and client workout routines. Computational capabilities include processing exercise workout parameters to produce a dynamic daily workout regiment. Graphical objects are used to implicitly guide the user in operation of the software's embedded functions.

The application software will produce, as one of its prime functions, a workout routine consisting of exercise names and their associated setup and parametirc data. The routine is interactively constructed for a specified client. The routine can then be formatted and electrically transferred to a Digital Training Assistant (DTA). The DTAs utilize a 16-alphanumeric character display and keypad to instruct the user on execution of the workout stored within. The DTAs also allow the various exercise parameters to be modified as needed. Ancillary functions include a stopwatch timer, interactive pulse recording function, and body weight input facility.

The executed exercise routine is eventually transferred from the DTA back to the System where it is reincorporated into the client's database files. The exercise routine is uploaded and downloaded to a DTA by insertion into a special DTA Programming Stand. The DTA Programming Stand is connected to the host computer via an RS-232C interface and converts the electrical signal levels to those compatible with the DTA's own serial interface. Commands from the host computer to the DTA will initiate either the upload or download action. Indicators on the Programming Stand will display power and programming status. Several DTA units may be used with a single DTA Programming Stand all under control of a single software system

BRIEF DESCRIPTION OF THE DRAWINGS

Those and other objects and advantages of the present invention will become more apparent by referring to the following detailed description and accompanying drawings in which:

FIG. 27 Client Information Screen representation.

DESCRIPTION OF AN ILLUSTRATIVE EMBODIMENT

Figure 1:
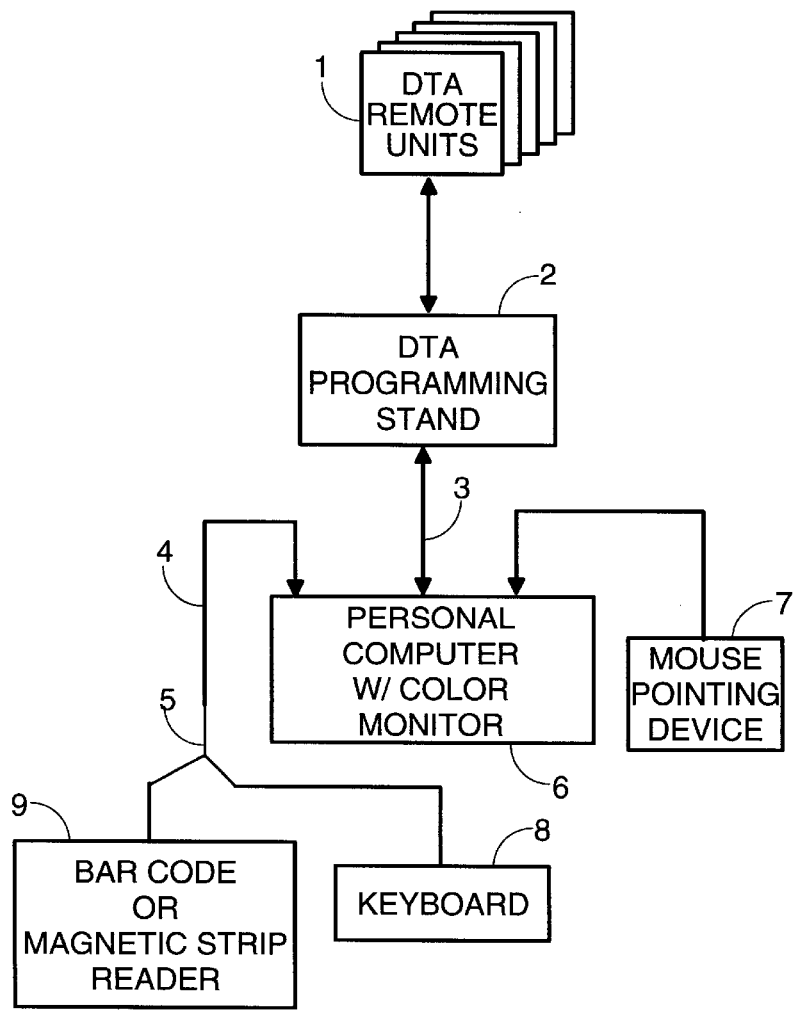
FIG. 1 Shows a basic diagram of the principal components of the computerized exercise fitness program design, execution, and recording system.

A. General Description of the exercise fitness program design, execution, and recording system Referring to the drawings;

FIG. 1 Shows a basic diagram of the principal components of the computerized exercise fitness program design, execution, and recording system.

Central to the system is a the Personal Computer (PC) 6 that is capable of running Microsoft® Windows™ 3.1 (or above) operating system. The minimum system requirements to run Windows™ also applies to the System's application software. The Keyboard 8 is connected to a 'Y' adapter 5 that also connects the Bar Code or Magnetic Strip reader 9 to the Personal Computer 6.

The DTA Programming Stand 2 is connected to the PC 6 using an RS-232C serial link cable 3. The cable 3 can connect to any COM port on the PC 6. The DTA units 1 are connected to the system by placement into the DTA Programming Stand 2 whereby complimentary electrical contacts from both are engaged.

A mouse pointing device 7 is highly recommended but not essential to the operation of the system application software.

B. Detail Description of the exercise fitness program design, execution, and recording system components NOTE: It should be noted that there exists two versions of both the Digital Training Assistant units and DTA Programming Stands. Differences will be pointed out where indicated and/or necessary. The System's application software is compatible with both units.

Figure 2:
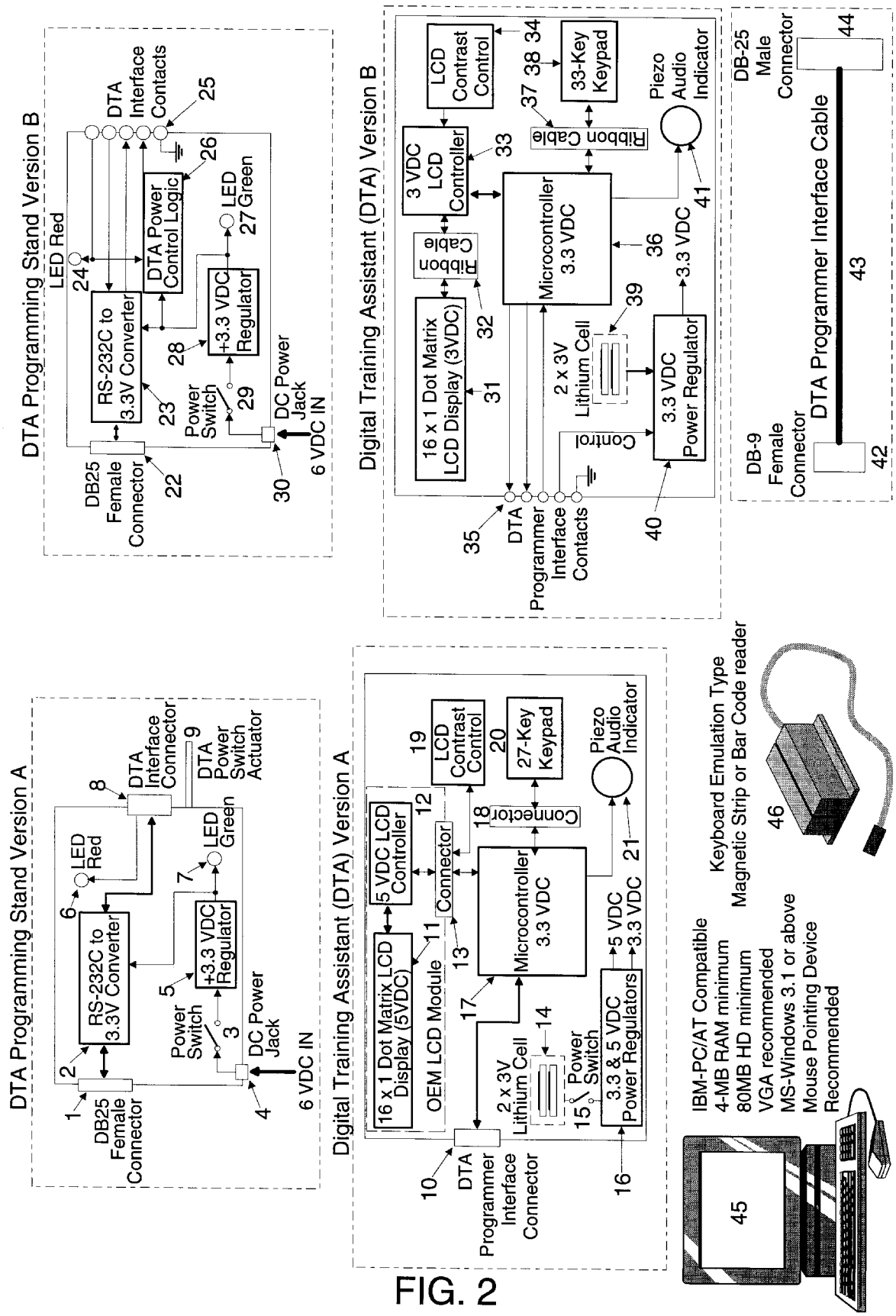
FIG. 2 Shows block diagrams of all versions of the components that constitute the invention.

Referring to the drawings;

FIG. 2 Shows block diagrams (both versions) of the components that constitute the invention.

The Version-A DTA Programming Stand interfaces to the host PC via connection to the RS-232C serial link cable through the DB-25 female connector 1. The signals are then translated to the 3.3 V logic levels required by the DTA units using the EIA/TIA-562 transceiver 2. Power is supplied by any external regulated power supply capable of delivering 6 VDC@ 400 mA minimum. The power supply must be able to mate with the DC power jack 4. A SPST switch 3 is used to apply power to Programming Stand. The +6 VDC is routed to a 3.3 V regulator 5 that outputs a steady +3.3 VDC to the remaining circuitry. A green LED 7 will indicate the presence of power to the DTA Programming Stand's internal circuitry. The Version-A DTA interfaces to the Version-A DTA Programming Stand by connecting with DTA Interface Connector 8. Serial data transmission lines are connected directly to the EIA/TIA-562 transceiver 2. A red LED 6 connects to a dedicated signal line from the DTA to indicate programming status. The DTA Power Switch Actuator 9 inserts into a hole on the side of the Version-A DTA to activate the DTA's power switch.

The Version-A Digital Training Assistant interfaces to the Version-A DTA Programming Stand via connection with DTA Programmer Interface Connector 10. The serial and control signals are routed directly to the 8-Bit microcontroller 17. Power to the DTA unit is supplied by a pair of CR2025 3 V lithium coin cells 14. A SPST push-on, push-off switch 15 routes power to the dual power regulators 16. The +3.3 & +5 VDC regulators 16 supply power to the remaining DTA circuitry. The 8-Bit microcontroller 17 interfaces through connector 13 to an OEM LCD Character module 11 & 12. The OEM LCD Module consists of a +5 VDC LCD Controller 12 and the actual LCD glass 11. Display contrast is controlled by potentiometer 19. A 27-Key Keypad 20 connects to the 8-Bit Microcontroller 17 via a pair of connectors 18. A Piezo Audio Indicator 21 is connected directly to the 8-Bit Microcontroller 17.

The Version-B DTA Programming Stand interfaces to the host PC via connection to the RS-232C serial link cable through the DB-25 female connector 22. The signals are then translated to the 3.3 V levels required by the DTA units using the EIA/TIA-562 transceiver 23. Power is supplied by any external regulated power supply capable of delivering 6 VDC@ 400 mA minimum. The power supply must be able to mate with the DC power jack 30. A SPST switch 29 is used to apply power to Programming Stand. The +6 VDC is routed to a 3.3 V regulator 28 that outputs a steady +3.3

VDC to the remaining circuitry. A green LED 27 will indicate the presence of power to the DTA Programming Stand's internal circuitry. The Version-B DTA interfaces to the Version-B DTA Programming Stand by connecting with DTA Interface Contacts 25. Serial data transmission lines are connected directly to the EIA/TIA-562 transceiver 23. A red LED 24 connects to a dedicated signal line from the DTA to indicate programming status.

The Version-B Digital Training Assistant interfaces to the Version-B DTA Programming Stand via direct contact with DTA Programmer Interface Contacts 35. The serial and control signals are routed directly to the 8-Bit microcontroller 36. Power to the DTA unit is supplied by a pair of CR2025 3 V lithium coin cells 39. A dedicated control signal from the DTA Programming Stand via the DTA Programmer Interface Contacts 35 is used to activate the +3.3 VDC regulator 40. The +3.3 VDC regulator 40 supplies power to the remaining DTA circuitry. The 8-Bit microcontroller 36 interfaces directly to the T7934 LCD Controller 33. A ribbon cable 32 connects the row and column drivers to the custom designed +3 VDC 16–5×8 dot matrix character LCD glass 31. Display contrast is controlled by potentiometer 34. A 33-Key Keypad 38 connects to the 8-Bit Microcontroller 36 via a ribbon cable 37. A Piezo Audio Indicator 41 is connected directly to the 8-Bit Microcontroller 36.

An OEM serial interface cable is used to connect the DTA Programming Stand with the host PC. The cable is composed of a DB-9 female connector 42, 8 feet of 9 conductor 24-AWG 7×32 STRAND PVC 300 V 80° C. Aluminum Poly Shield cable 43, and a DB-25 female connector 44.

Although expressly outside the scope of this document, the host Personal Computer 45 and keyboard emulation type Magnetic Strip or Bar Code reader 46 are included in FIG. 2 for clarity.

C. System Component Mechanical Form

Figure 3:
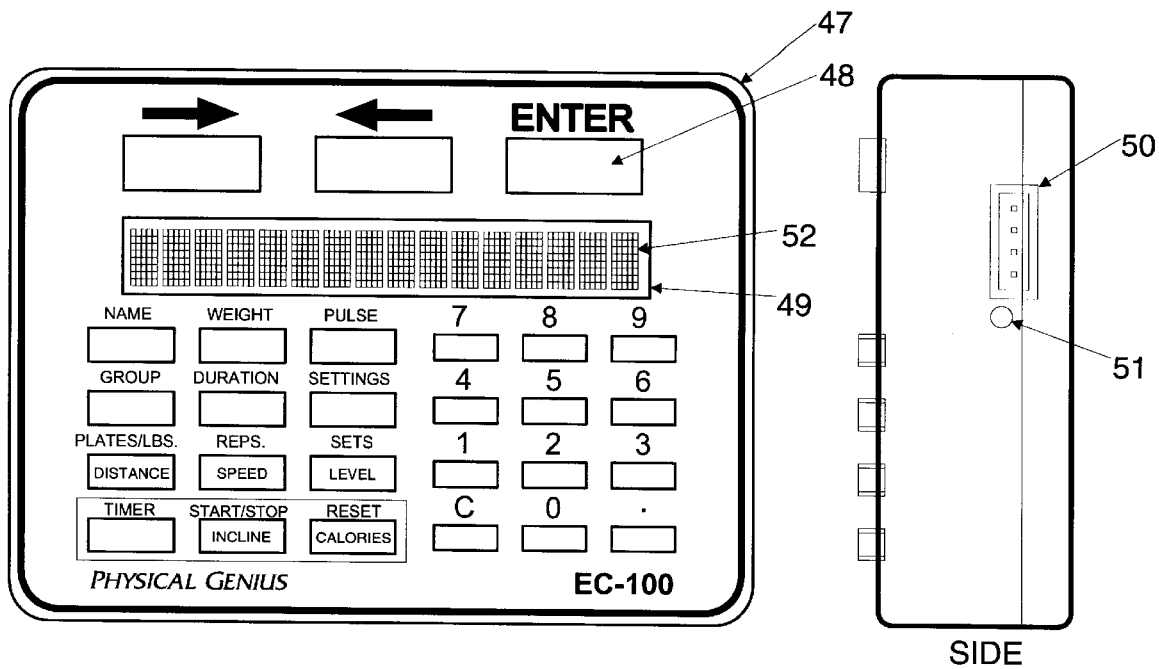
FIG. 3 Shows a depiction of the Version-A Digital Training Assistant unit.

Referring to the drawings:

FIG. 3 Shows a depiction of the Version-A Digital Training Assistant unit.

The ABS plastic case 47 houses the electronic components within. An elastomer keypad 48 is accessed through cutouts in the upper case component. A clear plastic window 49 is used to view the 16-Character LCD dot matrix display 52. The DTA Programming Stand Interface Connector 50 is visible on the right side view. The power switch actuation hole 51 is also visible next to the connector 50.

Figure 4:
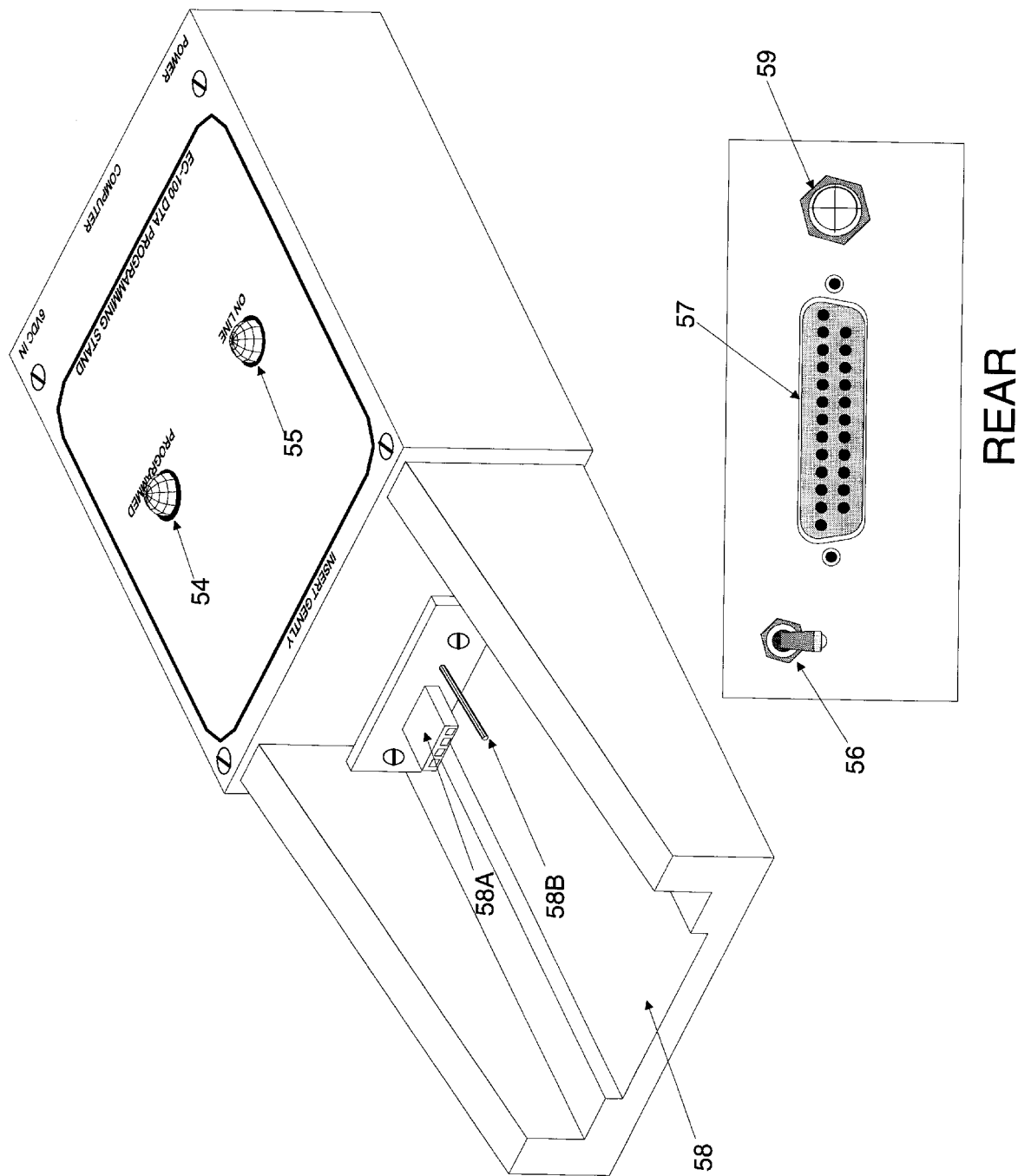
FIG. 4 Shows a depiction of the Version-A DTA Programming Stand.

FIG. 4 Shows a depiction of the Version-A DTA Programming Stand.

The ABS plastic case 53 houses the electronic components within. A red LED 54 indicates the status of DTA programming and the green LED 55 indicates the presence of power to the DTA Programming Stand. The DTA is inserted into slot 58 where is connects to the DTA Interface Connector 58A. The DTA Power Switch Actuator 58B inserts through the corresponding hole in the side of the DTA unit to activate the internal power switch. The Power Switch 56 is located on the rear panel. The host PC interface DB-25 male connector 57 and DC Power Jack 59 are also located on the rear panel.

Figure 5:
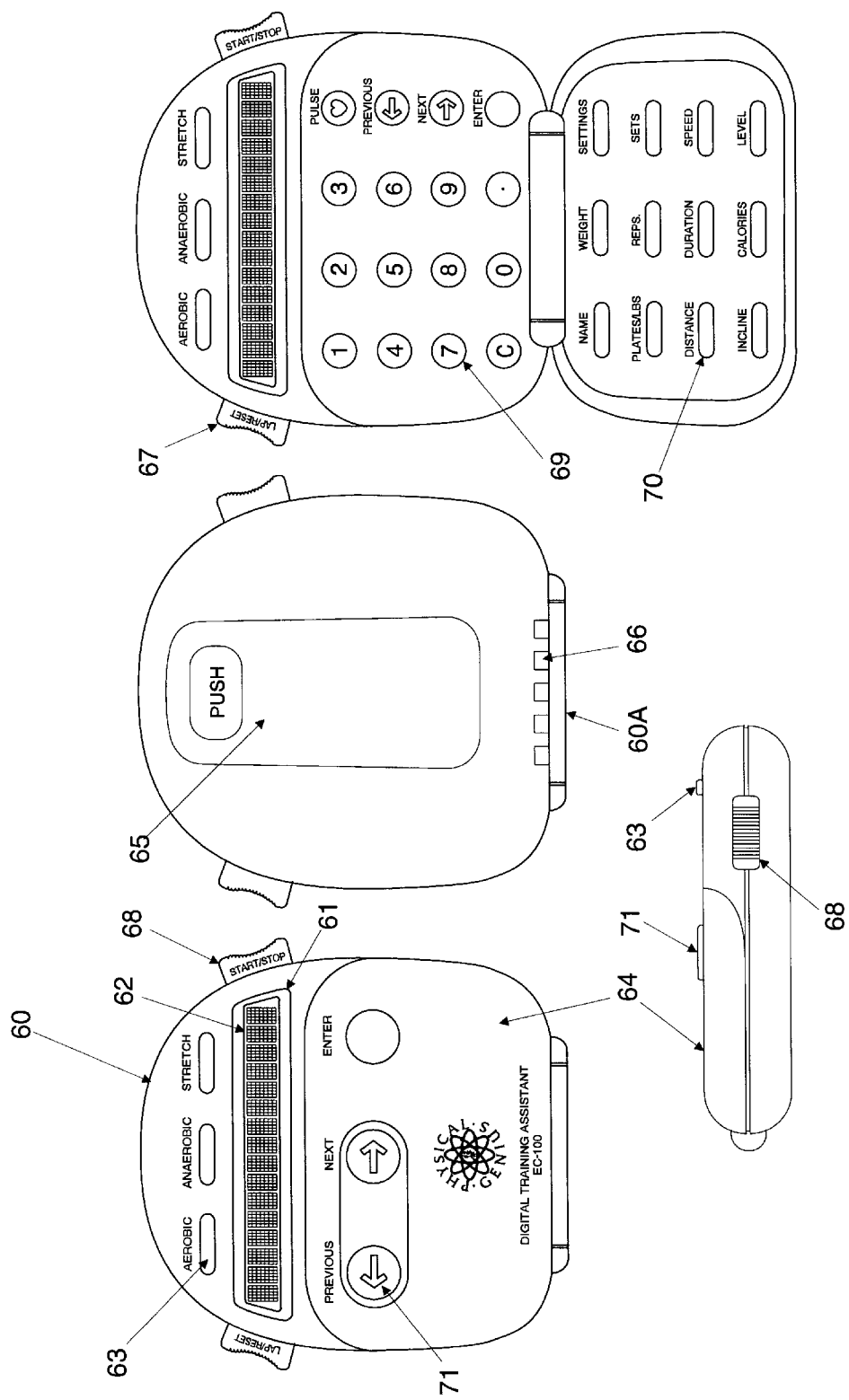
FIG. 5 Shows a depiction of the Version-B Digital Training Assistant unit.

FIG. 5 Shows a depiction of the Version-B Digital Training Assistant unit.

The ABS plastic case 60 houses the electronic components within. Elastomer keypads 63, 71, 69 & 70 are accessed through cutouts in the case components. The stopwatch control buttons 67 & 68 are separate mechanical switches located on opposing sides of the unit. A clear plastic window 61 is used to view the 16-Character LCD dot matrix display 62. The flip-open cover 64 reveals the numeric keypad 69 and Function Keypad 70 An integrated Flush Mounted Self-Adjusting Clip 65 is located on the rear of the DTA unit. The DTA Interface Contacts 66 are clearly visible above the cover hinge 60A.

Figure 6:
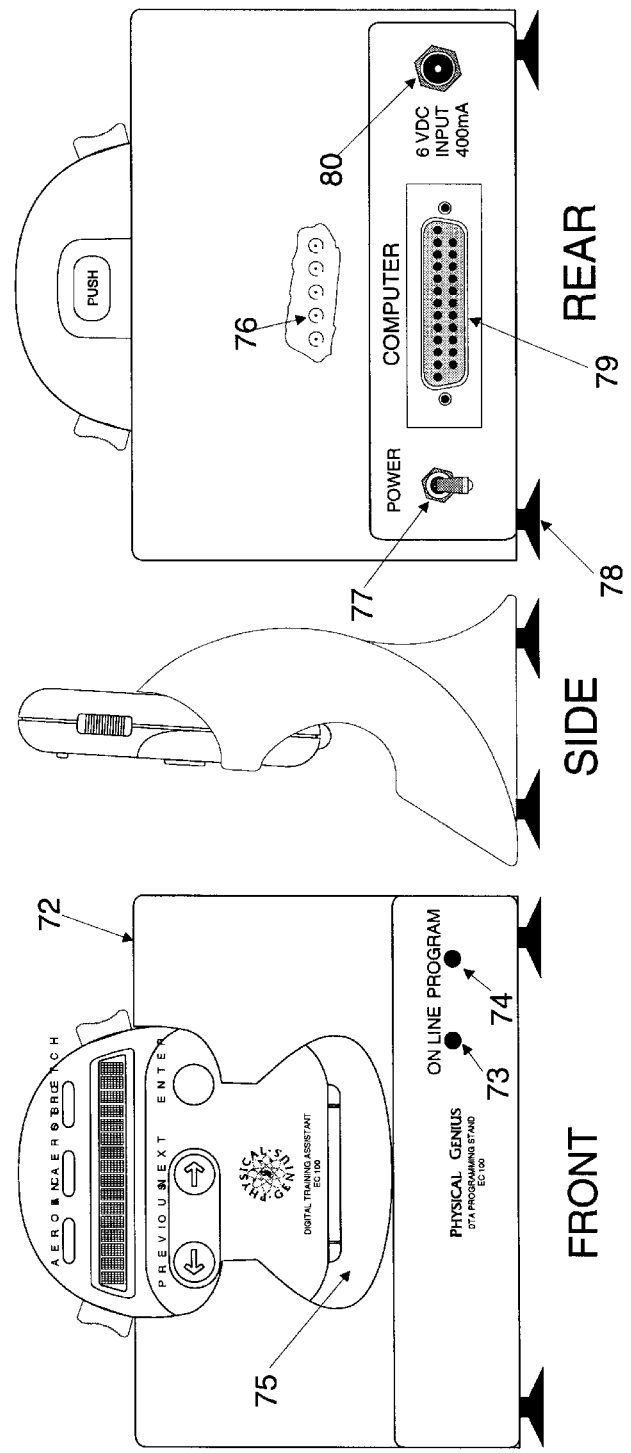
FIG. 6 Shows a depiction of the Version-B DTA Programming Stand.

FIG. 6 Shows a depiction of the Version-B DTA Programming Stand.

The ABS plastic case 72 houses the electronic components within. A red LED 74 indicates the status of DTA programming and the green LED 73 indicates the presence of power to the DTA Programming Stand. The DTA is placed into form fitting depression 75 where it contacts the DTA Interface Contacts 76. The Power Switch 77 is located on the top of the Programming Stand and is of the push-on, push off type. The host PC interface DB-25 female connector 79 and DC Power Jack 80 are also located on the front panel. Suction cups 78 are provided for secure installation on a smooth flat surface.

Figure 21:
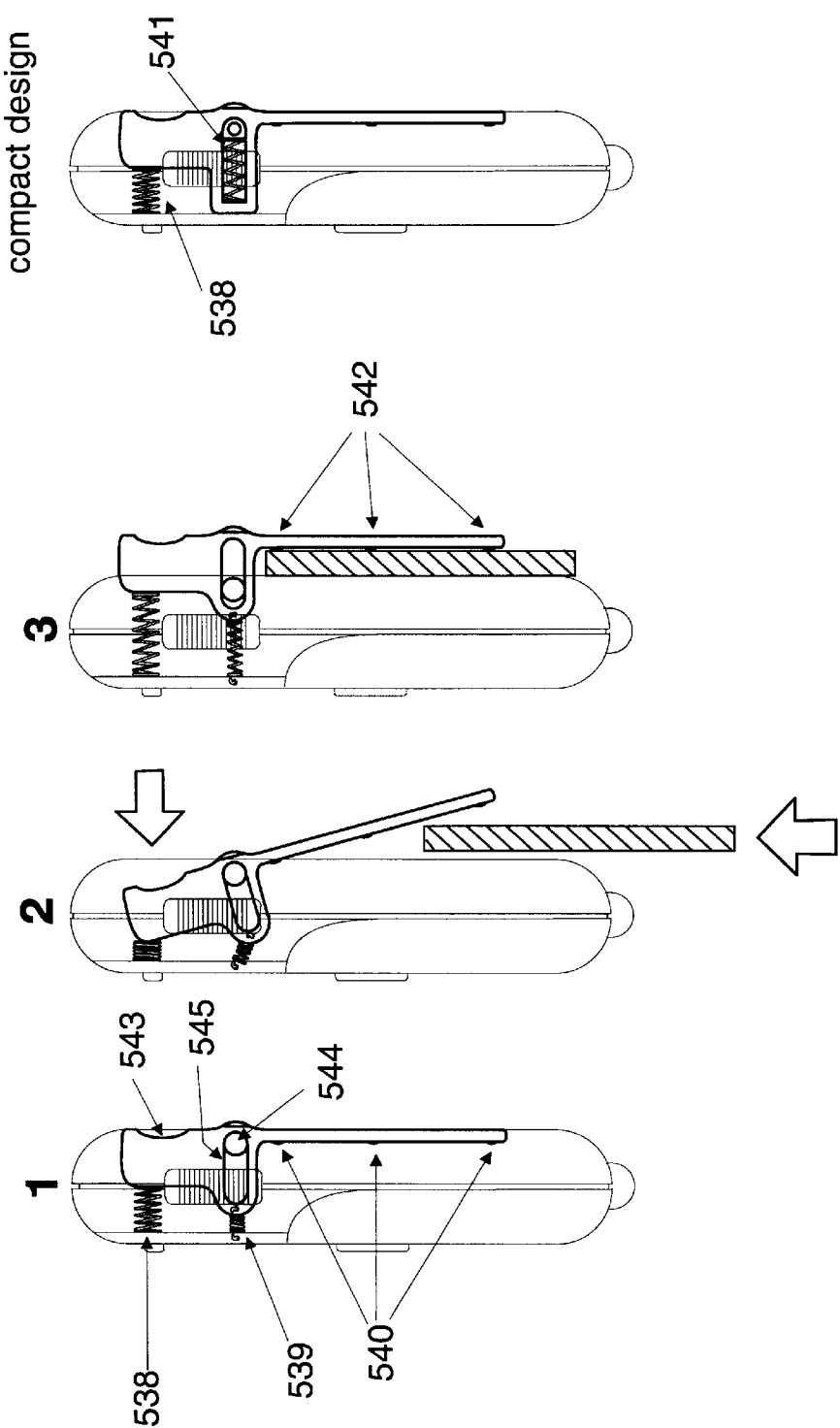

FIG. 21 Shows a detail of the Flush Mounted Self Adjusting Clip on the Version-B DTA units.

In Detail 1 of the figure, the force of the compression spring 538 is exceeded by the force of the expansion spring 539 holding the clip in the stowed position. When pressure is applied to the activation depression 543, as shown in Detail 2, the compression spring 538 is compressed further and the clip pivots on the pivot pin 544. A ¼" maximum thick surface can now be inserted between the clip and the DTA back surface. When the pressure to the activation depression 543 is released, as sown in Detail 3, The expansion spring 539 is stretched, the clip moves along the pivot slot 545 and the compression spring 538 is allowed to decompress further bringing the clip parallel with the inserted surface. The grip points 542 are now in even contact with the surface providing positive grip. To release the surface, pressure is again applied to the activation depression 543 and the surface is removed.

An alternative design is to replace the expansion spring 539 with a second compression spring 541 located inside the pivot slot 545. The effect is the same but the design is more compact.

D. System Component Electrical Description

Figure 7:
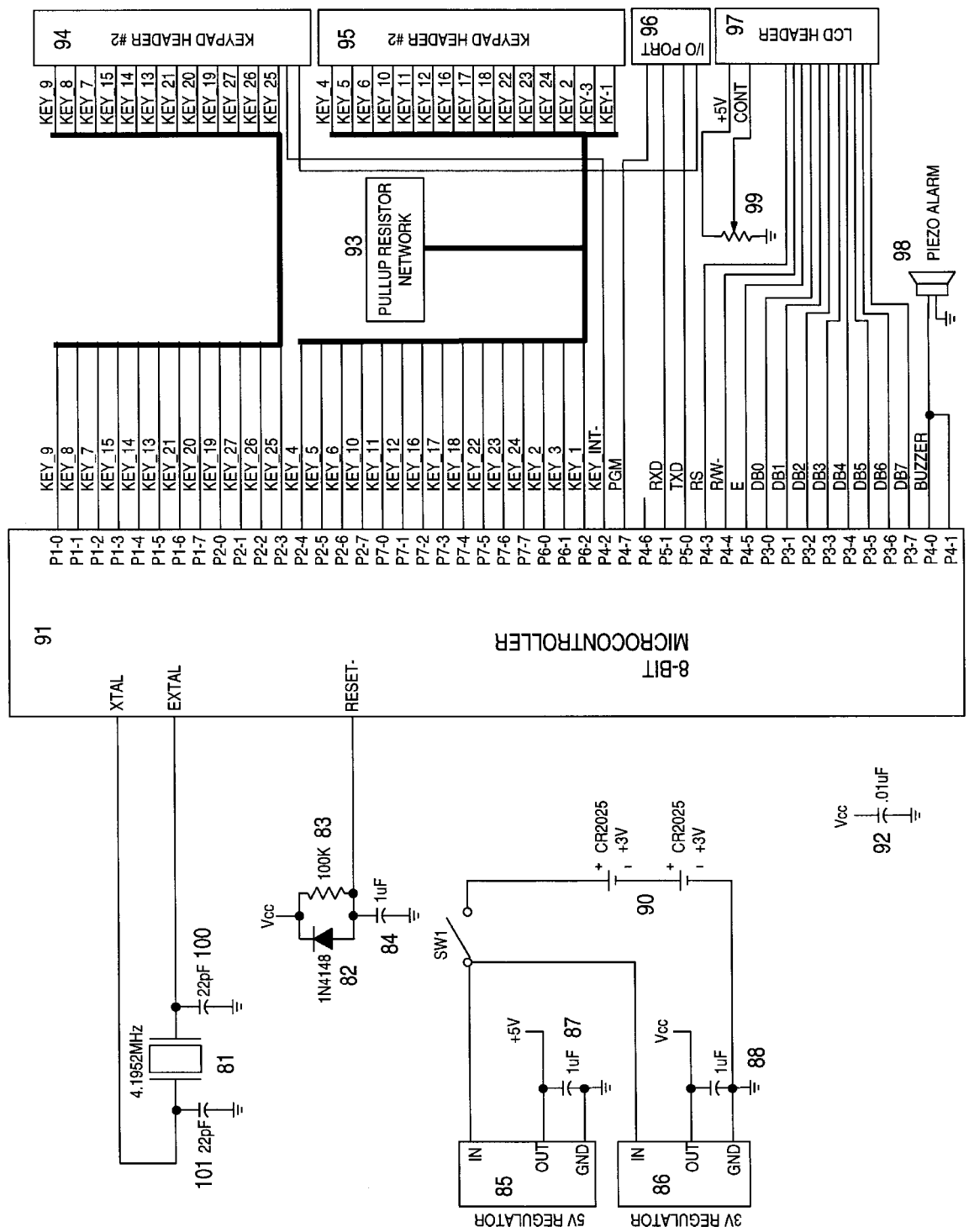
FIG. 7 Shows a detailed circuit diagram of the Version-A Digital Training Assistant unit.

Referring to the drawings:

FIG. 7 Shows a detailed circuit diagram of the Version-A Digital Training Assistant unit.

Power is activated by closing SPST switch 89. The two CR2025 Lithium Coin Cell Batteries 90 supply +6 VDC to the +5 VDC regulator (LT1121CZ-5) 85 and +3.3 VDC regulator (LT1121CZ-3.3) 86. Each regulator has a single 1.0 uF filter capacitor 87 & 88.

The Resistor-Capacitor power-on reset circuit constructed with a diode 82, 100K resistor 83, and 1 uF capacitor 84 combine to give an RC constant of 100 mS. The reset signal is sent to the reset input of the 8-Bit Microcontroller 91.

The 8-bit microcontroller 91 is a Hitachi H8/329 Series single-chip microcomputer (microcontroller). The microcontroller contains 32 Kbytes of Read Only Memory (ROM), 1 Kbyte of Random Access Memory (RAM), one 16-bit free running timer, dual 8-bit timers, a serial communications interface, an A/D converter, and extensive bit controllable I/O ports. The microcontroller 91 operates at +3.3 VDC and utilizes a 4.9152 MHz AT-cut parallel resonating crystal 81 with associated 22 pF capacitors 100 & 101. A single 0.01 uF decoupling capacitor 92 is provided for the microcontroller 91.

The microcontroller's 91 P1, P2, and P7 I/O ports are used to receive keypad key press signals via the 15-pin keypad header connectors 94 & 95. An interrupt signal from the keypad is generated for each key pressed and received by the microcontroller 91 through the INT0 input (P4-2). Pull-up resistors for those ports not equipped with built-in pull-ups is provided by 27K resistor network 93.

The microcontroller 91 has a built-in asynchronous serial communications port. The receive and transmit data signals are connected to the DTA Programming Stand Interface Connector 96. A signal ground is provided to match grounds between DTA and Programming Stand. A program status signal originates from a microcontroller 91 P4-7 port pin to the DTA Programming Stand Interface Connector 96.

The prerequisite 8-bit data interface to the OEM LCD Display Module is created by using the microcontroller's 91 P3 and P4 I/O ports. The signals are routed directly to the 14-pin LCD header connector 97. The contrast control signal from the OEM LCD Display Module is available through the header connector 97 and is connected to a 2K potentiometer 99. The +5 V supply to the OEM LCD Display module is provided through the header connector 97 as well.

A piezo type audio indicator 98 capable of being driven by a +3.3 V square wave is connected directly to the microcontroller's 91 P4-0 and P4-1 I/O pins (tied together for more drive) to provide audio alarms queues.

Figure 8:
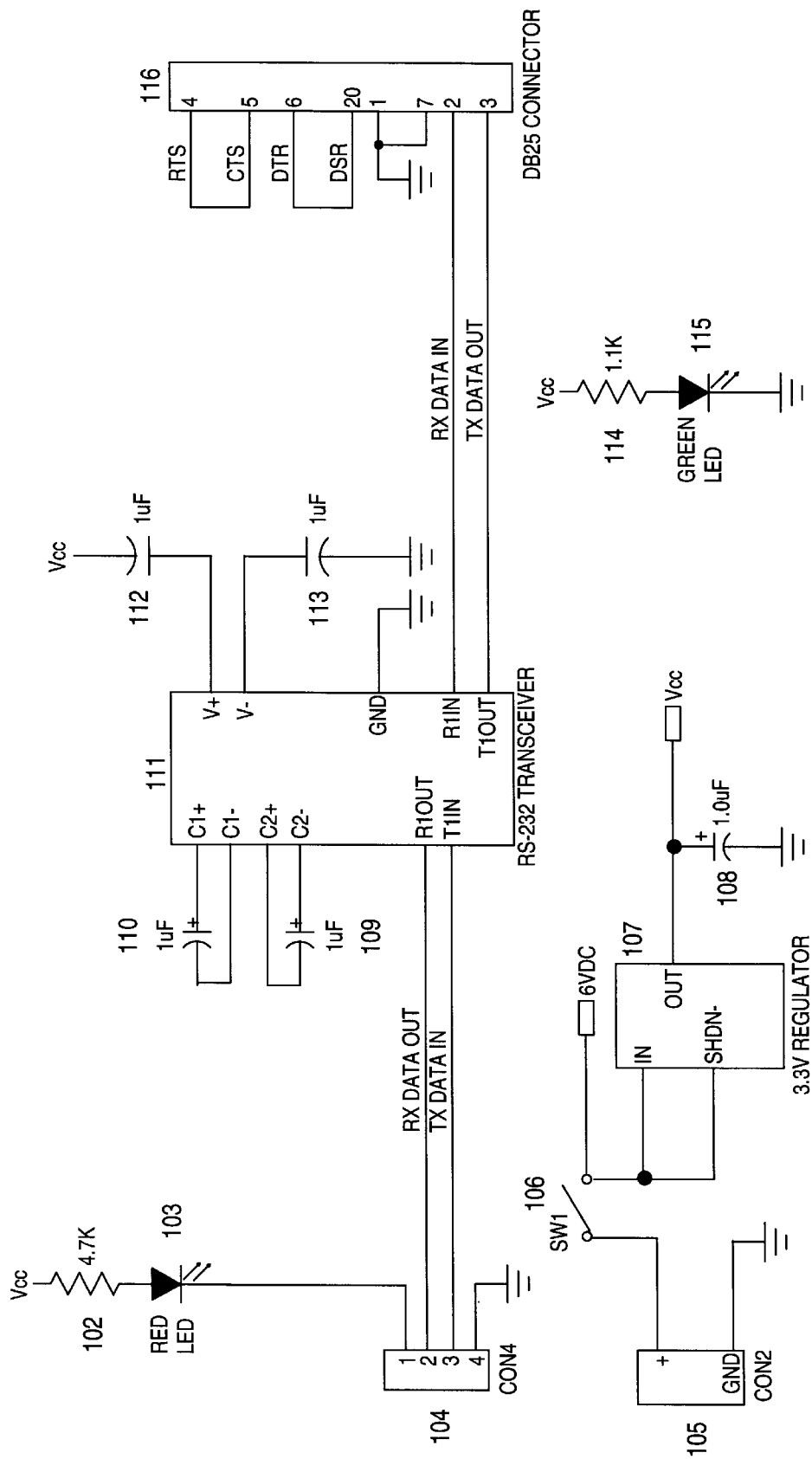
FIG. 8 Shows a detailed circuit diagram of the Version-A DTA Programming Stand.

FIG. 8 Shows a detailed circuit diagram of the Version-A DTA Programming Stand.

Power to the DTA Programming Stand is supplied by an external AC to DC regulated power supply producing +6 VDC at 400 mA minimum to the DC Power Jack 105. The power switch 106 routes power to the LT1121CN8-3.3 voltage regulator 107 which supplies +3.3 VDC to the remaining circuitry, A single output 1uF filter capacitor 108 is used. A green LED 115 and associated current limiting resistor 114 indicate the presence of power to the DTA Programming Stand.

The serial data interface to the host PC is provided using the DB-25 female connector 116. Appropriate control signals are tied together or ground to facilitate asynchronous communication. Transmit and receive data lines are routed to the MAX561CWI +3.3 V Transceiver w/Two EIA/TIA-562 Receivers 111. The RS-232C signal levels from the host PC are converted to the +3.3 V logical levels for the DTA units and vice versa. Charge-pump 1 uF capacitors 109, 110, 112, & 113 completed the transceiver/converter design.

The DTA interface connector 104 routes serial data transmit and receive signals to the transceiver/converter 111 directly. A common signal ground is provided to equalize voltage levels between the DTA and Programming Stand. A red LED 103 and associated current limiting resistor 102 are used to indicate programming status using a signal from the DTA via the DTA Interface Connector 104.

Figure 9:
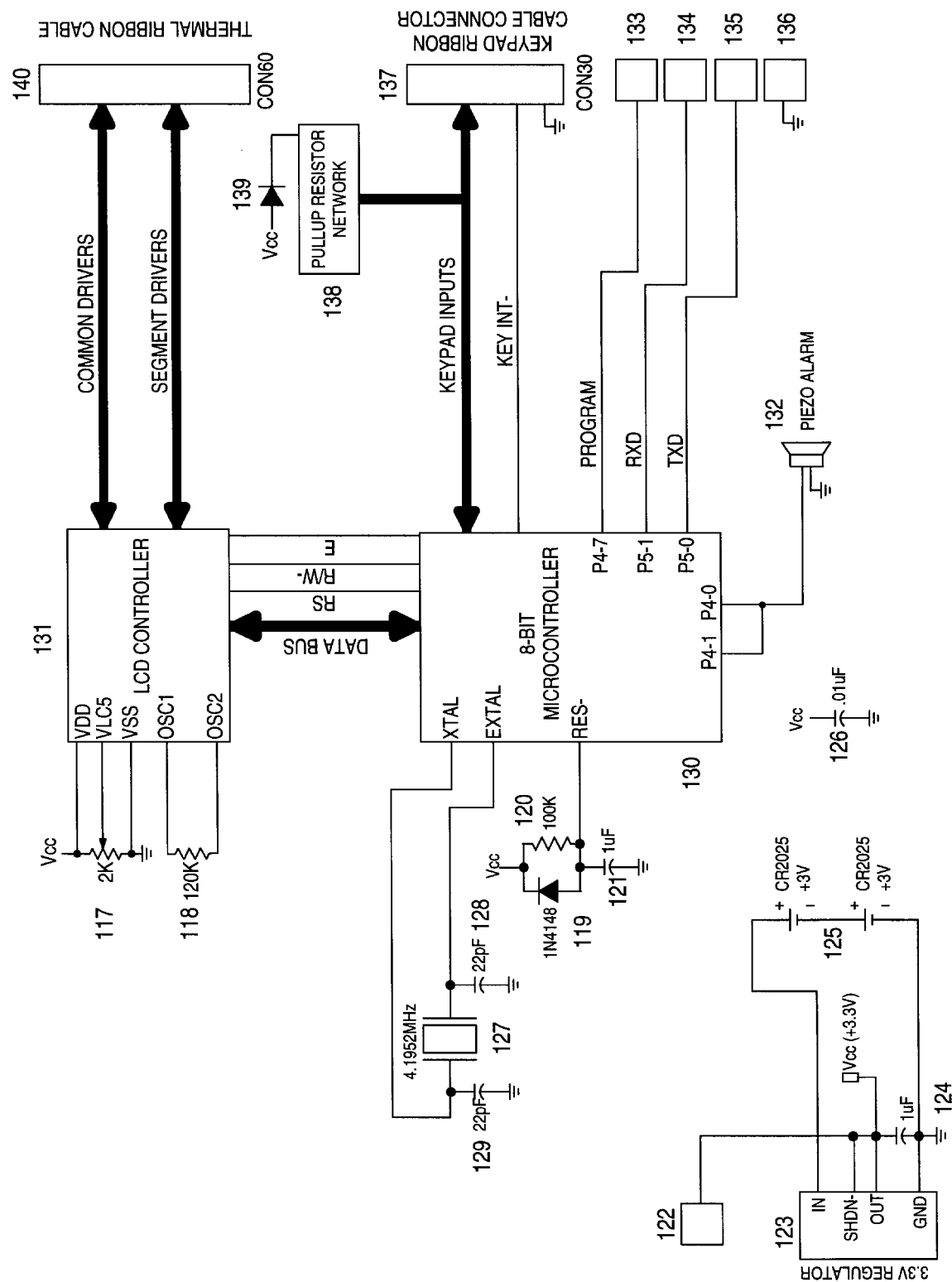
FIG. 9 Shows a detailed circuit diagram of the Version-B Digital Training Assistant unit.

FIG. 9 Shows a detailed circuit diagram of the Version-B Digital Training Assistant unit.

Power is activated by a control signal from the DTA Programming Stand received at contact pad 122. The control signal is connected to the LT1121CS8-3.3 +3.3 VDC regulator 123 shutdown input. A logic high will enable the output of the regulator 123. The two CR2025 Lithium Coin Cell Batteries 125 supply +6 VDC to the regulator 123. The regulator has a single 1.0 uF filter capacitor 124.

The Resistor-Capacitor power-on reset circuit constructed with a diode 119, 100K resistor 120, and 1 uF capacitor 121 combine to give an RC constant of 100 mS. The reset signal is sent to the reset input of the 8-bit microcontroller 130.

The 8-Bit microcontroller 130 is a Hitachi H8/329 Series single-chip microcomputer (microcontroller). The microcontroller contains 32 Kbytes of Read Only Memory (ROM), 1 kbyte of Random Access Memory (RAM), one 16-bit free running timer, dual 8-bit timers, a serial communications interface, an A/D converter, and extensive bit controllable I/O ports. The microcontroller 130 operates at +3.3 VDC and utilizes a 4.9152 MHz AT-cut parallel resonating crystal 127 with associated 22 pF capacitors 128 & 129. A single 0.01 uF decoupling capacitor 126 is provided for the microcontroller 130.

The microcontroller's 130 P1, P2, and P7 I/O ports are used to receive keypad key press signals via the keypad ribbon cable connector 137. An interrupt signal from the keypad is generated for each key pressed and received by the microcontroller 130 through the INT0 input (P4-2). Pull-up resistors for those ports not equipped with built-in pull-ups is provided by 27K resistor network 138. A diode 139 is used to prevent current from the serial data lines sourced by the DTA Programming Stand to enter the VCC plane of the DTA circuitry.

The microcontroller 130 has a built-in asynchronous serial communications port. The receive and transmit data signals are connected to the DTA Programming Stand Interface Contacts 134 & 135. A signal ground 136 is provided to match grounds between DTA and Programming Stand. A program status signal originates from the microcontroller 130 port pin to the DTA Programming Stand Interface Contact 133.

The prerequisite 8-bit data interface to the T7934-0000 LCD Controller 131 is created by using the microcontroller's 130 P3 and P4 I/O ports. The LCD Controller 131 is connected to the 16-Character 5×8 dot matrix +3 V LCD display using a thermal ribbon connector pad(s) 140. Contrast control is achieved using attached 2 KOhm potentiometer 117. The T7934-0000 LCD Controller 131 operates using an 120 KOhm oscillation resistor 118.

A piezo type au indicator 132 capable of being driven by a +3.3 V square wave is connected directly to the microcontroller's 130 P4-0 and P4-1 I/O pins (tied together for added drive) to provide audio alarms queues.

Figure 10:
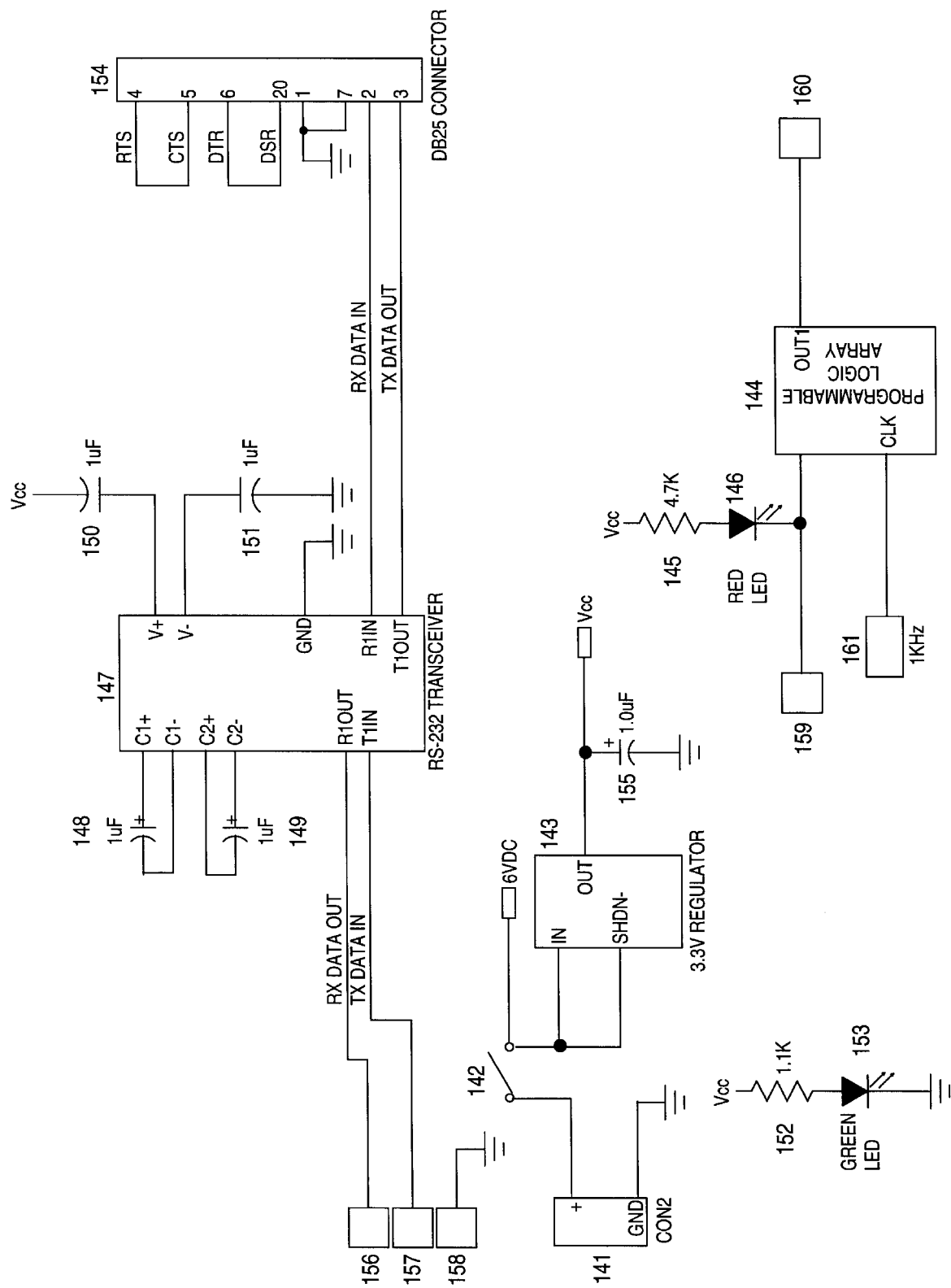
FIG. 10 Shows a detailed circuit diagram of the Version-B DTA Programming Stand.

FIG. 10 Shows a detailed circuit diagram of the Version-B DTA Programming Stand.

Power to the DTA Programming Stand is supplied by an external AC to DC regulated power supply producing +6 VDC at 400 mA minimum to the DC Power Jack 141. The power switch 142 routes power to the LT1121CN8-3.3 regulator 143 which supplies +3.3 VDC to the remaining circuitry, A single output filter 1 uF capacitor 155 is used. A green LED 153 and associated current limiting resistor 152 indicate the presence of power to the DTA Programming Stand.

The DTA Power Control Logic programmable array logic (PAL) device 144 will accept the DTA program status signal from DTA Interface Contact 159 and issues the DTA power control signal to DTA Interface Contact 160. The 1 KHz oscillator 161 provides a clock signal to operate the logic state machine programmed into the DTA Power Control Logic PAL 144.

The serial data interface to the host PC is provided using the DB-25 female connector 154. Appropriate control signals are tied together or ground to facilitate asynchronous communication. Transmit and receive data lines are routed to the MAX561CWI +3.3 V Transceiver w/Two EIA/TIA-562 Receivers 147. The RS-232C signal levels from the host PC are converted to the +3.3 V logical levels for the DTA units and vice versa. Charge-pump 1 uF capacitors 148, 149, 150, & 151 completed the transceiver/converter design.

The DTA Interface Contacts 156 & 157 route serial data transmit and receive signals to the EIA/TIA-562 transceiver/ converter 147 directly. A common signal ground is provided to equalize voltage levels between the DTA and Programming Stand through DTA Interface Contact 158. A red LED 146 and associated current limiting resistor 145 are used to indicate programming status using a signal from the DTA via the DTA Interface Contact 159.

Figure 23:
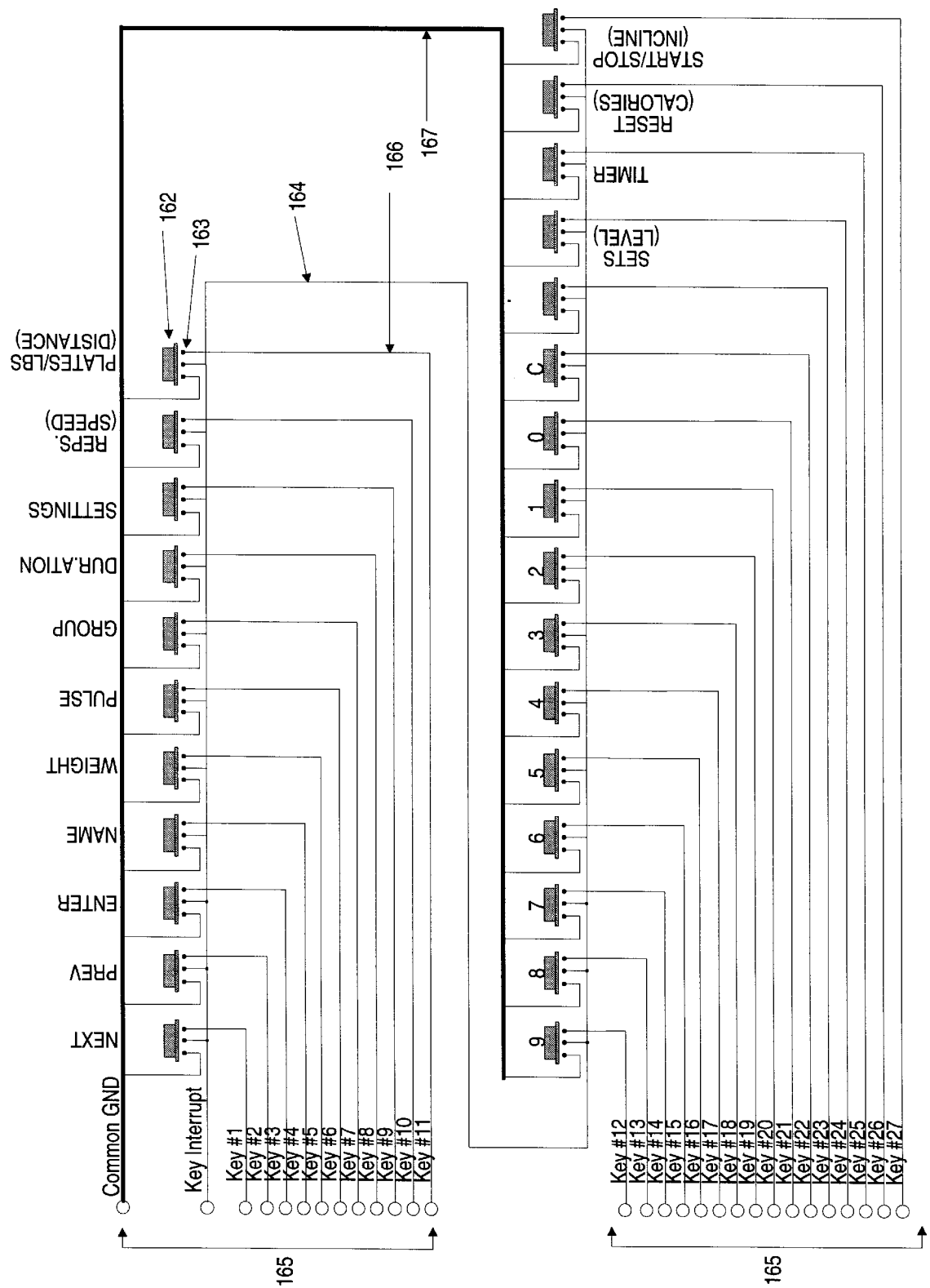
FIG. 23 Shows a detailed circuit diagram of the Version-A DTA Unit Keypad.

FIG. 23 Shows a detailed circuit diagram of the Version-A DTA Unit Keypad.

The elastomer keypad overlays a printed circuit board (PCB) containing electrical traces 166, 167, & 164. Each keypad protrusion 162 contains a carbon contact pill. The contact pills will cause a short circuit across the printed circuit board traces located under the pill 163 when pressed down onto the PCB. The keypad has a common trace to all key locations that is connected to signal ground 167. This will electrically ground the other two traces under the contact pill when the key is pressed onto the PCB. A common Key Interrupt signal 164 is routed to all key locations to generate a logic 0 signal with any key press. The individual key actuation signals 166 are routed to a pair of 15 pin header strips 165.

Figure 24:
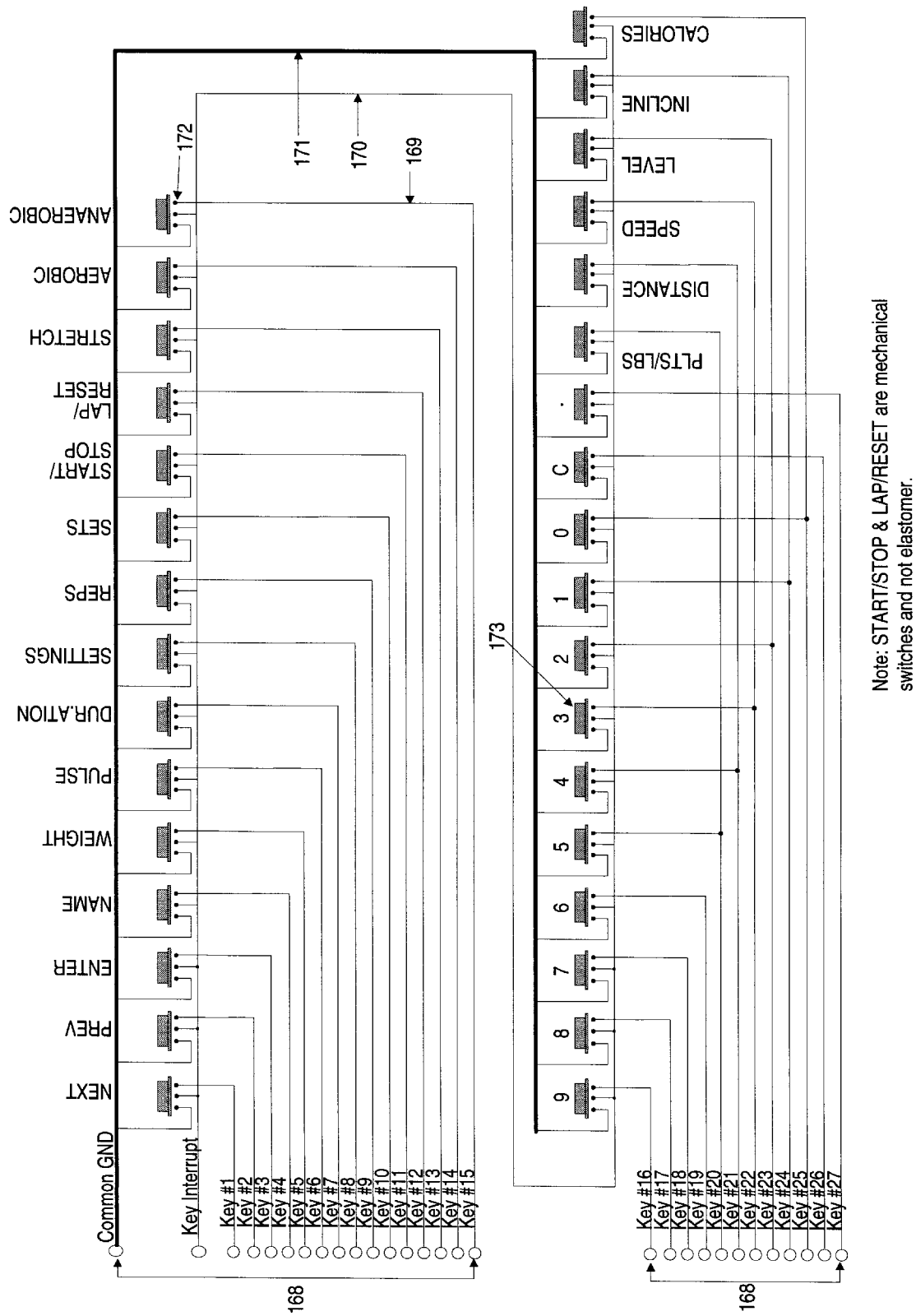
FIG. 24 Shows a detailed circuit diagram of the Version-B DTA Unit Keypad.

FIG. 24 Shows a detailed circuit diagram of the Version-B DTA Unit Keypad.

The elastomer keypad overlays a printed circuit board (PCB) containing electrical traces 169, 170, & 171. Each keypad protrusion 173 contains a carbon contact pill. The contact pills will cause a short circuit across the printed circuit board traces located under the pill 172 when pressed down onto the PCB. The keypad has a common trace to all key locations that is connected to signal ground 171. This will electrically ground the other two traces under the contact pill when the key is pressed onto the PCB. A common Key Interrupt signal 170 is routed to all key locations to generate a logic 0 signal with any key press. The individual key actuation signals 169 are routed to a ribbon connector 168. Six of the 33 keys share a common actuation signal path and are discerned by the context in which they are activated.

The START/STOP and LAP/RESET keys are not physically part of the elastomer keypad but their signals are routed the same PCB using separate wires.

Figure 22:
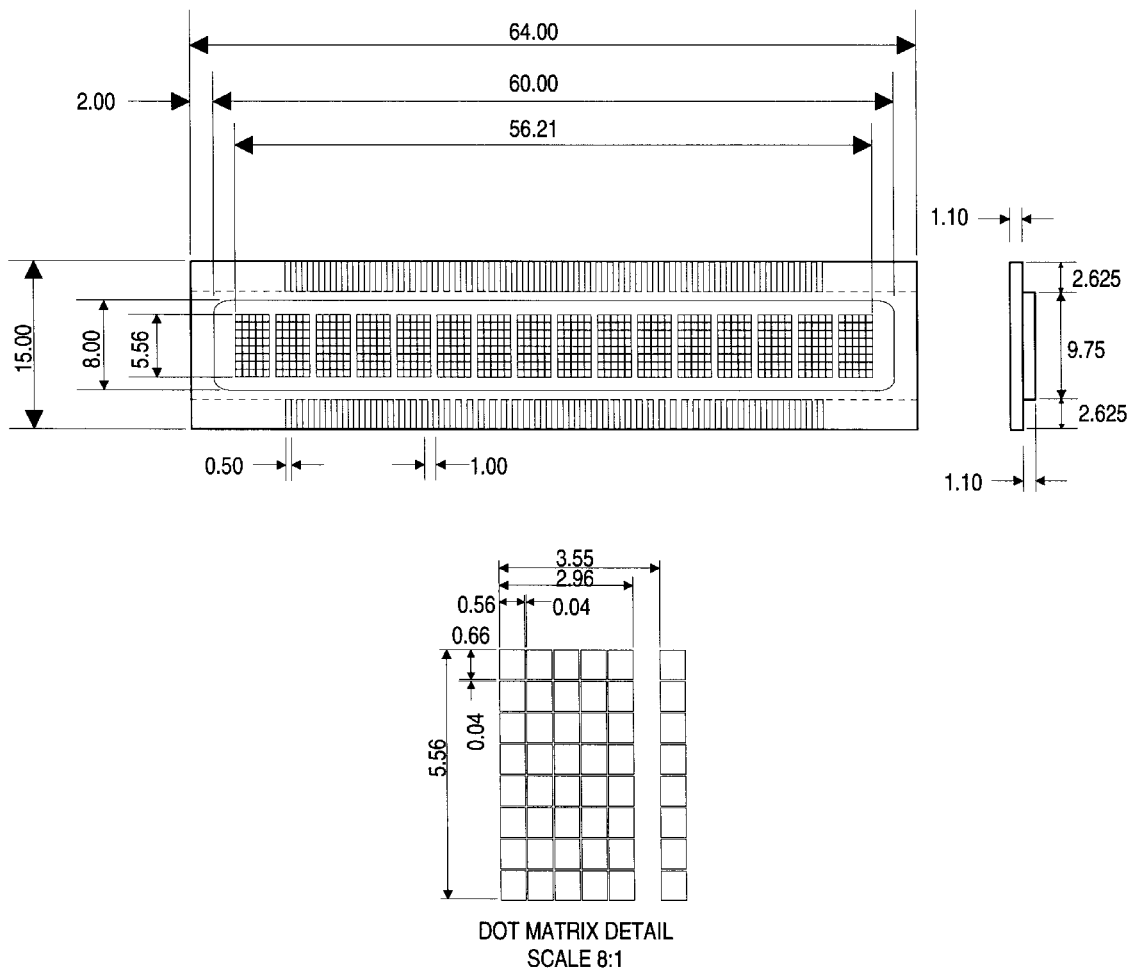
FIG. 22 Shows a detail of the Version-B DTA unit LCD display glass.

FIG. 22 Shows a detail of the Version-B DTA unit LCD display glass.

The Liquid Crystal Display (LCD) glass for the Version-B DTA unit is a custom design utilizing +3 V actuated liquid crystal. The dimensions depicted are also unique to the DTA design.

E. DTA Firmware Description

The microcontroller contains a software program resident in the 32K Read Only Memory (ROM). This program is responsible for the operational interface of the DTA unit encompassing LCD display functions, keypad interface, and serial data transmission/reception. The following paragraphs and figures describe the DTA firmware operation. Where noted, differences between the Version-A and Version-B DTA units are explained Prior to firmware explanations, a brief discussion of the software interface between the System application software and the DTA is in order.

An exercise routine is formatted into a contiguous digital data stream composed of distinct blocks. The individual bytes of the blocks conform to a strict format as described herein. The routine is compiled by the System application software as the output of a specific function and transmitted to the DTA using the DTA Programming Stand. Once received by the DTA, the DTA's microcontroller and associated firmware program can access, display, and modify the data in the exercise routine as required. The entire modified routine is then eventually transmitted back to the System for reincorporation.

The exercise routine is proceeded by a header block. The block is composed of nineteen bytes describing the client's name and membership number, body weight and pulse measurement. A master Header Command byte determines what mode the DTA is operating under:

00=Normal Mode (normal operation)

02=Learn Mode (allows changes in equipment mechanical/ergonomically settings)

Following the header bytes are the individual Exercise Description Blocks (EDB). The DTA's RAM will support as many exercise blocks as will fit into 960 bytes. The System application software is charged with limiting the formatted exercise routine to this physical limit.

There are six different types of EDBs. These blocks describe the individual exercises that make up the exercise routine. Those blocks specified as having a "Table Lookup" use a code number in place of character bytes that represent the 16-character maximum exercise description displayed by the DTA. A corresponding table of exercise description strings is hardcoded in the DTA's microcontroller's ROM. This method conserves valuable RAM space when an exercise included in the table is used in place of a user defined exercise name.

The following tables describe the formats of the uploaded workout routine data package and associated EDBs:

| HEADER BLOCK | |
|---|---|
| BYTE 1 | HEADER COMMAND |
| BYTE 2 | MEMBER # LSB |
| BYTE 3 | MEMBER # |
| BYTE 4 | MEMBER # |
| BYTE 5 | MEMBER # MSB |
| BYTE 6 | # OF CHARACTERS IN NAME (0–16) |
| BYTE 7 | 222 11111 |
| BYTE 8 | 4 3333 22 |
| BYTE 9 | 55555 4444 |
| BYTE 10 | 77 66666 5 |
| BYTE 11 | 88888 777 |
| BYTE 12 | AAA 99999 |
| BYTE 13 | C BBBBB AA |
| BYTE 14 | DDDD CCCC |
| BYTE 15 | FF EEEEE D |
| BYTE 16 | GGGGG FFF |
| BYTE 17 | WEIGHT LSB |
| BYTE 18 | WEIGHT MSB |
| BYTE 19 | PULSE |
| . | |
| . | <Individual Exercise Description Blocks> |
| . | |
| FOOTER BYTE | |
| CHECKSUM BYTE | |

| ANAEROBIC EXERCISE DESCRIPTION BLOCK | | |
|---|---|---|
| BYTE 1 | COMMAND BYTE | |
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7-5: | # OF SETTINGS |
| | BITS 4-0: | Setting #1 |

| ANAEROBIC EXERCISE DESCRIPTION BLOCK | | |
|---|---|---|
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
|  | BIT 6: | Spare |
|  | BIT 7: | Completed Status; 0=completed 1=modified |
| BYTE 8 | BIT 7: | 0=POUNDS 1=PLATES |
|  | BIT 6: | 1 = Decimal in pounds/Plate 0= No decimal |
|  | BITS 5-0: | POUNDS/PLATES MSB |
| BYTE 9 | BITS 7-0 | POUNDS/PLATES LSB |
| BYTE 10 | BITS 7-4 | Duration type 0 = seconds 1 = minutes 2=hours |
|  | BITS 3-0 | Spare |
| BYTE11 | BITS 7 - 0 | DURATION |
| BYTE 12 | BITS 7 - 0 | REPS |
| BYTE 13 | BITS 7-4: | SETS |
|  | BITS 3-0 | #CHARACTERS IN EQUIPMENT NAME(1–16)+1 |
| BYTE 14 | 222 11111 |  |
| BYTE 15 | 4 33333 22 |  |
| BYTE 16 | 5555 4444 |  |
| BYTE 17 | 77 66666 5 |  |
| BYTE 18 | 88888 777 |  |
| BYTE 19 | AAA 99999 |  |
| BYTE 20 | C BBBBB AA |  |
| BYTE 21 | DDDD CCCC |  |
| BYTE 22 | FF EEEEE D |  |
| BYTE 23 | GGGGG FFF |  |

| ANAEROBIC W/TABLE LOOKUP EXERCISE DESCRIPTION BLOCK | | |
|---|---|---|
| BYTE 1 | COMMAND BYTE | |
| BYTE 2 | BIT 7: | Spare |
|  | BIT 6: | Setting 7 1 = ALPHA 0 = NUMERIC |
|  | BIT 5: | Setting 6 1 = ALPHA 0 = NUMERIC |
|  | BIT 4: | Setting 5 1 = ALPHA 0 = NUMERIC |
|  | BIT 3: | Setting 4 1 = ALPHA 0 = NUMERIC |
|  | BIT 2: | Setting 3 1 = ALPHA 0 = NUMERIC |
|  | BIT 1: | Setting 2 1 = ALPHA 0 = NUMERIC |
|  | BIT 0: | Setting 1 1 = ALPHA 0 = NUMERIC |
| BYTE 3 | BITS 7-5: | # OF SETTINGS |
|  | BITS 4-0: | Setting #1 |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
|  | BIT 6: | Spare |
|  | BIT 7: | Completed Status; 0=completed 1=modified |
| BYTE 8 | BIT 7: | 0=POUNDS 1=PLATES |
|  | BIT 6: | 1 = Decimal in pounds/Plate 0= No decimal |
|  | BITS 5-0: | POUNDS/PLATES MSB |
| BYTE 9 | BITS 7-0 | POUNDS/PLATES LSB |
| BYTE 10 | BITS 7-0 | REPS |
| BYTE11 | BITS 7-4: | SETS |
|  | BITS 3-0 | Duration type 0=seconds 1=minutes 2=hours |
| BYTE 12 | BITS 7 - 0 | DURATION |
| BYTE 13 | LOOKUP TABLE # LSB | |
| BYTE 14 | LOOKUP TABLE # MSB | |

| AEROBIC EXERCISE DESCRIPTION BLOCK | | |
|---|---|---|
| BYTE 1 | COMMAND BYTE | |
| BYTE 2 | BIT 7: | Spare |
|  | BIT 6: | Setting 7 1 = ALPHA 0 = NUMERIC |
|  | BIT 5: | Setting 6 1 = ALPHA 0 = NUMERIC |
|  | BIT 4: | Setting 5 1 = ALPHA 0 = NUMERIC |
|  | BIT 3: | Setting 4 1 = ALPHA 0 = NUMERIC |
|  | BIT 2: | Setting 3 1 = ALPHA 0 = NUMERIC |
|  | BIT 1: | Setting 2 1 = ALPHA 0 = NUMERIC |
|  | BIT 0: | Setting 1 1 = ALPHA 0 = NUMERIC |
| BYTE 3 | BITS 7-5: | # OF SETTINGS |
|  | BITS 4-0: | Setting #1 |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
|  | BIT 6: | Spare |
|  | BIT 7: | Completed Status; 0=completed 1=modified |
| BYTE 8 | BIT 7-0: | INTENSITY beats per minute |
| BYTE 9 | BITS 7: | 1=LEVEL IS ALPHA 0=LEVEL IS NUMERIC |
|  | BITS 6-0: | LEVEL |
| BYTE 10 | BITS 7-5: | RATE: 0=MPH 1=KPH 2=FPM 3=MPM 4=SPM 5 -7=sp |
|  | BITS 4-0: | INCLINE |
| BYTE 11 | BIT 7 | SPEED Decimal Indicator 1 = decimal point 0 = no decimal |
|  | BITS 6-0 | SPEED MSB |
| BYTE 12 | BITS 7-0 | SPEED LSB |
| BYTE 13 | BITS 7-0: | CALORIES x 10 |
| BYTE 14 | BIT 7-6: | Distance Type 0= Miles 1= feet 2= Kilometers 3= Meters |
|  | BIT 5 | Distance Decimal Indicator 1 = decimal present |
|  | BITS 4-0 | DISTANCE MSB |
| BYTE 15: | BITS 7-0: | DISTANCE LSB |
| BYTE 16 | BITS 7-0: | DURATION |
| BYTE 17: | BITS 7-4: | Duration type 0 = seconds 1=minutes 2=hours |
|  | BITS 3-0 | # CHARACTERS IN EQUIPMENT NAME(1–16)+1 |
| BYTE 18 | 222 11111 | |
| BYTE 19 | 4 33333 22 | |
| BYTE 20 | 5555 4444 | |
| BYTE 21 | 77 66666 5 | |
| BYTE 22 | 88888 777 | |
| BYTE 23 | AAA 99999 | |

-continued

| AEROBIC EXERCISE DESCRIPTION BLOCK | |
|---|---|
| BYTE 24 | C BBBBB AA |
| BYTE 25 | DDDD CCCC |
| BYTE 26 | FF EEEEE D |
| BYTE 27 | GGGGG FFF |

| AEROBIC W/TABLE LOOKUP EXERCISE DESCRIPTION BLOCK | | |
|---|---|---|
| BYTE 1 | COMMAND BYTE | |
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7-5: | # OF SETTINGS |
| | BITS 4-0: | Setting #1 |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Completed Status; 0=completed 1=modified |
| BYTE 8 | BIT 7-0: | INTENSITY beats per minute |
| BYTE 9 | BITS 7: | 1=LEVEL IS ALPHA 0=LEVEL IS NUMERIC |
| | BITS 6-0: | LEVEL |
| BYTE 10 | BITS 7-5: | RATE: 0=MPH 1=KPH 2=FPM 3=MPM 4=SPM 5 -7=sp |
| | BITS 4-0: | INCLINE |
| BYTE 11 | BIT 7 | SPEED Decimal Indicator 1= decimal point 0 = no decimal |
| | BITS 6-0 | SPEED MSB |
| BYTE 12 | BITS 7-0 | SPEED LSB |
| BYTE 13 | BITS 7-0: | CALORIES × 10 |
| BYTE 14 | BIT 7-6: | Distance Type 0= Miles 1= feet 2= Kilometers 3= Meters |
| | BIT 5 | Distance Decimal Indicator 1 = decimal present |
| | BITS 4-0 | DISTANCE MSB |
| BYTE 15: | BITS 7-0: | DISTANCE LSB |
| BYTE 16: | BITS 7-0: | DURATION |
| BYTE 17: | BITS 7-4: | Duration type 0 = seconds 1=minutes 2=hours |
| | BITS 3-0: | Spare |
| BYTE 18 | LOOKUP TABLE # LSB | |
| BYTE 19 | LOOKUP TABLE # MSB | |

| STRETCH EXERCISE DESCRIPTION BLOCK | | |
|---|---|---|
| BYTE 1 | COMMAND BYTE | |
| BYTE 2 | BITS 7-0: | DURATION |
| BYTE 3 | BITS 7-4: | Duration type 0 = seconds 1=minutes 2=hours |
| | BITS 3-1: | Spare |
| | BIT 0: | Completed Status; 0= completed 1=modified |
| BYTE 4 | BIT 7-0: | REPS |
| BYTE 5 | BITS 7-4: | SETS |
| | BITS 3-0 | # CHARACTERS IN EQUIPMENT NAME(1–16)+1 |
| BYTE 6 | 222 11111 | |
| BYTE 7 | 4 33333 22 | |
| BYTE 8 | 5555 4444 | |
| BYTE 9 | 77 66666 5 | |
| BYTE 10 | 88888 777 | |
| BYTE 11 | AAA 99999 | |
| BYTE 12 | C BBBBB AA | |
| BYTE 13 | DDDD CCCC | |
| BYTE 14 | FF EEEEE D | |
| BYTE 15 | GGGGG FFF | |

| STRETCH W/TABLE LOOKUP EXERCISE DESCRIPTION BLOCK | | |
|---|---|---|
| BYTE 1 | COMMAND BYTE | |
| BYTE 2 | BITS 7-0: | DURATION |
| BYTE 3 | BITS 7-4: | Duration type 0 = seconds 1=minutes 2=hours |
| | BITS 3-1: | Spare |
| | BIT 0: | Completed Status; 0= completed 1=modified |
| BYTE 4 | BIT 7-0: | REPS |
| BYTE 5 | BITS 7-4: | SETS |
| | BITS 3-0 | not used |
| BYTE 6 | LOOKUP TABLE # LSB | |
| BYTE 7 | LOOKUP TABLE # MSB | |

Figure 11:
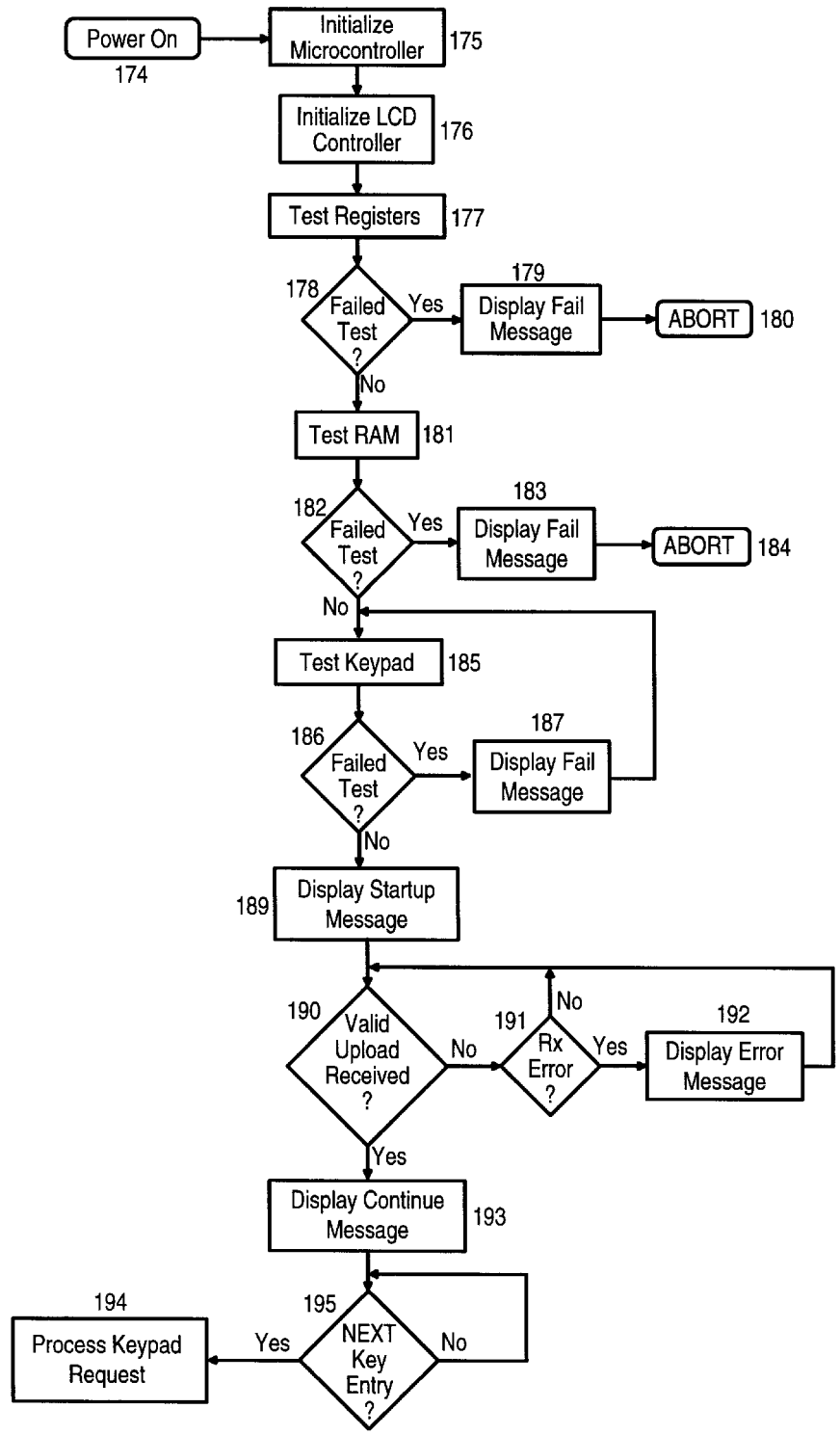
FIG. 11 Shows a flow diagram of both Version A & B DTA firmware power-on sequence.

FIG. 11 Shows a flow diagram of both Version A & B DTA firmware power-on sequence.

When power is applied to the DTA's microcontroller, the microcontroller's program execution unit will reset and begin execution at Power On 174. The program then initializes the microcontroller 175 setting up various internal registers and the interrupt vector table. Next the program will initialize the OEM LCD Display Module's T7934 LCD Controller 176.

Following initialization, the program will perform some internal self tests. The registers located in the microcontroller are tested for both read and write capability 177. If the any part of the test fails 178, the alarm is sounded and a message is displayed on the LCD with a specific code number indicating the failed register 179. The program jumps to an infinite loop 180 causing a general program abort. The DTA must be powered off then on to reset.

The 1 Kbyte RAM is tested next 181 using seven different bit patterns written to and then read from all the RAM locations. If an error is detected at any stage of the test 182, the alarm is sounded and a message is displayed on the LCD with a specific code number indicating the failed location 183. The program jumps to an infinite loop 184 causing a general program abort. The DTA must be powered off then on to reset.

The keypad connected to the microcontroller via the I/O ports is tested to determine if any keys are stuck active 185. If a key is detected as being stuck on 186, the alarm is sounded and a special message is displayed on the LCD with the offending key number 187. The test repeats until the key is unstuck.

Once the testing has completed successfully, the start message is displayed: "Physical Genius" 189 followed by: "Ready to Program" message. The program enters a loop 190 awaiting the reception of a exercise routine data upload.

While in the waiting loop 190, the program checks for any receiver errors 191. If detected, the alarm is sounded and a special message is displayed 192 describing the offending error. The routine will reset awaiting reception of more data.

When a valid upload of a workout routine is received, a new message is displayed 193 instructing the user to advance the program with the NEXT key. The program now enters a waiting loop 195 looking for a NEXT key activation. Upon detection of the key, the program will process the keypad key request 194.

From this point on, the program is event driven. Keypad requests will determine what function the program executes next and further keypad requests control the sub-functionality therein.

When a key is activated, an interrupt signal is generated to the microcontroller which activates a special interrupt processing routine. The keyboard I/O port pins are scanned and the activated key's signal is detected. The keyboard interrupt routine will return a number representing the key that was detected as being active.

Figure 12:
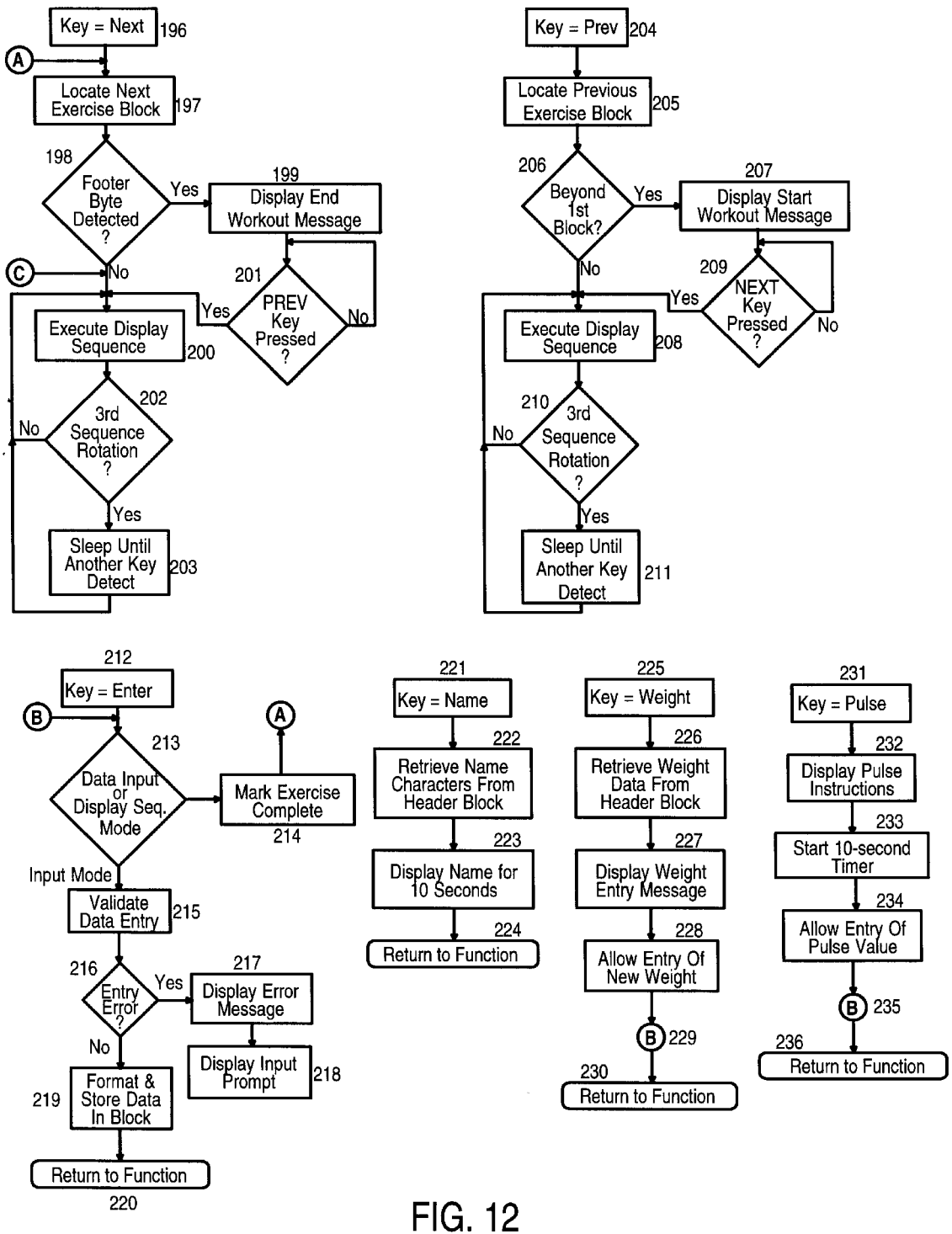
FIG. 12 Shows a flow diagram of both Version A & B DTA firmware NEXT, PREV, ENTER, NAME, PULSE, and WEIGHT keypad key activation sequences FIG. 13 Shows a flow diagram of the Version-A DTA firmware GROUP keypad key activation sequence.

FIG. 12 Shows a flow diagram of both Version A & B DTA firmware NEXT, PREV, ENTER, NAME, PULSE, and WEIGHT keypad key activation sequences.

When the NEXT Key has been detected 196, the program will locate the next exercise description block 197. If while searching for the next EDB, the program encounters the Footer byte indicating the end of the upload block 198, a special message is displayed 199 instructing the user to hit the PREV key. The program waits until the PREV key is hit 201. When detected the program will execute the display sequence routine 200 for the EDB that was being displayed prior to the NEXT key activation.

The exercise display sequence routine 200 will parse out the elements of the exercise description block (EDB) and display them on the LCD display. Where indicated, if the associated exercise parameter is 0, the parameter's display will be omitted. The following tables depict the display sequence for each main type of exercise:

| STRETCH Excerises: | ANAEROBIC Exercises: | AEROBIC Exercises: |
|---|---|---|
| Name of Exercise | Name of Exercise | Name of Exercise |
| delay 3 seconds | delay 3 seconds | delay 3 seconds |
| Repetitions Setting | Mechanical/ | Mechanically/ |
| (if not 0) | Ergonomically | Ergonomically |
| delay 3 seconds | Settings | Settings |
| Sets Setting | delay 3 seconds | delay 3 seconds |
| (if not 0) | Pounds/Plates Setting | Duration Setting |
| delay 3 seconds | (if not 0) | (if not 0) |
|  | delay 3 seconds | delay 3 seconds |
|  | Repetitions Setting | Distance Setting |
|  | (if not 0) | (if not 0) |
|  | delay 3 seconds | delay 3 seconds |
|  | Sets Setting | Speed Setting |
|  | (if not 0) | (if not 0) |
|  | delay 3 seconds | delay 3 seconds |
|  | Duration Setting | Intensity Setting |
|  | (if not 0) | (if not 0) |
|  | delay 3 seconds | delay 3 seconds |
|  |  | Calorie Setting |
|  |  | (if not 0) |
|  |  | delay 3 seconds |
|  |  | Incline Setting |
|  |  | (if not 0) |
|  |  | delay 3 seconds |
|  |  | Level Setting |
|  |  | (if not 0) |
|  |  | delay 3 seconds |

The sequence is repeated three times 202 after which the microprocessor will enter its low power sleep mode 203 until a keypad key is pressed and thus the activation interrupt is detected. The sequence will then restart at the top. Any time during the display sequence, the program will be able to process keypad key activation interrupts and act accordingly.

When the PREV Key has been detected 204, the program will locate the previous EDB 205. If while searching for the previous exercise description block, the program advances beyond the beginning of the exercise description space 206, a special message is displayed 207 instructing the user to hit the NEXT key. The program waits until the NEXT key is hit 209. When detected the program will continue to the display sequence routine of the EDB being displayed prior to activating the PREV key 208.

The sequence is repeated three times 210 after which the microprocessor will enter its low power sleep mode 211 until a keypad key is pressed and thus the activation interrupt is detected. The sequence will then restart at the top.

If the ENTER key is detected 212, the program must first decide the context of the key's activation 213. If the key is used as data input confirmation, the data is then validated according to the context of the data entry 215. If there is a detected entry error 216, a special message is displayed indicating the error and corrective action 217. The program then repeats the original data entry prompt routine 218 followed by another ENTER key detection 212. If the data was determined as valid and correct it is formatted and stored in the appropriate location in the current EDB or Header Block location 219. The program then continues from where it was originally interrupted or made the function call 220.

If the context of the ENTER key was not as data input confirmation then it is used to mark the current EDB as being completed 214. The program then continues at Marker A.

If the NAME key is detected 221, the client's name characters are extracted and reconstructed as ASCII characters 222 from the Header Block bytes 7 through 16. The bytes are then sent to the LCD Display Controller for a ten second display 223. Following the interval, the program returns to the point of interruption 224.

If the WEIGHT key is detected 225, the weight entry function is activated with the original weight value stored in the uploaded Header Block extracted 226 from bytes 17 and 18. The bytes are converted to ASCII and sent to the LCD Display Controller for display 227. The program then prompts for a new entry 228 allowing a three digit plus one decimal place value. The program continues at Marker B for ENTER key processing 229. When successfully concluded, the program will return to the point of interruption 230.

If the PULSE key is detected 231, the pulse entry function is activated. The function will interactively instruct, via the LCD display, the user on how and when to measure his pulse 232. The program will then start a ten second timer 233. At the conclusion of the time interval, the alarm sounds and the program prompts for the new measured pulse count entry 234. The program continues at the Marker B for ENTER key processing 235. When successfully concluded, the program will return to the point of interruption 236.

Figure 13:
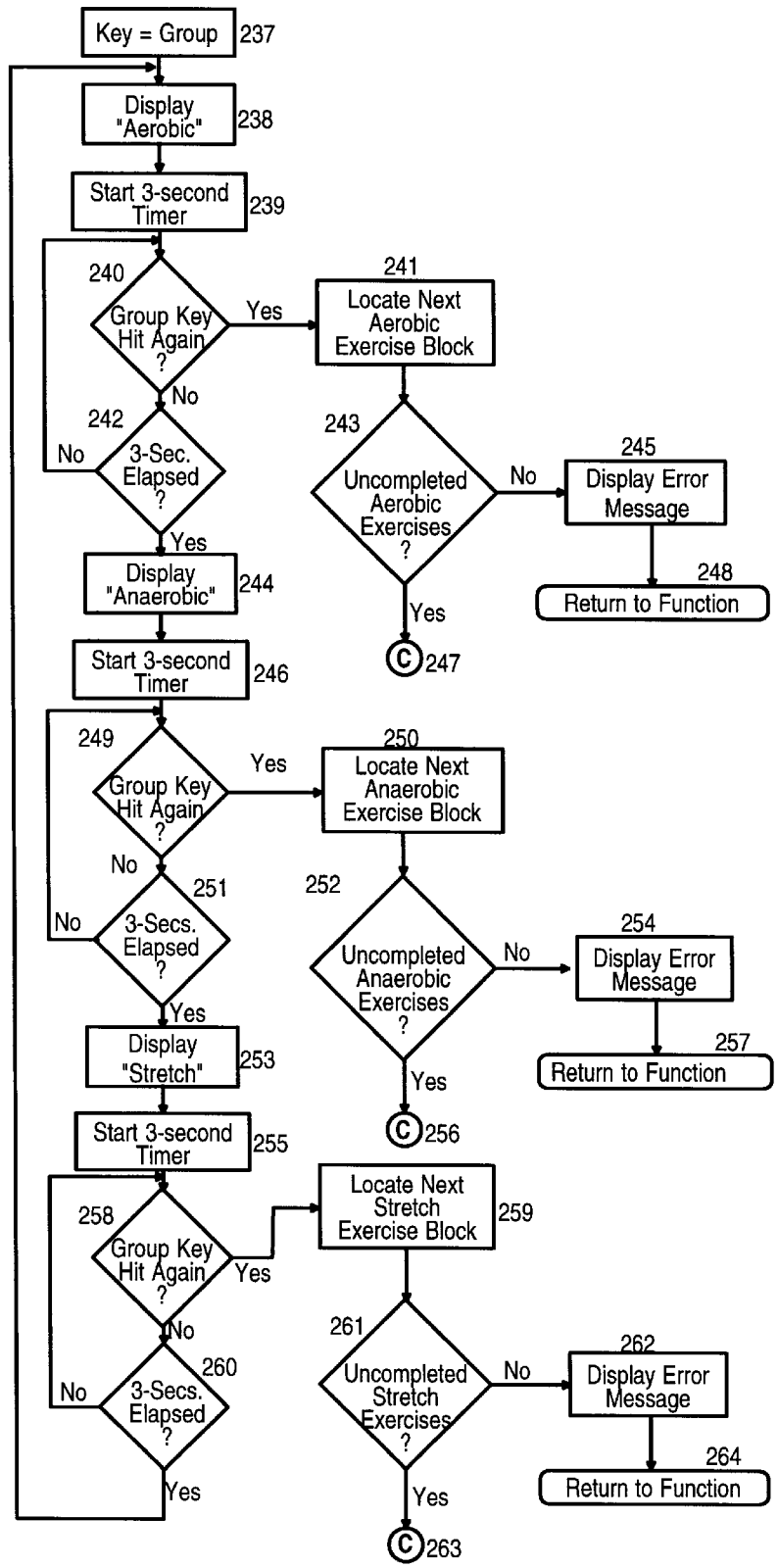

FIG. 13 Shows a flow diagram of the Version-A DTA firmware GROUP keypad key activation sequence.

The GROUP key is used to advance the exercise program out of the predetermined sequence to the next available exercise in the specified group (Aerobic Anaerobic, or Stretch). If the GROUP key is detected 237, the word "Aerobic" is displayed 238. A three second timer is started 239 and if the GROUP key is detected again 240 within the interval, the program will locate the first available Aerobic type EDB 241. The display sequence is activated at Marker C, 247. If no uncompleted Aerobic EDB is found 243, a special error display message is used 245 and the program returns to the point of interruption 248.

If the three second timer is allowed to elapse 242, the word "Anaerobic" is displayed 244. A three second timer is started 246 and if the GROUP key is detected again 249 within the interval, the program will locate the first available Anaerobic type EDB 250. The display sequence is activated at Marker C 256. If no uncompleted Anaerobic EDB is found 252, a special error display message is used 254 and the program returns to the point of interruption 257.

If the three second timer is allowed to elapse 251, the word "Stretch" is displayed 253. A three second timer is started 255 and if the GROUP key is detected again 258 within the interval, the program will locate the first available Stretch type EDB 259. The display sequence is activated at Marker C 263. If no uncompleted Stretch EDB is found 261, a special error display message is used 262 and the program returns to the point of interruption 254.

If the three second timer is allowed to elapse 260, the sequence starts over again with displaying "Aerobic" 238.

Figure 14:
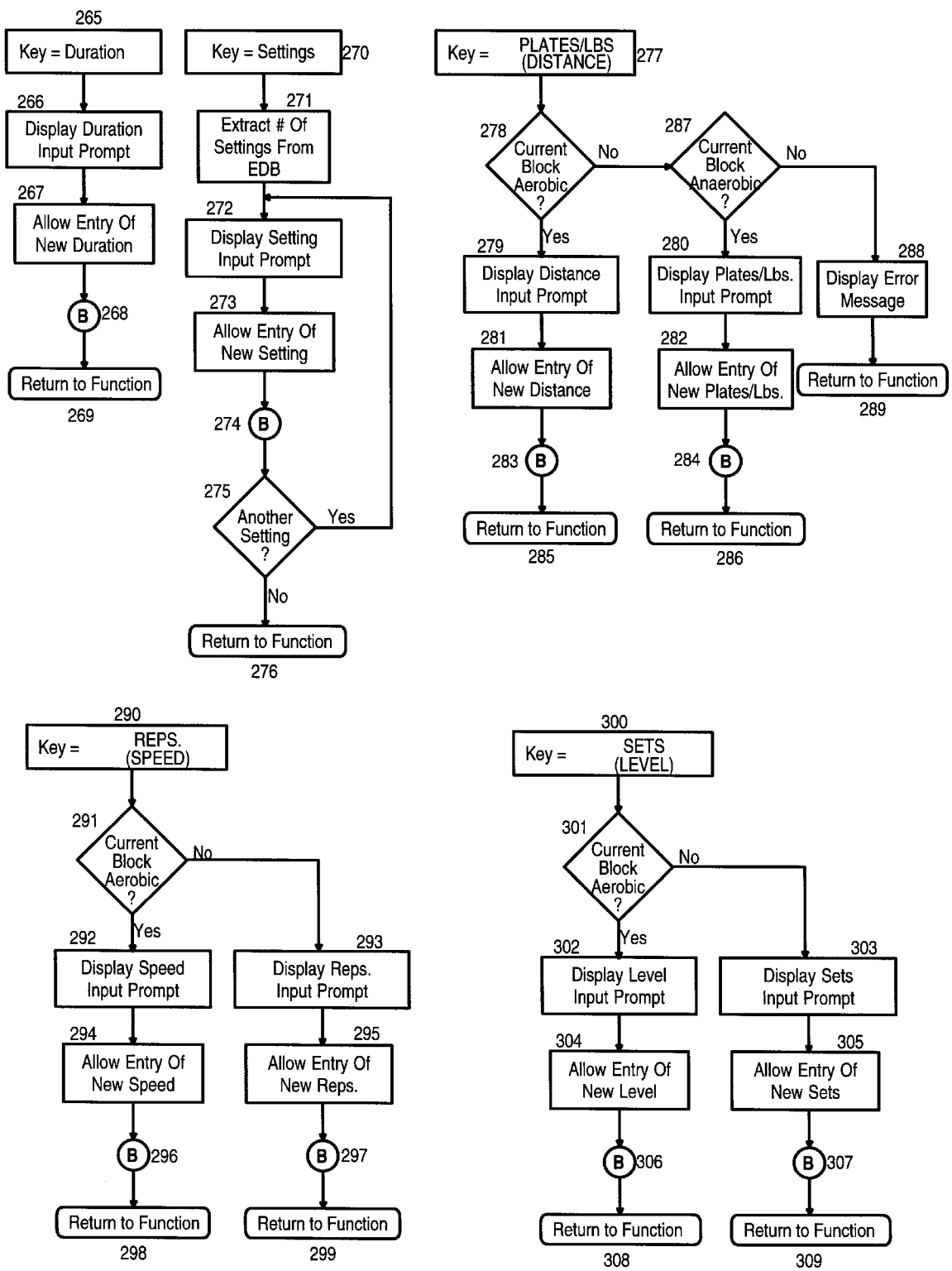
FIG. 14 Shows a flow diagram of the Version-A DTA firmware DURATION, SETTINGS, PLATES/LBS (DISTANCE), REPS. (SPEED), and SETS (LEVEL) keypad key activation sequences FIG. 15 Shows a flow diagram of the Version-A DTA firmware TIMER, START/STOP (DURATION), and RESET (CALORIES) keypad key activation sequences.

FIG. 14 Shows a flow diagram of the Version-A DTA firmware DURATION, SETTINGS, PLATES/LBS (DISTANCE), REPS. (SPEED), and SETS (LEVEL) keypad key activation sequences In the Version-A DTA unit firmware, selected keys perform dual functions depending upon the context in which they are activated If the DURATION key is detected 265, the program will extract the duration setting from the current EDB block 266 and allow a new input 267. The program continues at B Marker for ENTER key processing 268. When successfully concluded, the program will return to the point of interruption 269

If the SETTINGS key is detected 270, the program will first check if the current mode is Learn and that the EDB is not a Stretch type exercise. If otherwise, the function is not entered. If true, the program will extract the mechanical/ ergonomically settings 271 from the EDB and display the first setting 272. The program will now allow input of a new setting 273. The program continues at Marker B for ENTER key processing 274. When successfully concluded, the program will check to see if there is another setting to adjust 275. If so, the process is repeated for the remaining settings 272. If finished, the program will return to the point of interruption 276

If the PLATES/LBS (DISTANCE) key is detected 277, the program will first determine the context by examining the EDB for Aerobic type exercise 278. If Aerobic, the program will extract and display the Distance value 279. The program next allows the input of a new distance setting 281. The program continues at Marker B for ENTER key processing 283. When successfully concluded, the program will return to the point of interruption 285 If the EDB was Stretch 287, a special error message is displayed 288 and the program will return to the point of interruption 289. If the program determines the EDB is Anaerobic, the program will extract and display the Pounds/Plates value 280. The program next allows the input of a new Pounds/Plates setting 282. The program continues at Marker B for ENTER key processing 284. When successfully concluded, the program will return to the point of interruption 286

If the REPS. (SPEED) key is detected 290, the program will first determine the context by examining the EDB for Aerobic type exercise 291. If Aerobic, the program will extract and display the Speed value 292. The program next allows the input of a new speed setting 294. The program continues at Marker B for ENTER key processing 296. When successfully concluded, the program will return to the point of interruption 298

If the program determines the EDB is not Aerobic, the program will extract and display the Repetitions value 293. The program next allows the input of a new Repetitions setting 295. The program continues at Marker B for ENTER key processing 297. When successfully concluded, the program will return to the point of interruption 299

If the SETS. (LEVEL) key is detected 300, the program will first determine the context by examining the EDB for Aerobic type exercise 301. If Aerobic, the program will extract and display the Level value 302. The program next allows the input of a new level setting 304. The program continues at Marker B for ENTER key processing 306. When successfully concluded, the program will return to the point of interruption 308

If the program determines the EDB is not Aerobic, the program will extract and display the Sets value 303. The program next allows the input of a new Sets setting 305. The program continues at Marker B for ENTER key processing 307. When successfully concluded, the program will return to the point of interruption 309

Figure 15:
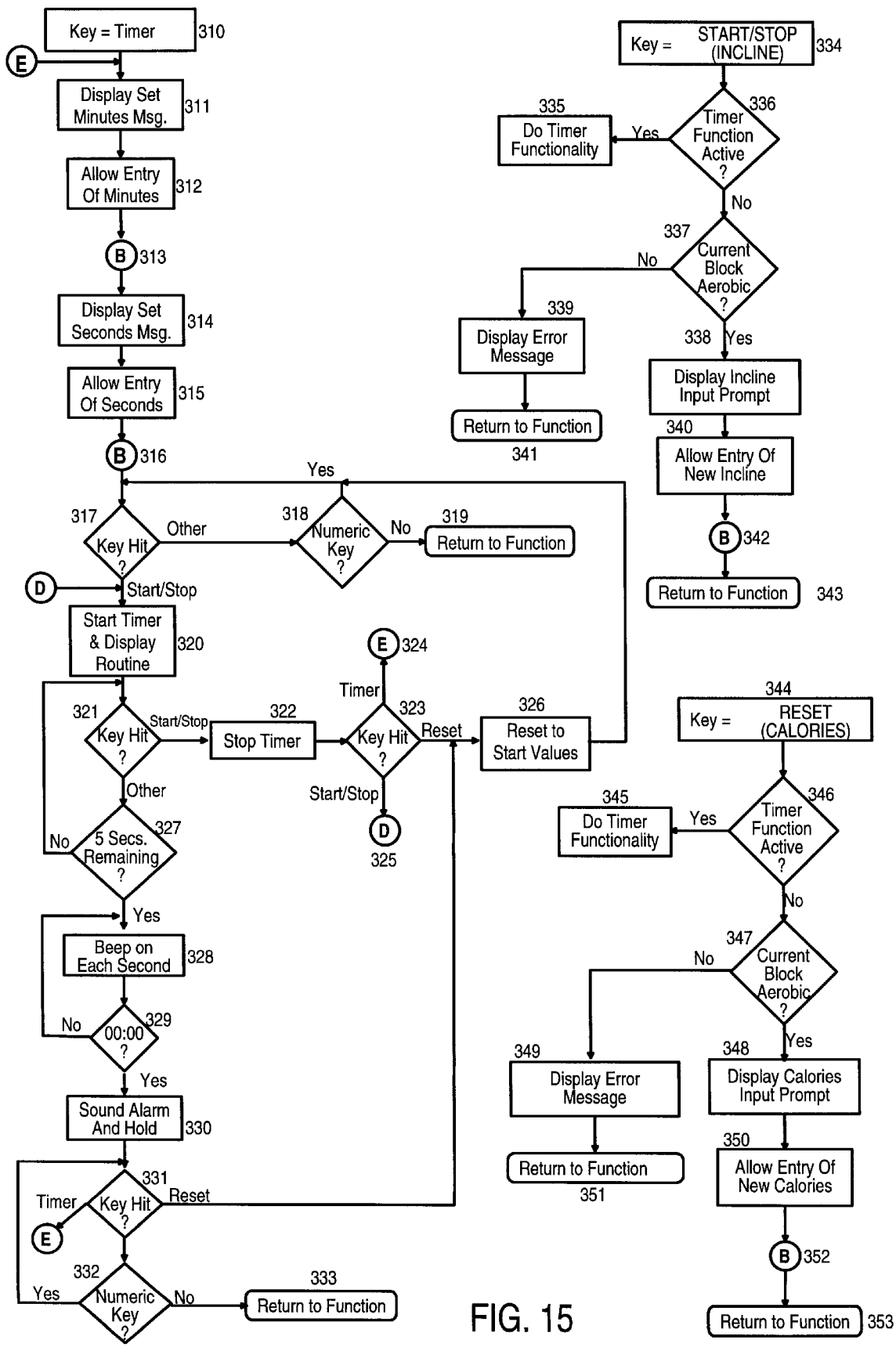

FIG. 15 Shows a flow diagram of the Version-A DTA firmware TIMER, START/STOP (DURATION), and RESET (CALORIES) keypad key activation sequences.

If the TIMER key is detected 310, the program enters the count down timer function. The program first displays the "Set Minutes" prompt 311. Entry of a minutes setting is enabled 312. The program continues at Marker B for ENTER key processing 313. When successfully concluded, the program will now display the "Set Seconds" prompt 314. Entry of a seconds setting is enabled 315. The program continues at Marker B for ENTER key processing 316. When successfully concluded, the program now waits for a keypad key activation 317. If the START/STOP (INCLINE) key is detected the timer and display time function is started 320.

For other detected keys, the program checks if it was a numeric key 318, if so the program ignores the key activation 317, If it is a function key, the program will return to the point of interruption 319.

After the timer and display time function has started 320, the program will also look for a key activation 321. Any other key but the START/STOP (INCLINE) key will be ignored. If the START/STOP (INCLINE) key is detected, the timer and time display are stopped 322. If the TIMER key is detected again 323, the program will continue at Marker E. If the RESET (CALORIES) key is detected, the timer is reset to the initial values 326 and program execution continues at 317. If the START/STOP (INCLINE) key is detected, the program execution continues at Marker D.

In the absence of the START/STOP (INCLINE) key detection, the timer will continue to count down to 00:00 while displaying the current remaining time. When the timer has reach 5 remaining seconds 327, the alarm will beep on each subsequent second 328. When the timer expires 329, the alarm will beep several times and the timer stop.

At this point, the program is waiting for another key activation 331. If the TIMER key is detected, the program continues execution at Marker E. If the RESET (CALORIES) key is detected, the program will reset the timer to the initial values 326 and continue execution at 317. If a numeric key was detected 332, the key activation is ignored. If it was a function key, the program will return to the point of interruption 333.

The START/STOP (INCLINE) and RESET (CALORIES) keys have dual functions. Following are descriptions of their alternative functions If the START/STOP (INCLINE) key is detected 334, the program determines what context it is currently in 336. If the timer is active, the timer functionality is used 335. If not in timer mode, the program checks to see if the current EDB is Aerobic 337. If not then a special error message is displayed 339 and the program will return to the point of interruption 341.

For an Aerobic EDB, the program will extract and display the Incline value 338. The program next allows the input of a new incline setting 340. The program continues at Marker B for ENTER key processing 342. When successfully concluded, the program will return to the point of interruption 343

If the RESET (CALORIES) key is detected 344, the program determines what context it is currently in 346. If the timer is active, the timer functionality is used 345. If not in timer mode, the program checks to see if the current EDB is Aerobic 347. If not then a special error message is displayed 349 and the program will return to the point of interruption 351.

For an Aerobic EDB, the program will extract and display the Calories value 348. The program next allows the input of a new calories setting 350. The program continues at Marker B for ENTER key processing 352. When successfully concluded, the program will return to the point of interruption 353

Figure 16:
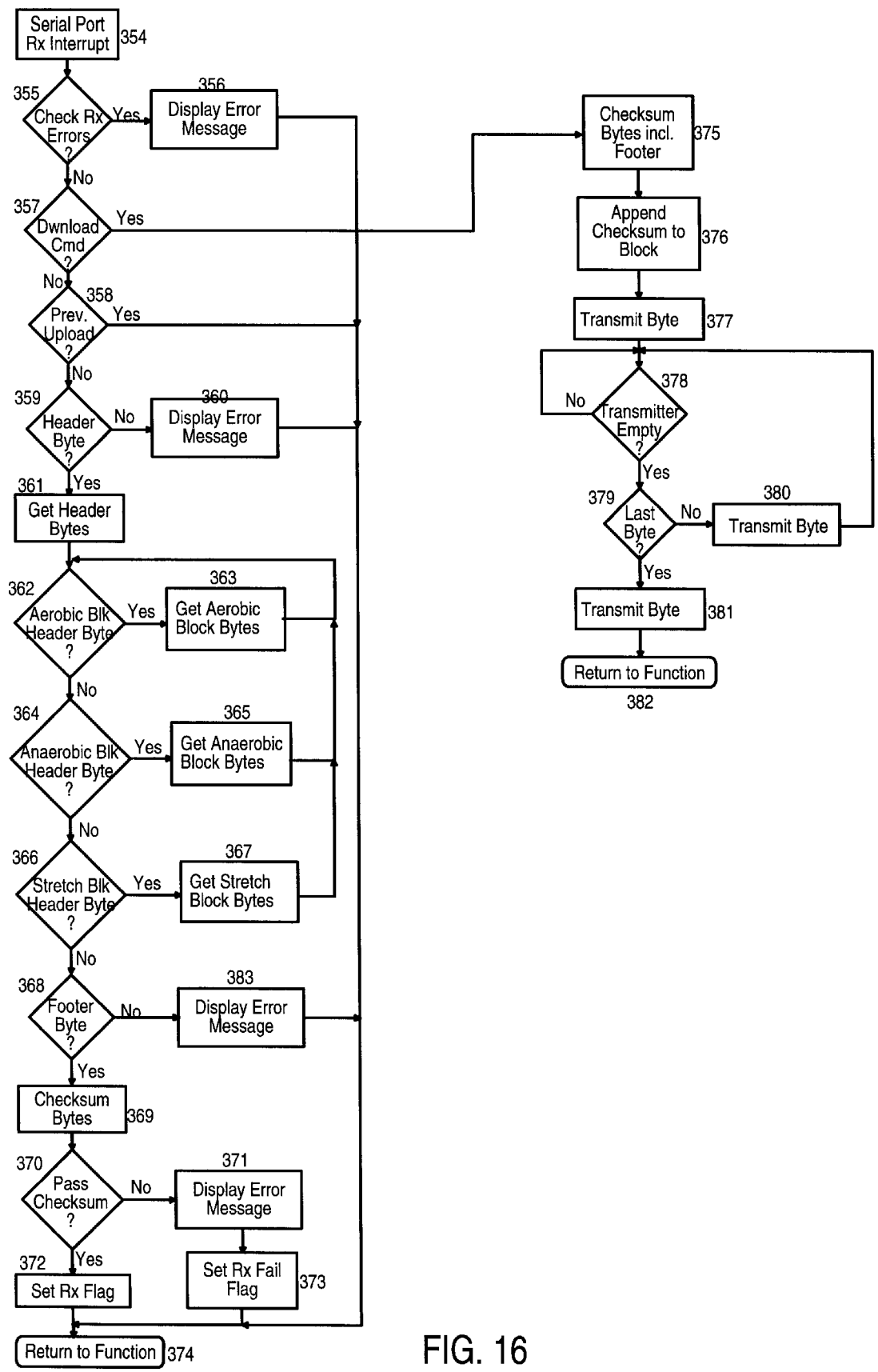
FIG. 16 Shows a flow diagram of both Version A & B DTA firmware Serial Port Interrupt Routine sequences.

FIG. 16 Shows a flow diagram of both Version A & B DTA firmware Serial Port Interrupt Routine sequences.

The microcontroller's serial communications interface will generate an interrupt when a byte has been received 354. The interrupt routine will check to see if any receive errors were accrued 355. If so a special error message is displayed 356 and the program returns to the point of interruption 374.

If there are no errors, the byte is examined to see if it is a download command 357. If so the processing continues to process a download starting at 375. If not then the program checks to see if a previous upload has been received 358. If so, the interrupt routine is exited and the program returns to the point of interruption 374.

If no previous upload has been received, the program checks to see if the byte was a valid master header byte 359. If not then display special error message and the program returns to the point of interruption 374.

If a valid master header byte is detected, the remaining header block bytes are received and put into a buffer in RAM 361. After the header bytes have been received, the program will examine the next byte received and check if it is an Aerobic EDB header byte 362, if so the program will determine how many more bytes in the block, receive them, and store in RAM buffer 363.

If the EDB header byte was not Aerobic, the program checks to see if it was Anaerobic 364. if so the program will determine how many more bytes in the block, receive them, and store in RAM buffer 365.

If the EDB header byte was not Anaerobic, the program checks to see if it was Stretch 366. if so the program will determine how many more bytes in the block, receive them, and store in RAM buffer 367.

If the EDB header byte was not Stretch, the program checks to see if it was the Footer byte 368. if not the program will display a special error message 383 and returns to the point of interruption 374.

If the Footer byte is detected, the entire received buffer is modulo-256 checksummed 369. The result is compared to the embedded checksum value that followed the Footer byte in the block 370. If there was a mismatch, the program displays a special error message 371, sets a failure flag 373 and returns to the point of interruption 374. If the checksum test passes, the received valid flag is set 372 and the program returns to the point of interruption 374.

For the download command received case, the entire exercise routine block (from master header byte to Footer byte) is modulo-256 checksummed 375 and the result appended as the last byte in the block 376. The entire block is then transmitted out the serial interface one byte at a time 377. When the transmitter is detected as empty 378, the next byte is transmitted. When the last byte has been detected 379, the byte is transmitted 381 and the program returns to the point of interruption 382.

Figure 17:
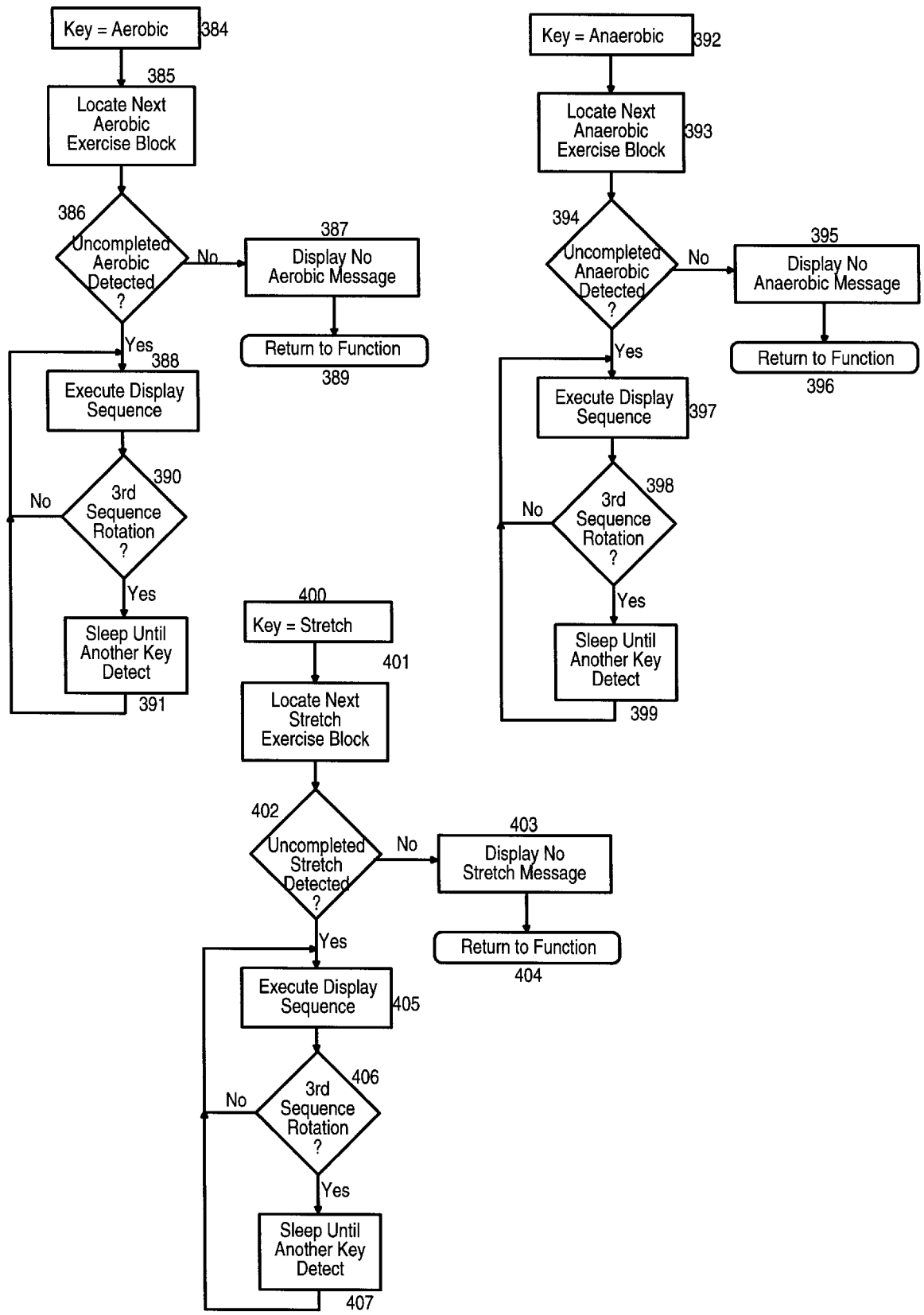
FIG. 17 Shows a flow diagram of the Version-B DTA firmware AEROBIC, ANAEROBIC, and STRETCH keypad key activation sequences FIG. 18 Shows a flow diagram of the Version-B DTA firmware START/STOP and LAP/RESET keypad key activation sequences FIG. 19 Shows a flow diagram of the Version-B DTA firmware PLATES/LBS, REPS., SETS, DISTANCE, DURATION, SPEED, INCLINE, LEVEL, and CALORIES keypad key activation sequences FIG. 20 Shows a connectivity diagram for the application software program depicting screen and file relationships FIG. 21 Shows a detail of the Flush Mounted Self Adjusting Clip on the Version-B DTA units.

FIG. 17 Shows a flow diagram of the Version-B DTA AEROBIC, ANAEROBIC, and STRETCH keypad key activation sequences The Version-B DTA unit expands the Version-A DTA's GROUP key into the three separate exercise groups selection buttons; Aerobic, Anaerobic, and Stretch If the AEROBIC key is detected 384, the program will start at the first EDB and searches for the first uncompleted Aerobic exercise 385. If no uncompleted aerobic exercise is found 386, a special error message is displayed 387 and the program returns to the point of interruption 389.

If an uncompleted Aerobic exercise is found, the exercise display sequence routine 388 will parse out the elements of the EDB and display them on the LCD. If the exercise parameter is 0, its display may be omitted. The display sequence is as follows:

AEROBIC Excerises:

Name of Exercise
delay 3 seconds
Mechanically/Ergonomically Settings

| AEROBIC Excerises: |
| --- |
| delay 3 seconds |
| Duration Setting (if not 0) |
| delay 3 seconds |
| Distance Setting (if not 0) |
| delay 3 seconds |
| Speed Setting (if not 0) |
| delay 3 seconds |
| Intensity Setting (if not 0) |
| delay 3 seconds |
| Calorie Setting (if not 0) |
| delay 3 seconds |
| Incline Setting (if not 0) |
| delay 3 seconds |
| Level Setting (if not 0) |
| delay 3 seconds |

The sequence is repeated three times 390 after which the microprocessor will enter its low power sleep mode 391 until a keypad key is activated and the resultant activation interrupt is detected. The sequence will then restart at the top.

If the ANAEROBIC key is detected 392, the program will start at the first EDB and searches for the first uncompleted Anaerobic exercise 393. If no uncompleted anaerobic exercise is found 394, a special error message is displayed 395 and the program returns to the point of interruption 396.

If an uncompleted Anaerobic exercise is found, the exercise display sequence routine 397 will parse out the elements of the exercise description block and display them on the LCD. If the exercise parameter is 0, its display may be omitted. The display sequence is as follows:

| ANAEROBIC Exercises: |
| --- |
| Name of Exercise |
| delay 3 seconds |
| Mechanical/Ergonomically Settings |
| delay 3 seconds |
| Pounds/Plates Setting (if not 0) |
| delay 3 seconds |
| Repetitions Setting (if not 0) |
| delay 3 seconds |
| Sets Setting (if not 0) |
| delay 3 seconds |
| Duration Setting (if not 0) |
| delay 3 seconds |

The sequence is repeated three times 398 after which the microprocessor will enter its low power sleep mode 399 until a keypad key is activated and the resultant activation interrupt is detected. The sequence will then restart at the top.

If the STRETCH key is detected 400, the program will start at the first EDB and searches for the first uncompleted Stretch exercise 401. If no uncompleted stretch exercise is found 402, a special error message is displayed 403 and the program returns to the point of interruption 404.

If an uncompleted Stretch exercise is found, the exercise display sequence routine 405 will parse out the elements of the exercise description block and display them on the LCD. If the exercise parameter is 0, its display may be omitted. The display sequence is as follows:

| STRETCH Exercises: |
| --- |
| Name of Exercise |
| delay 3 seconds |
| Repetitions Setting (if not 0) |
| delay 3 seconds |
| Sets Setting (if not 0) |
| delay 3 seconds |

The sequence is repeated three times 406 after which the microprocessor will enter its low power sleep mode 407 until a keypad key is activated and the resultant activation interrupt is detected. The sequence will then restart at the top.

Figure 18:
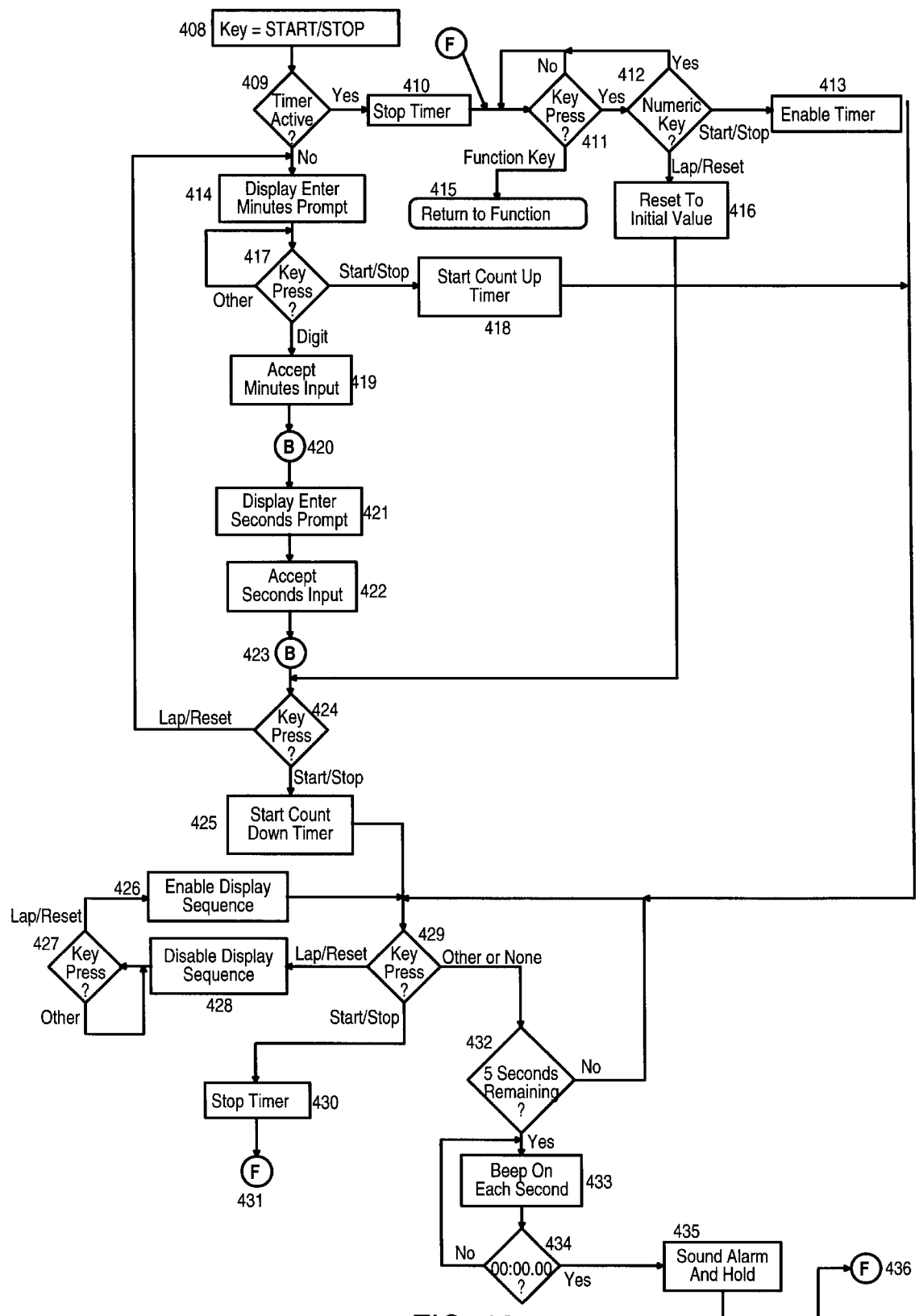

FIG. 18 Shows a flow diagram of the Version-B DTA firmware stopwatch START/STOP and LAP/RESET key activation sequences If the START/STOP key is detected 408, the program will first determine if the timer is already running 409. If so, the timer is stopped 410 and the program will wait for another key activation 411. If the next detected key activation is a function key, the program returns to the point of interruption 415. If the next detected key activation is a numeric key 412, the key is ignored. If the next key detected is the LAP/RESET key, the timer is reset to its initial value 416 depending if it was in count down or count up mode. If the next key detected is the START/STOP, the timer is re-enabled 413 and the timer continues.

If the timer was not running initially when the START/STOP key is detected, the "Set Minutes" prompt 414 is displayed. The program waits for another key activation 417. If the START/STOP key is activated, the timer goes into its count up mode 418. If a digit is pressed, the program will accept a minutes setting 419. Any other key will be ignored.

Following Inputting minutes, the program continue at Marker B for ENTER key processing 420. Upon completion of entering a valid minutes setting, the program will prompt for seconds input 421 & 422. The program continues at Marker B for ENTER key processing 423. Upon completion of entering a valid seconds setting, the program waits for another key activation 424. If the LAP/RESET key is detected, the program resets the timer function and redisplays the "Set Minutes" prompt 414. If the START/STOP key is detected, the count-down timer mode is started 425 and the program displays the elapsed time while waiting for time-out or another key activation 429.

If the LAP/RESET key is activated, the program will disable the display function while maintaining the timer 428. The program will wait for the LAP/RESET key activated again 427. When detected, the display function is re-enabled 426.

If the START/STOP key is activated, the timer is stopped 430 and processing continues at Marker F 431.

Any other key will be ignored. The program will monitor the count in count-down mode looking for the last 5-seconds remaining 432. When detected, the alarm will beep on each second 433. When the timer expires 434, the alarm will sound several beeps and the timer is stopped 435. Processing then continues at Marker F 436.

Figure 19:
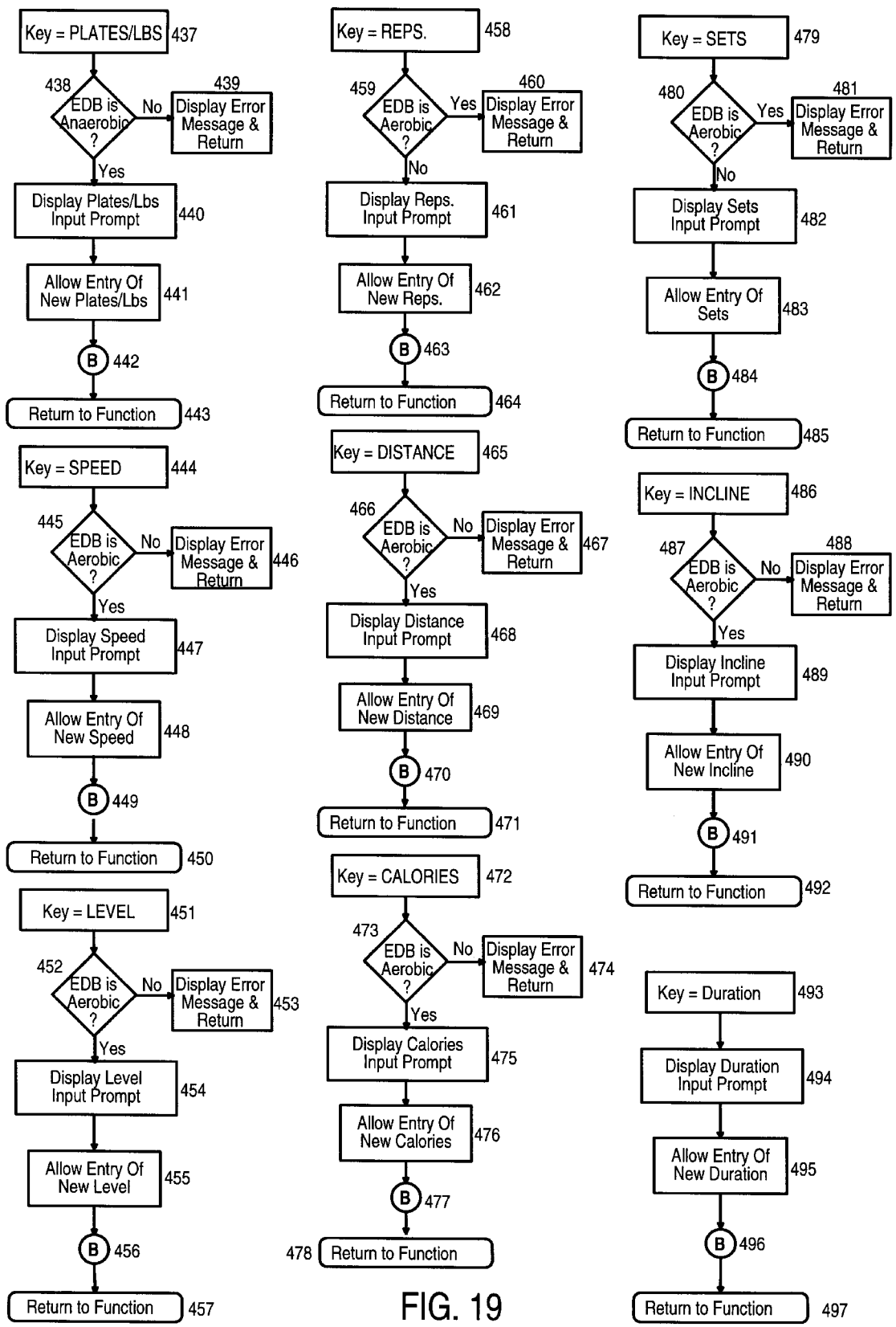

FIG. 19 Shows a flow diagram of the Version-B DTA firmware PLATES/LBS, REPS., SETS, DISTANCE, DURATION, SPEED, INCLINE, LEVEL, and CALORIES keypad key activation sequences On the Version-B DTA, each function has an individual key although the actual signal to the microprocessor may be shared. The context in which it is activated will distinguish the desired function.

If the PLATES/LBS key is detected 437, the program checks to see if the EDB is Anaerobic 438, if not then a special error message is displayed and the program resumes at the point of interruption 439. If so, the program will extract the current plates/lbs value and display it 440. The program will now accept a new value 441 and then continue at Marker B for ENTER key processing 442. Upon completing a valid input, the program resumes at the point of interruption 442.

If the REPS. key is detected 458, the program checks to see if the EDB is Aerobic 459, if so then a special error message is displayed and the program resumes at the point of interruption 460. If not, the program will extract the current repetitions value and display it 461. The program will now accept a new value 462 and then continue at Marker B for ENTER key processing 443. Upon completing a valid input, the program resumes at the point of interruption 464.

If the SETS key is detected 479, the program checks to see if the EDB is Aerobic 480, if so then a special error message is displayed and the program resumes at the point of interruption 481. If not, the program will extract the current sets value and display it 482. The program will now accept a new value 483 and then continue at Marker B for ENTER key processing 484. Upon completing a valid input, the program resumes at the point of interruption 485.

If the SPEED. key is detected 444, the program checks to see if the EDB is Aerobic 445, if not then a special error message is displayed and the program resumes at the point of interruption 446. If so, the program will extract the current speed value and display it 447. The program will now accept a new value 448 and then continue at Marker B for ENTER key processing 449. Upon completing a valid input, the program resumes at the point of interruption 450.

If the DISTANCE key is detected 465, the program checks to see if the EDB is Aerobic 466, if not then a special error message is displayed and the program resumes at the point of interruption 467. If so, the program will extract the current speed value and display it 468. The program will now accept a new value 469 and then continue processing at Marker B 470. Upon completing a valid input, the program resumes at the point of interruption 471.

If the INCLINE key is detected 486, the program checks to see if the EDB is Aerobic 487, if not then a special error message is displayed and the program resumes at the point of interruption 488. If so, the program will extract the current incline value and display it 489. The program will now accept a new value 490 and then continue at Marker B for ENTER key processing 491. Upon completing a valid input, the program resumes at the point of interruption 492.

If the LEVEL key is detected 451, the program checks to see if the EDB is Aerobic 452, if not then a special error message is displayed and the program resumes at the point of interruption 453. If so, the program will extract the current level value and display it 454. The program will now accept a new value 455 and then continue at Marker B for ENTER key processing 456. Upon completing a valid input, the program resumes at the point of interruption 457.

If the CALORIES key is detected 472, the program checks to see if the EDB is Aerobic 473, if not then a special error message is displayed and the program resumes at the point of interruption 474. If so, the program will extract the current calories value and display it 475. The program will now accept a new value 476 and then continue at Marker B for ENTER key processing 477. Upon completing a valid input, the program resumes at the point of interruption 478.

If the DURATION key is detected 493, the program will extract the current duration value and display it 494. The program will now accept a new value 495 and then continue at Marker B for ENTER key processing 496. Upon completing a valid input, the program resumes at the point of interruption 497.

F. Application Software Description

The application software, henceforth referred to as Physicalc, is described below with reference to the drawings specified. Sample screens from the program are included for clarity.

Figure 20:
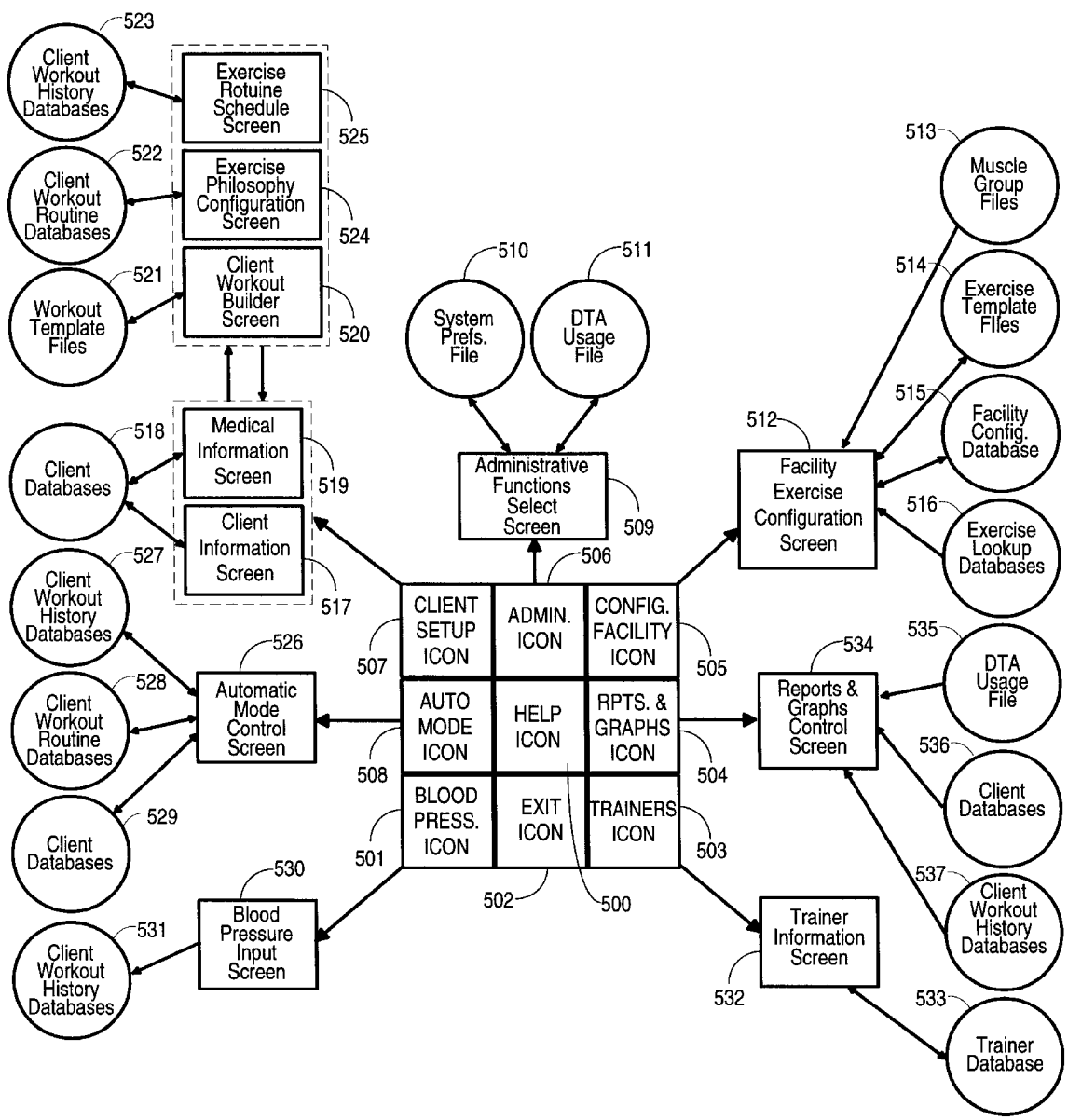

FIG. 20 Shows a connectivity diagram for the application software program depicting I/O screens and database file relationships.

Following is a function by function description of the Physicalc software including a representative I/O screens and descriptions of the related database files associated with the function.

The main menu for the Physicalc software program is composed of nine graphical icons 500, 501, 502, 503, 504, 505, 506, 507, & 508. By selecting the icon using a cursor pointing device (i.e. mouse) or keyboard (Tab and Enter keys), the underlying function is accessed. An associated menu bar is also available from which the user can select the function.

Figure 25:
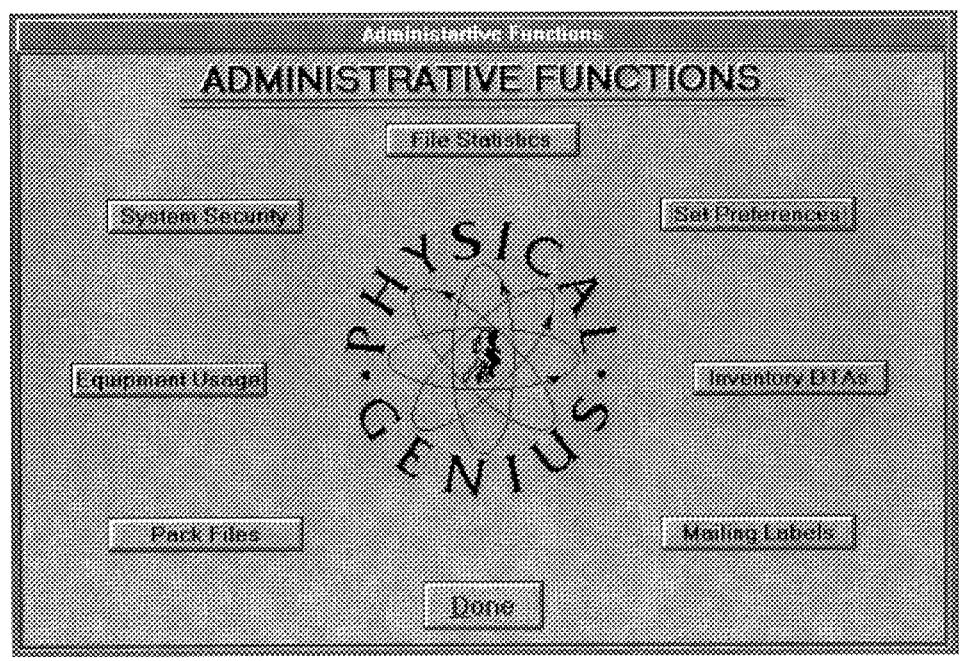
FIG. 25 Administrative Functions Screen representation.

When the user selects the Administration icon 506, the Administrative Functions capabilities of the software are accessed. A graphical interface screen 509 is presented to the user. See FIG. 25 for screen representation.

By selecting a function presented on the screen or through selection from an associated menu bar, the user can perform one of the following tasks:

1. Examine pertinent file statistics.
2. Set the system access security for all users.
3. Chart the facility's exercise equipment usage.
4. Pack (remove deleted records) the database files.
5. Set system wide preferences.
6. Inventory DTA units.
7. Create mailing lists and labels for the clients stored in the system.

Connected to this function are two database files. The first file is called prefs.dbf 510 and is a small database file used to hold system wide preference parameters. A description of a data stored in the preference table includes the following:

1. A list of membership type categories.
2. A list of Trainer classification types.
3. The hours of operation for the facility.
4. The host PC communications port the DTA Programming Stand is connected to.

The other database file is called dta.dbf 511. This will hold the status of Digital Training Assistant units programmed by Physicalc during the current session. It is used in the Inventory DTA function in both the Administrative functions and Reports & Graphs functions of the program. A description of the records included in the database includes:

1. The client's membership number.
2. The date the DTA was uploaded.
3. The date the DTA was downloaded.

Figure 26:
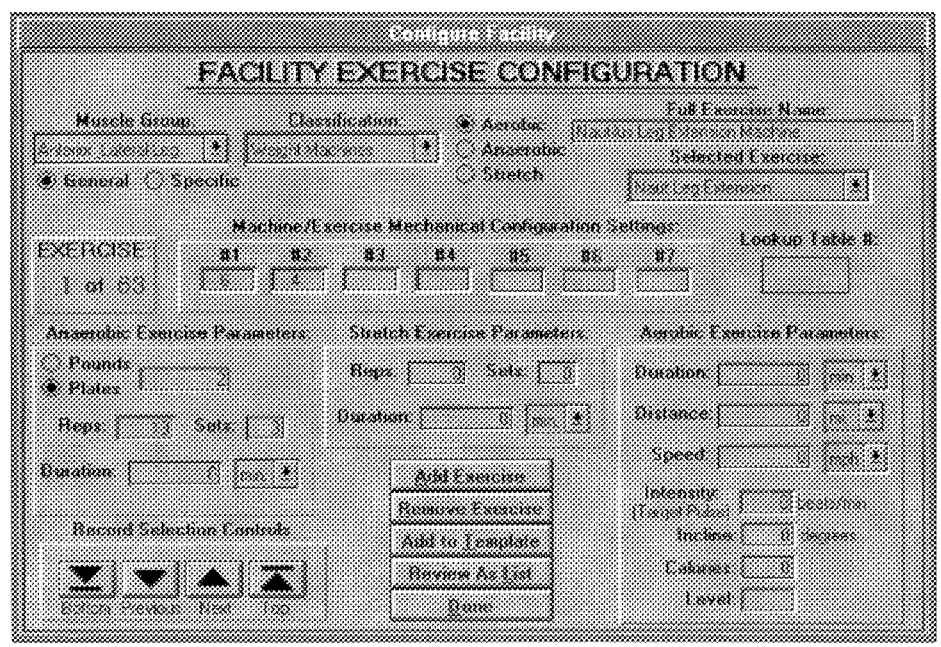
FIG. 26 Facility Exercise Configuration Screen representation.

When the user selects the Configure Facility icon 505, the Facility Configuration function of the software is activated. A graphical interface screen 512 is used to input and display data records from the facility configuration database. Refer to FIG. 26 for screen representation.

This function is used to create a database of exercises and exercise equipment that are available at the facility in which the system is installed. An additional capability is the ability to create a series of template files containing a subset of exercises from the facility's master database. These templates can then be used to quickly construct exercise routines with pre-defined equipment lists.

Connected to this function are four database files. The facility configuration database file called facility.dbf 515 will contain records representing all the exercise equipment available at the facility where the Physicalc program is to be used. The user will use the Facility Exercise Configuration screen and associated menu bar to build the file's records. A complete description of an exercise includes the following:

1. Muscle Group being worked
2. Classification (free weights, nautilus machine, etc.)
3. Exercise Group (Aerobic, Anaerobic, or Stretch)
4. Exercise Name (50 characters maximum)
5. Name as Displayed by DTA (16 characters maximum)
6. Lookup Table # (if name comes from the hardcoded lookup table)

Exercises that are specified as AEROBIC will have the additional following information:

1. Up to seven (7) Mechanical settings for equipment setup (specified as a letter or number)
2. Duration (specified as either seconds, minutes, or hours)
3. Level Setting (either a letter or number)
4. Speed Setting (specified as either mph, kph, fpm, or mpm)
5. Calories Setting
6. Distance Setting (specified as either kilometers, meters, miles, or feet)
7. Incline (specified as degrees, used on treadmills)
8. Intensity Setting (target pulse rate)

Exercises that are specified as ANAEROBIC will have the additional following information:

1. Up to seven (7) Mechanical settings for equipment setup (specified as a letter or number)
2. Pounds/Plates Setting (pounds for free weights and plates for weight machines)
3. Repetitions setting
4. Sets setting (number of groups of repetitions)
5. Duration (specified as either seconds, minutes, or hours)

Exercises that are specified as STRETCH will have the additional following information:

1. Repetitions setting
2. Sets setting (number of groups of repetitions)
3. Duration (specified as either seconds, minutes, or hours)

A supplemental read-only table called lookups.dbf 516, contains a list of exercise names and associated code numbers. This table mimics the table of hard-coded exercise names found in the Digital Training Assistant (DTA) handheld computer's firmware program. It will be used to substitute a number in place of a 16 character exercise name when programming the DTA units. This saves considerable memory space in the DTA.

As mentioned earlier, as a record is built, it may be added to Exercise Template files 514 with the unique naming convention:

xxxxxtpl.dbf (where xxxxx=first 5 characters specified by user)

The user may choose to add the current completed exercise record to a specified template table file using the Add to Template screen push button or Template→Add to Template menu option The end result of adding to the template is a custom list of exercises that the user can then copy to a client's workout routine as a skeleton to build upon. A Template file shares the same structure as the facility.dbf database file.

Figure 27:
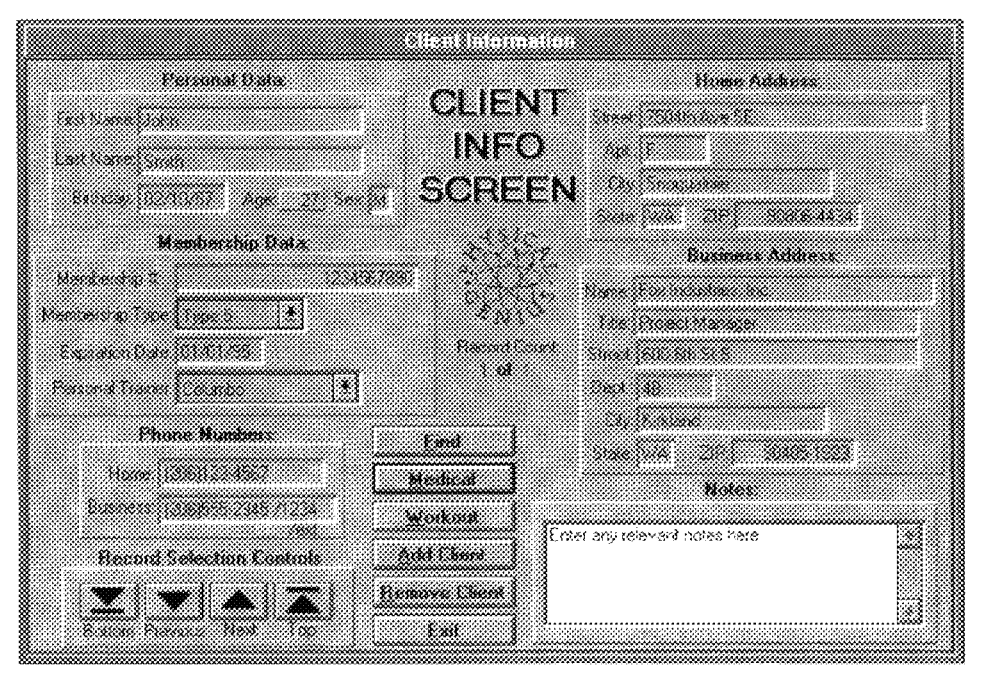

The Muscle Group Files 513 are composed of two read-only database files. The genmus.dbf database file is a read-only list of muscle groups arranged by major body part then alphabetically by major muscle group in that part of the body. The specmus.dbf database file is a read-only list of muscle groups arranged by major body part then alphabetically by specific muscle group in that part of the body When the Client Setup icon 507 is selected, the client Information Setup function is activated. This function allows the user to input and display demographic and medical data into a client database file. Activation of the function presents the Client Information Screen 517. Refer to FIG. 27 for screen representation.

This screen is one of two used to input and display the demographic, membership and medical data elements of the selected client database. There are controls for moving around in the database as well as search, remove, and adding capabilities. Additional controls provide access to the Medical Info Screen as well as accessing the Workout Builder utility.

Connected to this screen is a single database file called client.dbf 518. This database will contain records representing demographic and medical information from a set of clients utilizing the Physicalc system. The user will use the Client Info Screen 517, Medical Info Screen 519 and associated menus to build records. A complete description of a client database record includes the following:

Personal Data:
1. Full Name
2. Date of Birth
3. Age (computed to current date)
4. Sex Home Address:
1. Street Address
2. Apartment/Unit Number
3. City
4. State
5. ZIP code (w/4-digit extension)

Business Information:
1. Business Name
2. Job Title
3. Street Address
4. Department/MS
5. City
6. State
7. ZIP code (w/4-digit extension)

Figure 28:
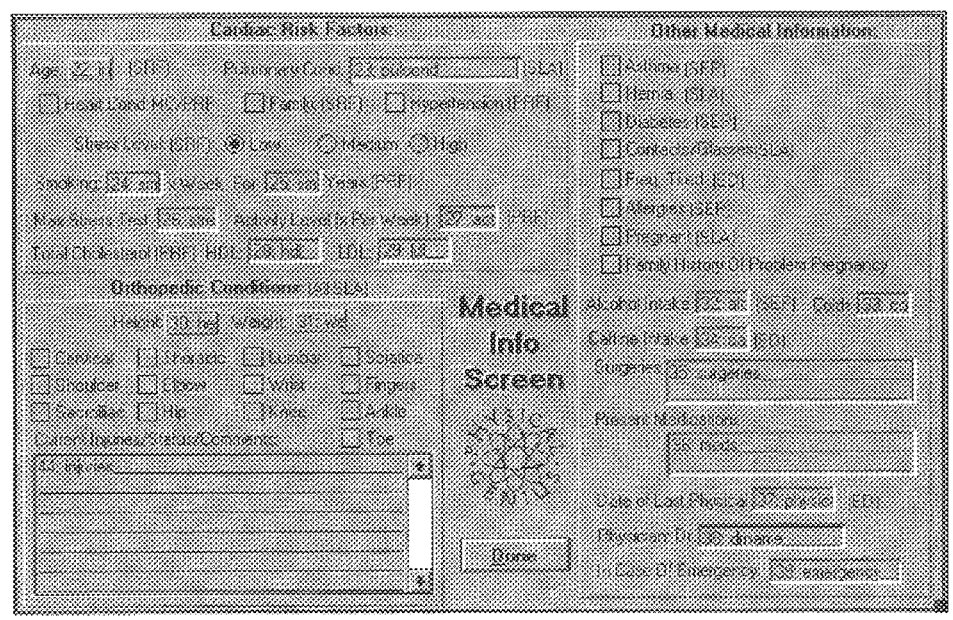
FIG. 28 Medical Information Screen representation.

Membership Data:
1. Membership #
2. Membership Type
3. Expiration Date
4. Personal Trainer's Name Phone Numbers:
1. Home Phone Number
2. Business Phone Number Relevant Notes Access to the Medical Information Screen 519 is through the Client Information Screen Medical push-button or menu selection. Refer to FIG. 28 for screen representation.

This screen is used to input and display medical oriented data elements of the client database file. The following client.dbf database file record data items are accessed through the Medical Information screen:

Cardiac Risk Factors:
1. Age (computed to the current date)
2. Name of pulmonary condition (if any)
3. Existence of a heart condition
4. Existence of a heart conditions in the family
5. Existence of a Hypertension
6. Level of daily stress (low, medium, or high)
7. Smoking habits (how much and for how long)
8. Maximum Stress Test score
9. Physical activity level
10. Cholesterol HDL & LDL values Other Medical Information:
1. Existence of Asthma
2. Existence of any Hernia
3. Use of contact lenses or Glasses
4. Existence of Diabetes
5. History of being frequently tired
6. Existence of Allergies
7. Current Pregnancy
8. Family history of problem pregnancies
9. Alcohol Intake (drinks per week)
10. Number of common colds per year
11. Caffeine intake (cups or can per day)
12. List of major surgeries
13. List of current medications
14. Date of last physical (by physician)
15. Physician's name
16. Physician's phone number (or other in case of emergency number)

Figure 29:
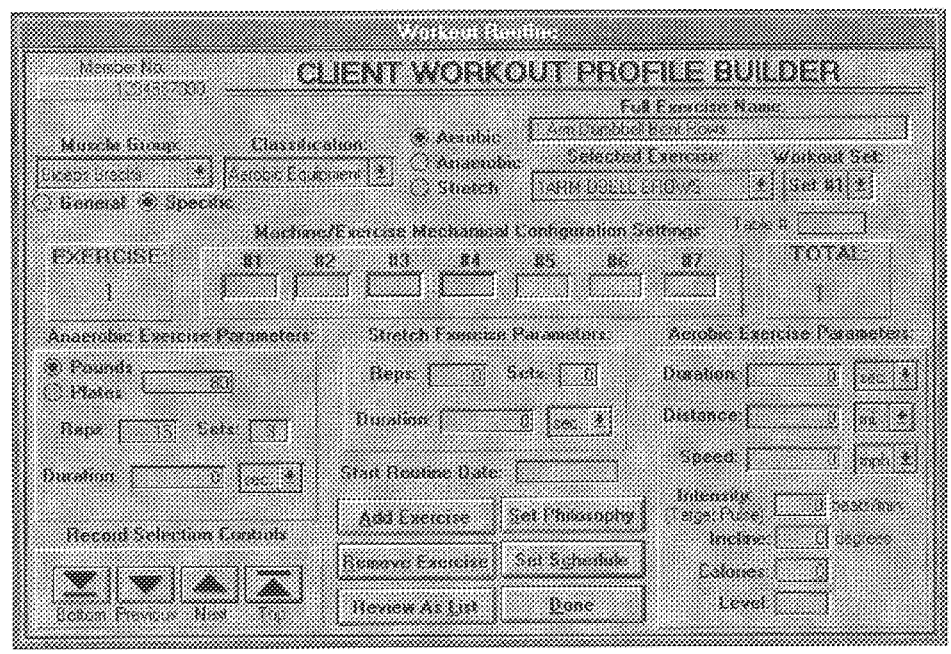
FIG. 29 Client Workout Profile Builder Screen representation.

Orthopedic Conditions:
1. client's height
2. client's weight
3. Existence of Cervical problems
4. Existence of Thoracic problems
5. Existence of Lumbar problems
6. Existence of Sciatica problems
7. Existence of Shoulder problems
8. Existence of Elbow problems
9. Existence of Wrist problems
10. Existence of Finger problems
11. Existence of Sacroiliac problems
12. Existence of Hip problems
13. Existence of Knee problems
14. Existence of Ankle problems
15. Existence of Toe problems
16. Description of injuries Each client entered into the system may have an associated fitness workout program designed for him/her. Connected to this screen are four database files. The Workout Builder function of the software is accessed from the Client Information Screen Workout push-button or menu selection. The Client Workout Profile Builder screen 520, is presented to assist the user in constructing a workout program for the currently selected client record in the client.dbf database file. Refer to FIG. 29 for screen representation.

The workout.dbf database file 521 is used as a template for creating individual Client Workout Routine 522 and Client Workout History 523 database files. In creating the individual client's workout routines, the structure from workout.dbf is copied to create the new Client Workout Routine file. A complete description of a workout routine includes the following:
1. Exercise Group (Aerobic, Anaerobic, or Stretch)
2. Machine/Exercise Mechanical Settings
3. Parametric Exercise Settings (not necessary all listed used per exercise)
   a. Pounds/Plates
   b. Repetitions
   c. Sets
   d. Duration
   e. Distance
   f. Speed
   g. Intensity
   h. Incline
   i. Calories
   j. Level
4. Exercise Philosophy
   a. When to increase parameter
   b. What parameter to increase
   c. By how much to increase parameter
   d. How to continue the increase parameter philosophy
   e. When to decrease parameter
   f. What parameter to decrease
   g. By how much to decrease parameter
   h. How to continue the decrease parameter philosophy
5. Routine Time Stamping
   a. Start of Routine Date
   b. Date of latest Completion
   c. Enable Days
   d. Set Number Designation The client Workout Routine file is uniquely named using the following formula:

$$xxxxyyyy.dbf$$

xxxx: first 4-letters of th client's last name taken from the currently selected record in the Client Database file last name (last_name) field. If the client's last name is shorter than four letters, the lower case letter 'x' is appended until four letters are created.

yyyy: last 4-digits of client's membership number taken from the currently selected record in the Client Database membership number (member_no) field. If the client's membership number is shorter than four digits, the number 9 is appended until four digits are created.

The Client Workout Routine database files 522, henceforth referred to as CWR, contains a single copy of the client's computed workout routine for the day it was requested. It will be used to create a new workout routine based upon past performance and special "philosophy" parameters entered using the Exercise Philosophy Configuration screen 524. The routine is then scheduled over a 7 day period using the Schedule Routine Screen 525.

The client may have up to 7 different workout routines designated as sets. The CWR file is grouped by set first and then sorted by exercise in the order they were input into the system.

The Client Workout History database files 523, henceforth referred to as CWH, are uniquely named using the follow formula:

$$xxxxyyyy.his$$

xxxx: first 4-letters of the client's last name taken from the currently selected record in the Client Database file last name (last name) field. If the client's last name is shorter than four letters, the lower case letter 'x' is appended until four letters are created.

yyyy: last 4-digits of client's membership number taken from the currently selected record in the Client Database membership number (member_no) field. If the client's membership number is shorter than four digits, the number 9 is appended until four digits are created.

Figure 30:
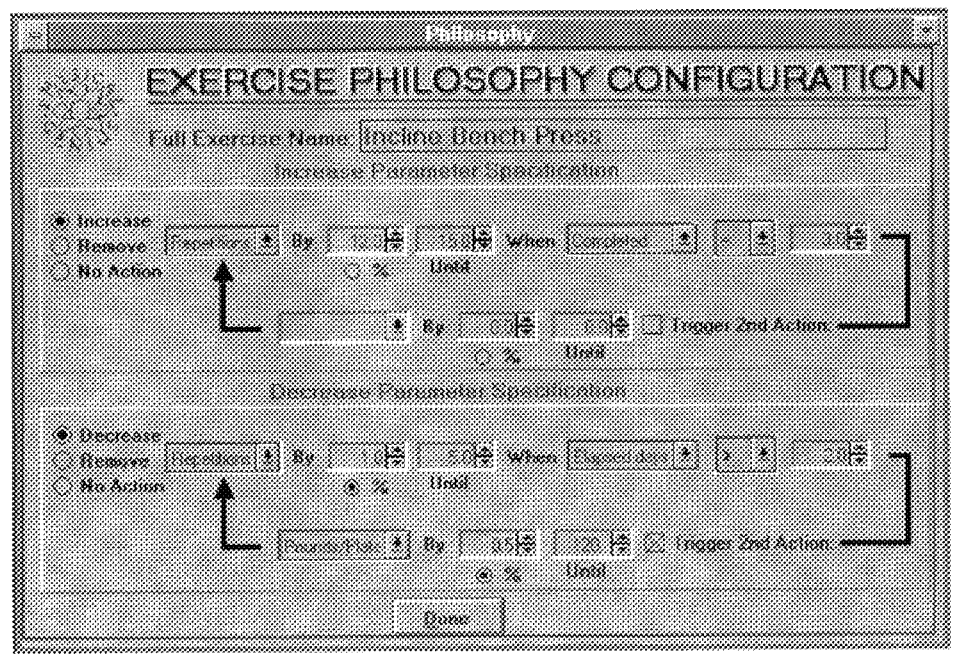
FIG. 30 Exercise Philosophy Configuration Screen representation.

The CWH contain a history of completed exercises. This file is composed of records representing exercises and associated performance parameters. Each record contains a date stamp allowing the Report & Graphs function to generate reports and graphs of client performance over a selected period of time. Following a workout session, the client's executed workout information data package is transferred from the DTA, modified (irrelevant fields removed, i.e. mechanical settings), date stamped, and appended to the client's CWH file. A complete description of a data stored in the records of a CWH file includes the following:
1. Full Exercise Name
2. DTA Exercise Name
3. Exercise Group (Aerobic, Anaerobic, or Stretch)
4. Parametric Exercise Settings (not necessary all listed used per exercise)
   a. Pounds/Plates
   b. Repetitions
   c. Sets
   d. Duration
   e. Distance
   f. Speed
   g. Intensity
   h. Incline
   i. Calories
   j. Level
5. Client's Weight
6. Client's Pulse
7. Client's Blood Pressure
8. Date of routine completion
9. Completed as Prescribed Flag The trainer supplements an exercise's description by adding a "Philosophy" to the exercise. The Philosophy describes the action to be performed on selected exercise parameters when the client performs (or not) the exercise in the specified fashion. Pushing the Set Philosophy screen push button activates the Exercise Philosophy Configuration screen 524 where the trainer can now assign his philosophy parameters to the exercise. Refer to FIG. 30 for screen representation.

The exercise can have two of its parameters increase and two of its parameters decrease automatically. Alternatively, the exercise can choose to automatically remove itself when a specific condition is met. One action for each function is designated as the primary action and the one action is the secondary action. Both functions require a "trigger event" to occur before the increment, decrement or removal can occur. This trigger event involves checking a selected parameter against a selected value using a logical type operator. When the trigger event evaluates as "True", the primary action occurs. A limit value is included to prevent the primary action from setting a parameter too high or too low. After the trigger event occurs, it is automatically reset with the new primary action parameter value as the base.

An optional 2nd Action may also occur when the trigger event occurs. A separate check box for both the Increase and Decrease functions is provided. A second set of parameter popup lists is used to set a secondary action. The secondary action will occur every time the trigger event occurs until its own selectable limit value is reached of the primary action's limit is reached, which ever comes first.

NOTE: Program code will prevent the user from setting the primary and secondary action to the same parameter The user specifies the parameter to be automatically modified. Next he chooses the numeric value to either add or subtract from the parameter. The user can chose a discrete value or a percentage of the current value with the % radio button. Next he selects a modification limit for the parameter. When the limit is attained, further modification is disabled. Next the trigger event is decided by selecting a different parameter or the additional options of elapsed days or completed as prescribed. Then the trigger parameter operator is selected from one of the following:

= Equal to

< Less than

<= Less than or equal to

> Greater than

>= Greater than or equal to != Not equal to

The comparison value is set next. The trigger event will be evaluated as either True or False. A True evaluation constitutes a trigger event. The user may for either case (increase or decrease) specify a second action to be performed. Checking the Trigger 2nd Action checkbox will enable a second different parameter to be augmented. The user must again select the parameter, the increment or decrement value or percentage and the limit for the parameter.

Every time Physicalc is requested to create a client's daily workout routine, the trigger event for each exercise record in the client's CWR 522 is check against the most recent corresponding exercise record stored in the client's CWH 523 file. If the trigger conditions are determined as being met, the action parameters in the CWR 522 record is modified according to the action specification. For the initial workout, the date stored in a special field is used to determine any elapsed days.

The primary and secondary actions may also be incremented or decremented as a percentage of the current value. Selection of the % radio button will activate this feature.

A removal of an exercise as the primary action is a single shot event and once triggered, it remains disabled until explicitly set by a new philosophy setting.

Figure 31:
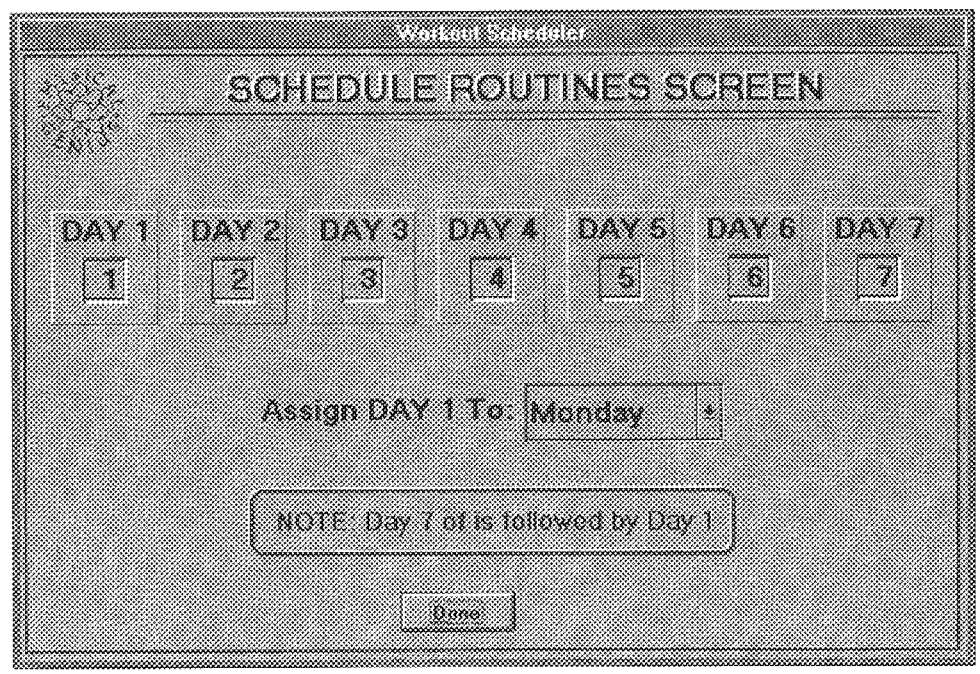
FIG. 31 Schedule Routines Screen representation.

Pushing the Set Schedule screen push button activates the Schedule Routine screen 525 where the trainer can now schedule exercise routines. Refer to FIG. 31 for screen representation.

Exercises can be grouped into 1 of 7 sets. This allows for the formulation of exercise set rotations found in many professional and competitive training regiments. A field in the records of the CWR database file called ex_set designates the set it belongs to. A further enhancement of this function is the ability to schedule these sets over an arbitrary 7-day period. The period is designated as DAY #1 through DAY #7 with DAY #1 being set to a specific day of the week (stored in its own field). You can now schedule any set to any day using the Schedule Routine Screen.

The trainer simply types a number under the Day X field to designate that on that day, the exercises with the matching set number are used to formulate the daily workout routine. The software calculates the day number using the current date and the value stored in the special field.

Program code for this screen will assign a bit in a byte for each day of the week (bit 1=Day 1, etc.). When the Done screen push button is pressed, the program will look at the exercise set field of ALL records in the selected CWR database file. It will set the bit in the record's field called week_sched corresponding to each day the exercise set was found in.

For example, an exercise record designated as belonging to Set #1 with the following Schedule Routine Screen settings will produce the resulting byte:

DAY 1 = Set 1  DAY 2 = Set 2  DAY 3 = Set 1  DAY 4 = Set 3
DAY 5 = Set 1  DAY 6 = Set 6  Day 7 = Set 2

| | 7 | 6 | 5 | 4 | 3 | 2 | 1 | 0 |
|---|---|---|---|---|---|---|---|---|
| week_sched | 0 | 0 | 1 | 0 | 1 | 0 | 1 | X |

The philosophy day counting rules count total elapsed days including those not designated for the particular set. The When parameter must account for this when setting Elapsed Days.

Figure 32:
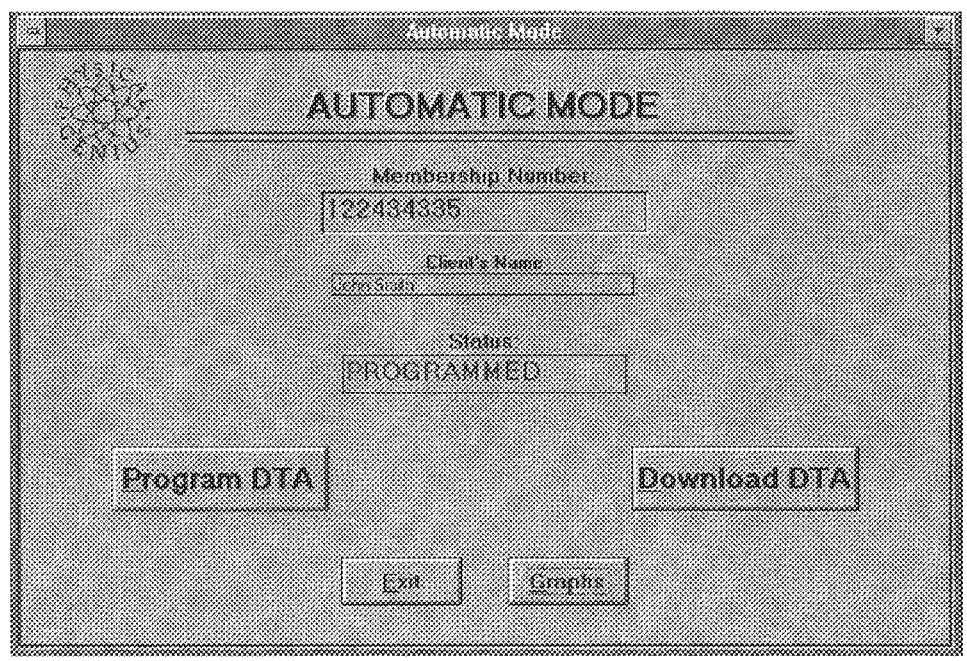
FIG. 32 Automatic Mode Screen representation.

If the user selects the Automatic Mode icon 508, the Automatic Mode function is executed. Refer to FIG. 32 for screen representation.

The Automatic Mode screen 526, is used to operate all the functions of the utility. When the client's membership card is read by the bar-code or magnetic strip reader it will present the membership number (10-digit max) to the Automatic Mode program code. The number will then be passed to the Program DTA Procedure and used to access the client's CWR 528 and CWH 527 to formulate the workout routine for the day. The workout routine is formatted into the upload exercise routine data package and transmitted to the DTA. Status of the operation is reflected in the Status field.

The user can also elect to receive data from a DTA (download). The function sends the appropriate command to the DTA to initiate downloading of its data. The data is parsed and reformatted to be incorporated back into the client's CWH file. Additional functionality allows the user to instantly perform some limited graphing functions for the client.

Figure 33:
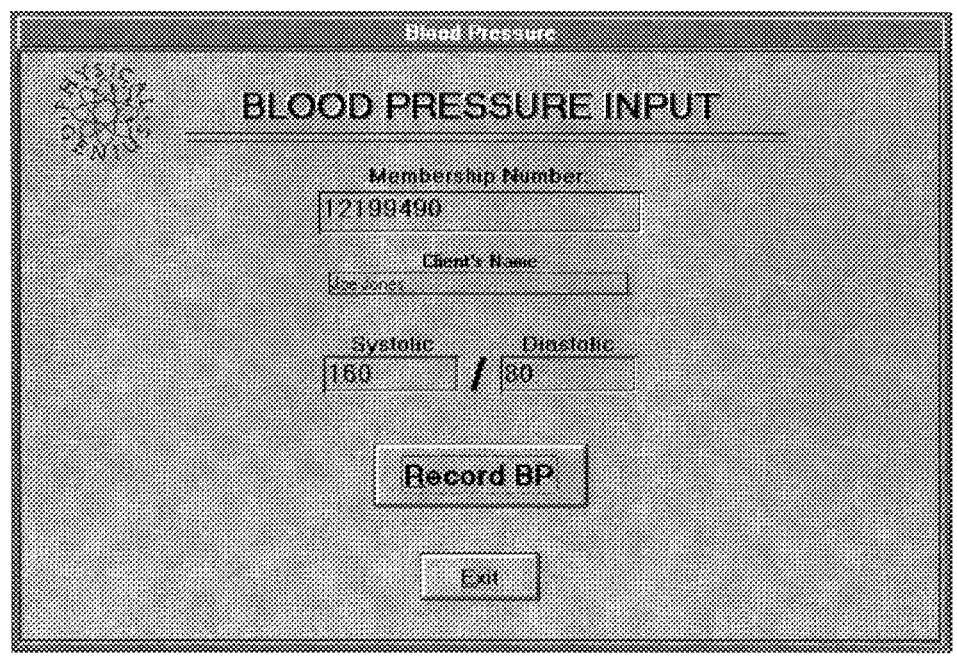
FIG. 33 Blood Pressure Screen representation.

If the user selects the Blood Pressure icon 501, the Blood Pressure Input mode function is executed. Refer to FIG. 33 for screen representation.

The Blood Pressure Input screen 530, is used to operate all the functions of the utility. When the client's membership card is read by the bar-code or strip reader it will present the membership number (10-digit max) to the Blood Pressure Input program code. The number will then be used to access the client's CWH 531 to allow fast input of the blood pressure systolic and diastolic readings to their appropriate fields in the database's records without having to manually open the file and insert the data.

Figure 34:
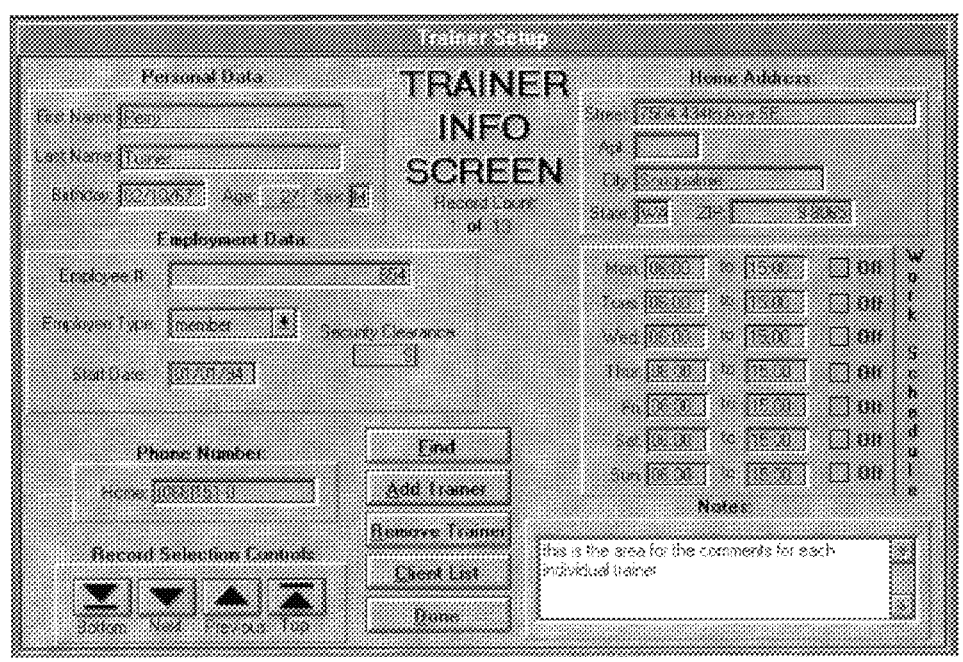
FIG. 34 Trainer Information Screen representation.

When the Trainers Setup icon 503 is selected, the Trainer Information Setup function is activated. This function allows the user to input and display demographic and employment data into the trainer database file 533. Activation of the function presents the Trainer Information Screen 532. Refer to FIG. 34 for screen representation.

This screen is used to input and display the demographic and employment data elements of the trainer database file 533. There are controls for moving around in the database as well as search, remove, and adding capabilities.

Figure 35:
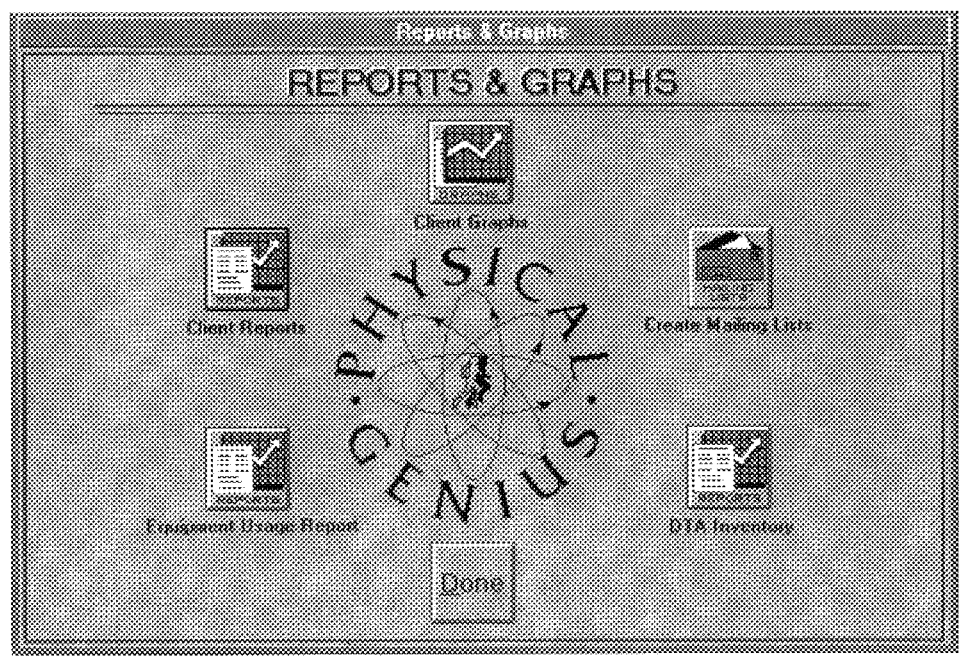
FIG. 35 Reports & Graphs Screen representation.

Connected to this screen is a single database file called trainer.dbf 533. This database will contain records representing demographic and employment information for a set of trainers utilizing the Physicalc system. The user will use the Trainer Info Screen 532, and associated menu to build records. A complete description of a Trainer database record includes the following:

Personal Data:
 1. Full Name
 2. Date of Birth
 3. Age (computed to current date)
 4. Sex Home Address:
 1. Street Address
 2. Apartment/Unit Number
 3. City
 4. State
 5. Zip Code (w/4-digit extension)
Employment Data:
 1. Employee #
 2. Employee Type
 3. Start Date
 4. Security Clearance Level
 5. Security Password
 6. Work Schedule
Phone Numbers
 1. Home Phone Number
Relevant Notes Selecting the Reports & Graphs icon 504 will activate the Report and Graph generating function. This function will gather data elements from selected records in the DTA usage file 535, the client database riles 536, and the Client Workout History database files 537. A single main screen is used to operate the function. Refer to FIG. 35 for screen representation. Through the screen's graphical icons, the following reports and graphs can be generated:

1. Graphing a client's weight over a specified time period.
 2. Graphing a client's pulse over a specified time period.
 3. Graphing a client's blood pressure over a specified time period.
 4. Graphing a selected exercise's parameter for a specific client over a specified time period.
 5. Create mailing lists and produce mailing labels for specified clients.
 6. Report a client's workout frequency.
 7. Report a selected client's demographic and medical history.
 8. Report on equipment usage over time by all clients.
 9. Report Digital Training Assistant usage.

Selecting the Help icon 500 will bring up the on-line help utility allowing the user to access text describing the functions and operations of the system. A context type help is available using the F1 key when the cursor is in a particular field of a screen. A topical help is also available using the Help icon 500 or the Help menu option.

The user with appropriate access clearance can also modify the text of the help screens to instruct the users on club practices and procedures.

Selecting the Exit icon 502 will exit the program back to the Windows™ program manager.

G. Digital Training Assistant Workout Routine
Program Creation Description

Central to the Physical application software are the software algorithms that create and decode exercise routine data packages. Collective they are referred to as the Program DTA procedure. Wherever necessary, the actual database file record field name is used for clarity.

The Program DTA procedure is divided into two sections. The first section involves compiling data from the Physicalc system's database files and transmitting it to a DTA (Transmit to DTA Subfunction). The second section involves the reverse process of taking data from a DTA and transferring it back into the system's database files (Receive From DTA Subfunction).

The following sections assume that the selected client's record in the currently selected Client Database file, the client's CWR, and CWH files are opened.

Transmit to DTA Subfunction

The DTA requires an upload of an exercise routine data package before use. The uploaded data consists of the exercises to be performed and the associated setup and performance parameters as determined by the trainer and the Physicalc program.

DTA Data Package Format

NOTE: All following data byte values are in their hexadecimal format as indicates by the leading 0x prefix to the number.

The DTA accepts a "data package" made up of embedded codes describing the client and the workout routine. The Program DTA Procedure will first construct the Header Block followed by the Exercise Description Blocks (EDBs) and terminated by a Footer code byte and Checksum Byte.

Header Block

The Header Block consists of 19 bytes. Any data not explicitly specified will be set to 0x0.

| Byte | Description |
|---|---|
| Byte 1 | HEADER COMMAND |
| Byte 2 | MEMBER # LSB |
| Byte 3 | MEMBER # |
| Byte 4 | MEMBER # |
| Byte 5 | MEMBER # MSB |
| Byte 6 | # OF CHARACTERS IN NAME |
| Byte 7 | 222 11111 |
| Byte 8 | 4 3333 22 |
| Byte 9 | 55555 4444 |
| Byte 10 | 77 66666 5 |
| Byte 11 | 88888 777 |
| Byte 12 | AAA 99999 |
| Byte 13 | C BBBBB AA |
| Byte 14 | DDDD CCCC |
| Byte 15 | FF EEEEE D |
| Byte 16 | GGGGG FFF |
| Byte 17 | WEIGHT LSB |
| Byte 18 | WEIGHT MSB |
| Byte 19 | PULSE |

Header Command (Byte 1)

The header command is a byte that tells the DTA to operate in Normal Mode or Learn Mode. In Learn Mode, the DTA user can change the mechanical/ergonomic settings. In Normal Mode these changes are locked out.

Normal Mode and Learn Mode are selectable in the Workout Builder menu DTA→Program DTA submenu options.

Normal Mode=0x00
Learn Mode=0x02

Membership Number Bytes (Bytes 2–5)

The member_no field of the client's client database (client.dbt) record in the currently selected client database file contains a 10-digit maximum integer number. This number is stored as four bytes in the header block with leading 0's as required. The Least Significant Byte (LSB) is stored in the Byte 2 location and the Most Significant Byte (MSB) in the Byte 5 location.

Client's Last Name Number of Characters Byte (Byte 6)

The client's last name is loaded into the DTA up to a maximum of 16 characters. The ASCII characters that makeup the last name are packed into the next 10 bytes to conserve memory in the DTA. The Number of Characters byte will tell the DTA software how many characters to extract from it's memory to display the user's last name. The number of actual characters is determined by counting characters in the last_name field of client's record in the currently selected client database file.

Client's Packed Last Name Bytes (Bytes 7–16)

As mentioned in the above section, the ASCII characters of the client's last name are packed into 10 bytes. The ASCII value of the character is trimmed to only 5 bits, the most significant three (3) bits will be added by the DTA firmware. This, again, is done to conserve space in the limited DTA memory.

The characters are represented as the numbers 1–9 and letters A–G in the following packing diagram. In the table below, the bits of the ASCII byte representing the first letter of the client's last name (all leading and trailing blanks removed) is represented by the number 1, the second character's bits by 2, and the last by G. Bits are ordered from right to left, least significant to most significant. The program code will reformat the client's last name character string taken from the last_name field of the client's record in the currently selected client database file.

| Byte | Bits |
|---|---|
| Byte 7 | 222 11111 |
| Byte 8 | 4 3333 22 |
| Byte 9 | 55555 4444 |
| Byte 10 | 77 66666 5 |
| Byte 11 | 88888 777 |
| Byte 12 | AAA 99999 |
| Byte 13 | C BBBBB AA |
| Byte 14 | DDDD CCCC |
| Byte 15 | FF EEEEE D |
| Byte 16 | GGGGG FFF |

NOTE: Any blank bytes or left over bits in the byte are set to 0

Client's Weight Bytes (Bytes 17–18)

The client's weight is stored in the CWH file's weight field. The program finds the most current record (looking at the ex_date field) and extracts the value of the weight field in the record. If no current record found then the value defaults to 0x0000.

The field is specified as three digits and a tenths of a pound digit. The program must reformat the data as follows. If there is a tenths digit other than 0 specified (i.e. 195.8 lbs. or 97.1 lbs.) the number is multiplied by 10 to remove the fraction and stored in two (2) bytes. The MSB byte's most significant bit must then be set as a flag to notify the DTA software to divide the number by 10 before displaying.

For Example:

weight field = 193.7

1) Multiply by 10    1937 = 0x791
2) Store in two bytes

| | 7 | 6 | 5 | 4 | 3 | 2 | 1 | 0 |
|---|---|---|---|---|---|---|---|---|
| MSB | 0 | 0 | 0 | 0 | 0 | 1 | 1 | 1 |

| | 7 | 6 | 5 | 4 | 3 | 2 | 1 | 0 |
|---|---|---|---|---|---|---|---|---|
| LSB | 1 | 0 | 0 | 1 | 0 | 0 | 0 | 1 |

3) Set the MSB's most significant bit

| | 7 | 6 | 5 | 4 | 3 | 2 | 1 | 0 |
|---|---|---|---|---|---|---|---|---|
| MSB | 1 | 0 | 0 | 0 | 0 | 1 | 1 | 1 |

Result = 0x8791
weight field = 125.0

1) Multiply by 10    1250 = 0x4E2
2) Store in two bytes

| | 7 | 6 | 5 | 4 | 3 | 2 | 1 | 0 |
|---|---|---|---|---|---|---|---|---|
| MSB | 0 | 0 | 0 | 0 | 0 | 1 | 0 | 0 |

-continued

| | 7 | 6 | 5 | 4 | 3 | 2 | 1 | 0 |
|---|---|---|---|---|---|---|---|---|
| LSB | 1 | 1 | 1 | 0 | 0 | 0 | 1 | 0 |

Result = 0x4E2

Client's Pulse (Byte 19)

The client's pulse is stored in the CWH file's pulse field. The program finds the most current record (looking at the ex_date field) and extracts the value of the pulse field in the record. If no current record found then the value defaults to 0x00. The pulse value is stored in Byte 19 of the Header Block.

Exercise Description Blocks (EDB)

Following the creation of the Header Block, the Program DTA Procedure—Transmit to DTA Subfunction will now construct EDBs incorporating Physicalc's exercise philosophy algorithms.

Exercise Philosophy Pre-Processing

The exercise routine for the specific day is extracted from the client's CWR file. Now the philosophy feature of Physicalc uses the last completed routine matching the exercise set number as derived from the processing depicted below. The process follows a step by step procedure as follows:

1. The program first looks at the current system date and determines what day of the week it is, Monday, Tuesday, etc.
2. The program then looks at the d_of_week field in the first record of the CWR file. By design, all records in the CWR will have the same value in the d_of_week field.
3. Using the d_of_week value the program computes what day of the week number it is for the particular client.
4. The program will now, starting at the first record, scan through each record in the CWR and look at the record's week_schd field byte. If a bit is set in the computed Day # bit position AND the ex_enable field is logical True, the exercise record is copied to a temporary cursor table (henceforth called Table A).
   NOTE: The program keeps track of where the record came from in the original CWR table. The modified records in Table A will eventually be copied back into their original positions in the CWR file.
   The resulting cursor table (Table A) contains all exercises and associated parameters that are supposed to be performed on this workout Day #
5. The ex_set field value from the first record in Table A is stored to a temporary variable named m.ex_set.
   NOTE: By design, all records for a specific Day # will belong to the same Exercise Set #. You can only schedule one Set # in any Day #.
6. The program now looks at the CWH file and starting at the last record and searching up to the top, the program compares the m.ex_set variable to each CWH record's ex_set field value.
   When the first match is made, the record number is noted (stored in a temporary variable, sendrec ) The search continues (going up towards the first record) until the first record found with a mismatch between m.ex_set and ex_set field value. The record number +1 is noted (stored in a temporary variable, startrec)
   NOTE: If no matches are found then this is the first time the routine (Set) is executed and the Table A records are used as is. Proceed to Step #35
   We now have the starting and ending record numbers (sendrec & startrec) for the latest completed exercise routine history matching the exercise Set number to be performed today. The records are checked for blank exercise field indicating blood pressure only records. Those records are skipped and the others are copied in ascending record order (normal) to a temporary cursor table opened in the next available word area (henceforth called Table B).

7. The program will now extract data from the following Table A's (currently pointed to) record fields and place the values into temporary variables

| Table | Field | Variable |
|---|---|---|
| Table A | inc_type | m.inc_type |
| Table A | inc_what | m.inc_what |
| Table A | inc_by | m.inc_by |
| Table A | inc_per | m.inc_per |
| Table A | inc_until | m.inc_until |
| Table A | inc_when | m.inc_when |
| Table A | inc_op | m.inc_op |
| Table A | inc_wby | m.inc_wby |
| Table A | inc_trig | m.inc_trig |
| Table A | inc_2what | m.inc_2what |
| Table A | inc_2by | m.inc_2by |
| Table A | inc_2per | m.inc_2per |
| Table A | inc_2until | m.inc_2until |
| Table A | dec_type | m.dec_type |
| Table A | dec_what | m.dec_what |
| Table A | dec_by | m.dec_by |
| Table A | dec_per | m.dec_per |
| Table A | dec_until | m.dec_until |
| Table A | dec_when | m.dec_when |
| Table A | dec_op | m.dec_op |
| Table A | dec_wby | m.dec_wby |
| Table A | dec_trig | m.dec_trig |
| Table A | dec_2what | m.dec_2what |
| Table A | dec_2by | m.dec_2by |
| Table A | dec_2per | m.dec_2per |
| Table A | dec_2until | m.dec_2until |
| Table A | ex_set | m.ex_set |

Now examine the Increase Parameter philosophy as follows

8. The program then examines the m.inc_type variable and if=3, no action is performed and the program advances to Step #21. If other than 3, the processing continues 9. The next action is to examine the parameter name stored in the m.inc_when variable. The following table equates the numeric code in the m.inc_when variable with the Table B field to examine or special action to perform:

| Numeric Code | Test Parameter | Table B field or Action |
|---|---|---|
| 1 | Duration | duration |
| 2 | Distance | distance |
| 3 | Speed | speed |
| 4 | Intensity | intensity |
| 5 | Incline | incline |
| 6 | Calories | calories |
| 7 | Level | level |
| 8 | Elasped Days[1] | Compute Elasped Days |
| 9 | Completed[2] | Compute Completed |

[1]The Elasped Days test parameter is computed by looking at the ex_date field in the Table B record and subtracting from the current date.

-continued

| Numeric Code | Test Parameter | Table B field or Action |
| --- | --- | --- |

[2]The Completed test parameter is computed by examining the completed field in the Table B's record. If the field contains a logical True, then the program will search backwards in the CWH (for a date before the current ex_date value in Table B) for a record matching the exercise and ex_set fields from Table A. The program will count how many consecutive record matches have a logical True in their completed filed. The counting stops as soon as a matching record has a logical False in the field. This number then represents the number of consecutively completed (without modification) prescribed exercises and becomes the completed count. If the current record completed field in Table B is logical false, the completed count is set to 0.

The data from the indicated Table B field or Action is stored in the temporary variable, lookat.

10. The program now examines the operator action stored in the m.inc_op variable. Using the decoded action:

| Symbol | Code # | Function |
| --- | --- | --- |
| > | 1 | Greater Than |
| < | 2 | Less Than |
| = | 3 | Equal To |
| >= | 4 | Greater or Equal To |
| <= | 5 | Less or Equal To |
| != | 6 | Not Equal |

The program evaluates the operand variable lookat and the test value in m.inc_wby.
NOTE: The numeric value in m.inc_wby can be used directly without moving to another variable.

11. If the evaluation is false (i.e. 100>120) The program aborts the current processing and continues at Step #21.
If the evaluation is True (i.e. 120>100) the processing continues.
Have now established an active Increase trigger condition 12. If the value of m.inc_type=2 then the ex_enable field of the TABLE A's record is set to logical false. The program jumps to Step #21.
If the value of m.inc_type=1 the program will extract the data stored in the Table A field named by the m.inc_what variable and store the data it in a temporary variable, incoperand.

13. The logical value of the m.inc_per variable determines if we increase by a percentage or discrete value.
If it is logical True, the program computes what m.inc_by percent of incoperand is and then adds that result to incoperand storing the sum back into incoperand.
NOTE: The value in m.inc_by is a number and can be used directly from the variable
If m.inc_per is logical False, the value of m.inc_by is added directly to incoperand and the sum is put back into incoperand.

14. We now do a limit check by comparing incoperand against the numeric value that was stored in the m.inc_until variable.
If incoperand exceeds m.inc_until, the current value of incoperand is changed to the value of m.inc_until.
If incoperand is less than m.inc_until, then no change.

15. We now check to see if a 2nd Action is to be performed. The program looks at the logical value stored in the m.inc_trig variable.
If logical false, the program continues at Step #20.
If true, the process continues 16. The program will extract the data stored in the Table A field named in the m.inc_2what variable and store the data it in a temporary variable incoperand2.

17. The logical value of the m.inc_2per variable determines if we increase by a percentage or discrete value.
If it is logical True, the program computes what m.inc_2by percent of incoperand2 is and then adds that result to incoperand2 storing the sum back into incoperand2.
NOTE: The value in m.inc_2by is a number and can be used directly from the variable
If m.inc_2per is logical False, the value of m.inc_2by is added directly to incoperand2 and the sum is put back into incoperand2.

18. We now do a limit check by comparing incoperand2 against the numeric value that was stored in the m.inc_2until variable.
If incoperand2 exceeds m.inc_2until, the current value of incoperand2 is changed to the value of m.inc_until2.
If incoperand2 is less than m.inc_2until, then no change
The new parameters have now been computed and they are copied back to the fields in the current record of the Table A.

19. The incoperand2 value is stored back to Table A's field named in the m.inc_2what variable 20. The incoperand value is stored back to Table A's field named in the m.inc_what variable
Now examine the Decrease Parameter philosophy as follows 21. The program then examines the m.dec_type variable and if=3, no action is performed and the program advances to Step #34. If other than 3, the processing continues 22. The next action is to examine the parameter name stored in the m.dec_when variable. The following table equates the numeric code in the m.dec_when variable with the field Table B field to examine or special action to perform:

| Numeric Code | Test Parameter | Table B field or Action |
| --- | --- | --- |
| 1 | Duration | duration |
| 2 | Distance | distance |
| 3 | Speed | speed |
| 4 | Intensity | intensity |
| 5 | Incline | incline |
| 6 | Calories | calories |
| 7 | Level | level |
| 8 | Elasped Days[1] | Compute Elasped Days |
| 9 | Completed[2] | Compute Completed |

[1]The Elasped Days test parameter is computed by looking at the ex_date field in the Table B record and subtracting from the current date.
[2]The Completed test parameter is computed by examining the completed field in the Table B's record. If the field contains a logical True, then the program will search backwards in the CWH (for a date before the current ex_date value in Table B) for a record matching the exercise and ex_set fields from Table A. The program will count how many consecutive record matches have a logical True in their completed filed. The counting stops as soon as a matching record has a logical False in the field. This number then represents the number of consecutively completed (without modification) prescribed exercises and becomes the completed count. If the current record completed field in Table B is logical false, the completed count is set to 0.

The data from the Table B field or Action is stored in the temporary variable, lookat 23. The program now examines the operator action stored in the m.dec_op variable. Using the decoded action:

| Symbol | Code # | Function |
| --- | --- | --- |
| > | 1 | Greater Than |
| < | 2 | Less Than |
| = | 3 | Equal To |
| >= | 4 | Greater or Equal To |
| <= | 5 | Less or Equal To |
| != | 6 | Not Equal |

The program evaluates the operand lookat and the test value in m.dec_wby.

24. If the evaluation is False (i.e. 100>120) The program aborts the current processing and continues at Step #34. If the evaluation is True (i.e. 120>100) the processing continues.

Now have established an active Decrease trigger condition

25. If the value of m.dec_type=2 then the ex_enable field of the Table A is set to logical false. The program jumps to Step #34.

If the value of m.dec_type=3 the program will extract the data stored in the CWR field named in by m.dec_what variable and store the data it in a temporary variable decoperand.

26. The logical value of the m.dec_per variable determines if we decrease by a percentage or discrete value.
    If it is logical True, the program computes what m.dec_by percent of decoperand is and then subtracts that result from decoperand storing the difference back into decoperand.
    NOTE: The value in m.dec_by is a number and can be used directly from the variable.
    If m.dec_per is logical False, the value of m.dec_by is subtracted directly from decoperand and the difference is put back into decoperand.

27. We now do a limit check by comparing decoperand against the numeric value that was stored in the m.dec_until variable.
    If decoperand is less than m.dec_until, the current value of decoperand is changed to the value of m.dec_until.
    If decoperand is more than m.dec_until, then no change.

28. We now check to see if a 2nd Action is to be performed. The program looks at the logical value stored in the m.dec_trig variable.
    If logical false, the program continues at Step #33
    If true, the process continues 29. The program will extract the data stored in the Table A field named in the m.dec_2what variable and store the data it in a temporary variable decoperand2.

30. The logical value of the m.dec_2per variable determines if we decrease by a percentage or discrete value.
    If it is logical True, the program computes what m.deinc_2by percent of decoperand2 is and then subtracts that result from decoperand2 storing the difference back into decoperand2.
    NOTE: The value in m.dec_2by is a number and can be used directly from the variable
    If m.dec_2per is logical False, the value of m.dec_2by is subtracted directly from decoperand2 and the difference is put back into decoperand2.

31. We now do a limit check by comparing decoperand2 against the numeric value that was stored in the m.dec_2until variable.
    If decoperand2 is less than m.dec_2until, the current value of decoperand2 is changed to the value of m.dec_until2. If decoperand2 is more than m.dec_2until, then no change.

The new parameters have now been computed and they are copied back to the fields in the current record of the Table A.

32 The decoperand2 value is stored back to Table A's field named in the m.dec_2what variable 33 The decoperand value is stored back to Table A's field named in the m.dec_what variable A single exercise record has been processed 34. The program then increments the record pointer for both Table A and Table B repeating the process from Step #7 until all records in Table A have been processed All records in Table A have been processed 35. All of the records from Table A are now copied back to their original positions in the CWR file. Table A is still intact and will be used in the following sections.

Exercise Description Block Compiling

The Table A created above contains descriptions of exercises to be performed in the order presented in the table. The DTA units require a specific format for a complete exercise description called an Exercise Block. There are six distinct exercise block formats. They are listed as follows:

1. Aerobic Exercise with Embedded Exercise Name
2. Aerobic Exercise with Lookup Table Code Exercise Name
3. Anaerobic Exercise with Embedded Exercise Name
4. Anaerobic Exercise with Lookup Table Code Exercise Name
5. Stretch Exercise with Embedded Exercise Name
6. Stretch Exercise with Lookup Table Code Exercise Name The Exercise Blocks are appended to the Header Block in the DTA Data Package Buffer. They follow one after the other until all the exercises have be reformatted and added to the DTA Data Package Buffer.

The ex_group field will indicate which type of exercise and the table_no field indicates if the Embedded Exercise Name is used or table lookup code number. Use the following table to determine which of the 6 exercise group classifications is represented by the Table A exercise record.

| ex_group | table_no | Exercise Group |
| --- | --- | --- |
| Aerobic | 0 | Aerobic Exercise with Embedded Exercise Name |
| Aerobic | Other than 0 | Aerobic Exercise with Lookup Table Code Exercise Name |
| Anaerobic | 0 | Anaerobic Exercise with Embedded Exercise Name |
| Anaerobic | Other than 0 | Anaerobic Exercise with Lookup Table Code Exercise Name |
| Stretch | 0 | Stretch Exercise with Embedded Exercise Name |
| Stretch | Other than 0 | Stretch Exercise with Lookup Table Code Exercise Name |

The following sections describe how each exercise record in Table A is re-formatted to the corresponding exercise block Aerobic Exercise w/Embedded Exercise Name NOTE: The following table lists the bytes in the formatted exercise block starting with the arbitrary number 1. The actual byte number in the DTA Data Package Buffer will depend upon its actual position amongst the other re-formatted exercise blocks.

NOTE: Those seatx fields that are blank (EMPTY) are set to Alpha with a numeric value of 0 (i.e. corresponding bit set in byte 2 and 0x0 in the setting byte)

Number of Settings Byte (Byte 3 Bits 7–5)

Bits 7–5 of Byte 3 represent the number of non-blank seatx fields in the Table A exercise's record. The program will trim the number to three bits and place them into the bit 7 to 5 position of Byte 3. Bit 7 being MSB.

Setting #1 Byte (Byte 3 Bits 4–0)

| BYTE 1 | Exercise Group | |
|---|---|---|
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7-5: | # OF SETTINGS (0–7) |
| | BITS 4-0: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Spare |
| BYTE 8 | BITS 7-0: | INTENSITY beats per minute (0–255) |
| BYTE 9 | BIT 7: | 1 = LEVEL IS ALPHA 0=LEVEL IS NUMERIC |
| | BITS 6-0: | LEVEL (0–127 or A–Z) |
| BYTE 10 | BITS 7-5: | RATE: 0=MPH 1=KPH 2=FPM 3=MPM 4=SPM |
| | BITS 4-0: | INCLINE (0–31°) |
| BYTE 11 | BIT 7 | SPEED Decimal Indicator 1 = decimal point 0 = no decimal |
| | BITS 6-0 | SPEED MSB |
| BYTE 12 | BITS 7-0 | SPEED LSB (0–32767) or (0.0 to 3276.7) |
| BYTE 13 | BITS 7-0: | CALORIES × 10 (0 TO 2550) |
| BYTE 14 | BIT 7-6: | Distance Type 0=Kilometers 1=Meters 2=Miles 3=feet |
| | BIT 5 | Distance Decimal Indicator 1 = decimal present |
| | BITS 4-0 | DISTANCE MSB |
| BYTE 15: | BITS 7-0: | DISTANCE LSB (0 to 8191 or 0.0 to 819.1) |
| BYTE 16 | BITS 7-0: | DURATION (0–255mins.) |
| BYTE 17: | BITS 7-4: | Duration type 0 = seconds 1=minutes 2=hours |
| | BITS 3-0 | #CHARACTERS IN EQUIPMENT NAME (1–6) + 1 |
| BYTE 18 | 222 11111 | |
| BYTE 19 | 4 33333 22 | |
| BYTE 20 | 5555 4444 | |
| BYTE 21 | 77 66666 5 | |
| BYTE 22 | 88888 777 | |
| BYTE 23 | AAA 99999 | |
| BYTE 24 | C BBBBB AA | |
| BYTE 25 | DDDD CCCC | |
| BYTE 26 | FF EEEEE D | |
| BYTE 27 | GGGGG FFF | |

Exercise Group Byte (Byte 1)

For an Aerobic Exercise with embedded exercise name, this command byte base is always 0x06. The exercise set taken from the ex_set field of Table A is trimmed to three bits and inserted in the upper nibble of the Exercise Group Byte bits 0–3.

For example: The exercise belongs to set 2: Exercise Group Byte=0x26

Mechanical Setting Format Byte (Byte 2)

The lower 6 bits in this byte indicate if the corresponding mechanical/ergonomic setting is an Alpha character (A–Z) or numeric character (0–32). The program examines the seat1 through seat7 fields of Table A and if it detects an Alpha character, the corresponding bit in Byte 2 is set. If the character string in the field represents a numeric value, the character string is converted into a number (stored back into its Table A field) and the corresponding bit in Byte 2 is cleared.

If the seat1 field is an Alpha character, the ASCII code is trimmed to the most significant 5-bits and stored in bits 4 to 0 of Byte 3. If the seat1 field was numeric, the converted value (ASCII numeric character to number) is also trimmed to 5-bits and stored in bits 4 to 0 of Byte 3. Bit 4 being MSB.

Remaining Settings Packed Bytes (Bytes 4–7)

NOTE: The seatx values are converted to the appropriate representation for Alpha or number and trimmed to 5 bits.

In a similar fashion as the client's Packed Last Name Bytes, the remaining mechanical/ergonomic setting values are packed into the next 4 bytes. In the following table, the number 2 represents the bits for the converted and trimmed seat2 field value, the number 3 for seat3, number 4 for seat4, etc. The last two bits in Byte 7 are unused and cleared. Any seatx field that was blank (EMPTY) has its bits all cleared (set to 0).

| | | |
|---|---|---|
| BYTE 4 | 333 22222 | complete #2, partial #3 |
| BYTE 5 | 5 44444 33 | remaining #3, complete #4, partial #5 |
| BYTE 6 | 6666 5555 | remaining #5, partial #6 |
| BYTE 7 | XX 77777 6 | remaining #6, complete #7 |
| | BIT 6: | Spare set to 0 |
| | BIT 7: | Spare set to 0 |

Intensity Setting Byte (Byte 8)

The intensity field value of Table A is trimmed to a single byte (valid range for field is 0–255) and stored in Byte 8

Level Setting Format Byte (Byte 9 Bit 7)

Bit 7 of Byte 9 indicates if the level field of Table A holds an Alpha character (A–Z) or a numeric character string (0–127). If the value is alpha, trim the ASCII character byte to 7 bits and set the Bit 7 of Byte 9. If the value is a numeric character string, convert the character string to an actual number, trim to 7 bits and clear Bit 7 or Byte 9.

Level Setting Byte (Byte 9 Bits 6–0)

The trimmed level value from above is stored in Bits 6–0 of Byte 9. Bit 6 being MSB.

Byte (Byte 10 Bits 7–5)

The spd_typ field from Table A contains a code number. Convert the code number as follows, trim to 3 bits and store in Bits 7 to 5 of Byte 10:

| spd_typ | Bits 7–5 | Units |
|---|---|---|
| 1 | 000 | mph |
| 2 | 001 | kph |
| 3 | 010 | fpm |
| 4 | 100 | mpm |
| 5 | 101 | spm |

Incline Setting Byte (Byte 10 Bits 4–0)
The incline field value from Table A is trimmed to 5 bits and stored to Bits 4 to 0 of Byte 10

Speed Decimal Indicator (Byte 11 Bit 7)

If the speed field from Table A is a value with a fraction (0.1 to 0.9), the program will set Bit 7 of Byte 11 and adjust the actual value as described in the following section.

Speed Setting Bytes (Byte 11 Bits 6–0 & Byte 12)

If the speed field from Table A has a fraction (0.1 to 0.9) the program must first multiply the value by 10 to get rid of the tenths value. If the speed field from Table A is an integer, no multiplication takes place. The product is then trimmed to the 15 bits with the most significant 7 bits stored in Bits 6 to 0 of Byte 11. Bit 6 being MSB. The remaining 8-bits are stored in Byte 12. Bit 7 being MSB.

Calories Setting Byte (Byte 13)

The calories field of Table A is divided by ten with the remainder discarded and the quotient trimmed to 8-bits. The resultant byte is stored to Byte 13. Bit 7 being MSB.

NOTE The calories field's VALID clause prevents a number not a multiple of ten from being entered.

Distance Unit Code Setting Byte (Byte 14 Bits 7–6)

The dis_typ field from Table A contains a code number. Convert the code number as follows, trim to 2 bits and store in Bits 7 to 6 of Byte 14:

| dis_typ | Bits 7–6 | Units |
|---|---|---|
| 1 | 00 | km. |
| 2 | 01 | m. |
| 3 | 10 | mi. |
| 4 | 11 | ft. |

Distance Decimal Indicator Byte (Byte 14 Bit 5)

If the distance field from Table A is a value with a fraction (0.1 to 0.9), the program will set Bit 5 of Byte 14 and adjust the actual value as described in the following section.

Distance Setting Bytes (Byte 14 Bits 4–0 & Byte 15)

If the distance from Table A has a fraction (0.1 to 0.9) the program must first multiply the value by 10 to get rid of the tenths value. If the distance field from Table A is an integer, no multiplacation takes place. The product is then trimmed to the 13 bits with the most significant 5 bits stored in Bits 4 to 0 of Byte 14. Bit 4 being MSB. The remaining 8-bits are stored in Byte 15. Bit 7 being MSB.

Duration Setting Byte (Byte 16)

The duration field of Table A is trimmed to 8-bits. The resultant byte is stored to Byte 16. Bit 7 being MSB.

Duration Unit Code Setting Byte (Byte 17 Bits 7–4)

The dur_typ field from Table A contains a code number. Convert the code number as follows, trim to 4 bits ant store in Bits 7 to 4 of Byte 17:

| dur_typ | Bits 7–4 | Units |
|---|---|---|
| 1 | 0000 | sec. |
| 2 | 0001 | min. |
| 3 | 0010 | hrs. | of Characters In Exercise Name Setting Byte (Byte 17 Bits 3–0)

The exercise field from Table A is trimmed of leading and training blanks, the number of character are counted and the value is trimmed to 4 bits. The value is then decremented such that 16 actual characters is represented by the number 15, 14 by 13, etc. The adjusted value stored to Bits 3 to 0 of Byte 17. Bit 3 being MSB Exercise Name Packed Bytes (Bytes 18–27)

In a similar fashion as the client's Packed Last Name Bytes, the embedded exercise name ASCII character values are packed into the next 10 bytes. All ASCII characters are trimmed to 5 bits. the upper 3 bits are added by the DTA software. In the following table, the number 1 represents the bits for the trimmed ASCII value of the exercise name's first character. The number 2 for the second character, A for 10th, etc. Unused or leftover bits are set to 0.

| | | |
|---|---|---|
| BYTE 18 | 222 11111 | 1st Character, partial 2nd |
| BYTE 19 | 4 33333 22 | remaining 2nd, complete 3rd & partial 4th |
| BYTE 20 | 5555 4444 | remaining 4th, partial 5th |
| BYTE 21 | 77 66666 5 | remaining 5th, complete 6th, partial 7th |
| BYTE 22 | 88888 777 | remaining 7th, complete 8th |
| BYTE 23 | AAA 99999 | complete 9th, partial 10th |
| BYTE 24 | C BBBBB AA | remaining 10th, complete 11th, partial 12th |
| BYTE 25 | DDDD CCCC | remaining 12th, partial 13th |
| BYTE 26 | FF EEEEE D | remaining 13th, complete 14th, partial 15th |
| BYTE 27 | GGGGG FFF | remaining 15th, complete 16th |

Aerobic Exercise with okup Table Code Exercise Name
NOTE: The following table lists the bytes in the formatted exercise block starting with the arbitrary number 1. The actual byte number in the DTA Data Package Buffer will depend upon its actual position amongst the other re-formatted exercise blocks.

| | | |
|---|---|---|
| BYTE 1 | Exercise Group | |
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7–5: | # OF SETTINGS (0–7) |
| | BITS 4–0: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Spare |
| BYTE 8 | BITS 7–0: | INTENSITY beats per minute (0–255) |
| BYTE 9 | BIT 7: | 1 = LEVEL IS ALPHA 0=LEVEL IS NUMERIC |
| | BITS 6–0: | LEVEL (0–127 or A–Z) |
| BYTE 10 | BITS 7–5: | RATE: 0=MPH 1=KPH 2=FPM 3=MPM 4=SPM |
| | BITS 4–0: | INCLINE (0–31°) |
| BYTE 11 | BIT 7 | SPEED Decimal Indicator 1 = decimal point 0 = no decimal |
| | BITS 6–0 | SPEED MSB |
| BYTE 12 | BITS 7–0 | SPEED LSB (0–32767) or (0.0 to 3276.7) |
| BYTE 13 | BITS 7–0: | CALORIES x 10 (0 TO 2550) |
| BYTE 14 | BIT 7–6: | Distance Type 0=Kilometers 1=Meters 2=Miles 3=feet |
| | BIT 5 | Distance Decimal Indicator 1 = decimal present |
| | BITS 4–0 | DISTANCE MSB |
| BYTE 15: | BITS 7–0: | DISTANCE LSB (0 to 8191 or 0.0 to 819.1) |
| BYTE 16 | BITS 7–0: | DURATION (0–255 mins.) |
| BYTE 17: | BITS 7–4: | Duration type 0 = seconds 1=minutes 2=hours |
| | BITS 3–0 | Set to 0 |
| BYTE 18: | Lookup Table # LSB | |
| BYTE 19: | Lookup Table # MSB | |

Exercise Group Byte (Byte 1)

For an Aerobic Exercise with Lookup Table Code, this command byte base is always 0x07. The exercise set taken from the ex_set field of Table A is trimmed to three bits and inserted in the upper nibble of the Exercise Group Byte bits 0–3.

For example: The exercise belongs to set 3: Exercise Group Byte=0x37

Mechanical Setting Format Byte (Byte 2)

The lower 6 bits in this byte indicate if the corresponding mechanical/ergonomic setting is an Alpha character (A–Z) or numeric character (0–32). The program examines the seat1 through seat7 fields of Table A and if it detects an Alpha character, the corresponding bit in Byte 2 is set. If the character string in the field represents a numeric value, the character string is converted into a number (stored back into its Table A field) and the corresponding bit in Byte 2 is cleared.

NOTE: Those seatx fields that are blank (EMPTY) are set to Alpha with a numeric value of 0 (i.e. corresponding bit set in byte 2 and 0x0 in the setting byte)

Number of Settings Byte (Byte 3 Bits 7–5)

Bits 7–5 of Byte 3 represent the number of non-blank seatx fields in the Table A exercise's record. The program will trim the number to three bits and place them into the bit 7 to 5 position of Byte 3. Bit 7 being MSB.

Setting #1 Byte (Byte 3 Bits 4–0)

If the seat1 field is an Alpha character, the ASCII code is trimmed to the most significant 5-bits and stored in bits 4 to 0 of Byte 3. If the seat1 field was numeric, the converted value (ASCII numeric character to number) is also trimmed to 5-bits and stored in bits 4 to 0 of Byte 3. Bit 4 being MSB.

Remaining Settings Packed Bytes (Bytes 4–7)

NOTE: The seatx values are converted to the appropriate representation for Alpha or number and trimmed to 5 bits.

In a similar fashion as the client's Packed Last Name Bytes, the remaining mechanical/ergonomic setting values are packed into the next 4 bytes. In the following table, the number 2 represents the bits for the converted and trimmed seat2 field value, the number 3 for seat3, number 4 for seat4, etc. The last two bits in Byte 7 are unused and cleared. Any seatx field that was blank (EMPTY) has its bits all cleared (set to 0).

| | | |
|---|---|---|
| BYTE 4 | 333 22222 | complete #2, partial #3 |
| BYTE 5 | 5 44444 33 | remaining #3, complete #4, partial #5 |
| BYTE 6 | 6666 5555 | remaining #5, partial #6 |
| BYTE 7 | XX 77777 6 | remaining #6, complete #7 |
| | BIT 6: | Spare set to 0 |
| | BIT 7: | Spare set to 0 |

Intensity Setting Byte (Bytes 8)

The intensity field value of Table A is trimmed to a single byte (valid range for field is 0–255) and stored in Byte 8

Level Setting Format Byte (Byte 9 Bit 7)

Bit 7 of Byte 9 indicates if the level field of Table A holds an Alpha character (A–Z) or a numeric character string (0–127). If the value is alpha, trim the ASCII character byte to 7 bits and set the Bit 7 of Byte 9. If the value is numeric character string, convert the character string to an actual number, trim to 7 bits and clear Bit 7 or Byte 9.

Level Setting Byte (Byte 9 Bits 6–0)

The trimmed level value from above is stored in Bits 6–0 of Byte 9. Bit 6 being MSB.

Byte (Byte 10 Bits 7–5)

The spd_typ field from Table A contains a code number. Convert the code number as follows, trim to 3 bits and store in Bits 7 to 5 of Byte 10:

| spd_typ | Bits 7–5 | Units |
|---|---|---|
| 1 | 000 | mph |
| 2 | 001 | kph |
| 3 | 010 | fpm |
| 4 | 100 | mpm |
| 5 | 101 | spm |

Incline Setting Bytes )Byte 10 Bits 4–0)

The incline field value from Table A is trimmed to 5 bits and stored to Bits 4 to 0 of Byte 10

Speed Decimal Indicator Byte (Byte 11 Bit 7)

If the speed field from Table A is a value with a fraction (0.1 to 0.9), the program will set Bit 7 of Byte 11 and adjust the actual value as described in the following section.

Speed Setting Bytes (Bytes 11 Bits 6–0 & Byte 12)

If the speed field from Table A has a fraction (0.1 to 0.9) the program must first multiply the value by 10 to get rid of the tenths value. If the speed field from Table A is an integer, no multiplication takes place. The product is then trimmed to the 15 bits with the most significant 7 bits stored in Bits 6 to 0 of Byte 11. Bit 6 being MSB. The remaining 8-bits are stored in Byte 12. Bit 7 being MSB.

Calories Setting Byte (Byte 13)

The calories field of Table A is divided by ten with the remainder discarded and the quotient trimmed to 8-bits. The resultant byte is stored to Byte 13. Bit 7 being MSB.

NOTE The calorie field's VALID clause prevents a number not a multiple of ten from being entered.

Distance Unit Code Setting Byte (Byte 14 Bits 7–6)

The dis_typ field from Table A contains a code number. Convert the code number as follows, trim to 2 bits and store in Bits 7 to 6 of Byte 14:

| dis_typ | Bits 7–6 | Units |
|---|---|---|
| 1 | 00 | km. |
| 2 | 01 | m. |
| 3 | 10 | mi. |
| 4 | 11 | ft. |

Distance Decimal Indicator Byte (Byte 14 Bit 5)

If the distance field from Table A is a value with a fraction (0.1 to 0.9), the program will set bit 5 of Byte 14 and adjust the actual value as described in the following section.

Distance Setting Bytes (Byte 14 Bits 4–0 & Byte 15)

If the distance field from Table A has a fraction (0.1 to 0.9) the program must first multiply the value by 10 to get rid of the tenths value. If the distance field from Table A is an integer, no multiplication takes place. The product is then trimmed to the 13 bits with the most significant 5 bits stored in Bits 4 to 0 of Byte 14. Bit 4 being MSB. The remaining 8-bits are stored in Byte 15. Bit 7 MSB.

Duration Setting Byte (Byte 16)

The duration field of Table A is trimmed to 8-bits. The resultant byte is stored to Byte 16. Bit 7 being MSB.

Duration Unit Code Setting Byte (Byte 17 Bits 7–4)

The dur_typ field from Table A contains a code number. Convert the code number as follows, trim to 4 bits and store in Bits 7 to 4 of Byte 17:

| dur_typ | Bits 7–4 | Units |
|---|---|---|
| 1 | 0000 | sec. |
| 2 | 0001 | min. |
| 3 | 0010 | hrs. |

Lookup Table # Bytes (Bytes 18–19)

The table_no field from Table A contains a lookup table code number. Trim to number to two bytes and store the LSB in Byte 18 and the MSB in Byte 19.

Anaerobic Exercise W/embedded Exercise Name

NOTE: The following table lists the bytes in the formatted exercise block starting with the arbitrary number 1. The actual byte number in the DTA Data Package Buffer will depend upon its actual position amongst the other re-formatted exercise blocks.

| BYTE 1 | Exercise Group | |
|---|---|---|
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7–5: | # OF SETTINGS (0–7) |
| | BITS 4–0: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Spare |
| BYTE 8 | BIT 7: | 0 = POUNDS 1 = PLATES |
| | BIT 6: | 1 = Decimal in pounds/Plate 0 = No decimal |
| | BITS 5–0: | POUNDS/PLATES MSB |
| BYTE 9 | BITS 7–0 | POUNDS/PLATES (0–16383 (1638.3)) LSB |
| BYTE 10 | BITS 7–4 | Duration type 0 = seconds 1 = minutes 2 = hours |
| | BITS 3–0 | Spare |
| BYTE 11 | BITS 7–0 | DURATION (0–255) |
| BYTE 12 | BITS 7–0 | REPS (0–255) |
| BYTE 13 | BITS 7–4: | SETS (0–15) |
| | BITS 3–0 | # CHARACTERS IN EQUIPMENT NAME (1–16) +1 |
| BYTE 14 | 222 11111 | |
| BYTE 15 | 4 33333 22 | |
| BYTE 16 | 5555 4444 | |
| BYTE 17 | 77 66666 5 | |
| BYTE 18 | 88888 777 | |
| BYTE 19 | AAA 99999 | |
| BYTE 20 | C BBBBB AA | |
| BYTE 21 | DDDD CCCC | |
| BYTE 22 | FF EEEEE D | |
| BYTE 23 | GGGGG FFF | |

Exercise Group Byte (Byte 1)

For an Anaerobic Exercise with embedded exercise name, this command byte base is always 0x08. The exercise set taken from the ex_set field of Table A is trimmed to three bits and inserted in the upper nibble of the Exercise Group Byte bits 0–3.

For example: The exercise belongs to set 5: Exercise Group Byte=0x58

Mechanical Setting Format Byte (Byte 2)

The lower 6 bits in this byte indicate if the corresponding mechanical/ergonomic setting is an Alpha character (A–Z) or numeric character (0–32). The program examines the seat1 through seat7 fields of Table A and if it detects an Alpha character, the corresponding bit in Byte 2 is set. If the character string in the field represents a numeric value, the character string is converted into a number (stored back into its Table A field) and the corresponding bit in Byte 2 is cleared.

NOTE: Those seatx fields that are blank (EMPTY) are set to Alpha with a numeric value of 0 (i.e. corresponding bit set in byte 2 and 0x0 in the setting byte)

Number of Settings Byte (Byte 3 Bits 7–5)

Bits 7–5 of Byte 3 represent the number of non-blank seatx fields in the Table A exercise's record. The program will trim the number to three bits and place them into the bit 7 to 5 position of Byte 3. Bit 7 being MSB.

Setting #1 Byte (Byte 3 Bits 4–0)

If the seat1 field is an Alpha character, the ASCII code is trimmed to the most significant 5-bits and stored in bits 4 to 0 of Byte 3. If the seat1 field was numeric, the converted value (ASCII numeric character to number) is also trimmed to 5-bits and stored in bits 4 to 0 of Byte 3. Bit 4 being MSB.

Remaining Settings Packed Bytes (Bytes 4–7)

NOTE: The seatx values are converted to the appropriate representation for Alpha or number and trimmed to 5 bits.

In a similar fashion as the client's Packed Last Name Bytes, the remaining mechanical/ergonomic setting values are packed into the next 4 bytes. In the following table, the number 2 represents the bits for the converted and trimmed seat2 field value, the number 3 for seat3, number 4 for seat4, etc. The last two bits in Byte 7 are unused and cleared. Any seatx field that was blank (EMPTY) has its bits all cleared (set to 0).

| BYTE 4 | 333 22222 | complete #2, partial #3 |
|---|---|---|
| BYTE 5 | 5 44444 33 | remaining #3, complete #4, partial #5 |

-continued

| BYTE 6 | 6666 5555 | remaining #5, partial #6 |
| BYTE 7 | XX 77777 6 | remaining #6, complete #7 |
| | BIT 6: | Spare set to 0 |
| | BIT 7: | Spare set to 0 |

Pounds or Plates Type Setting Byte (Byte 8 Bit 7)

The lbs_plt field value of Table A contains a numeric value. If=1 then pounds are selected and Bit 7 of Byte 8 is cleared (0). If the value of lbs_plt is 0, set Bit 7 of Byte 8 to 1

Pounds/Plates Decimal Indicator Byte (Byte 8 Bit 6)

If the pounds field from Table A is a value with a fraction (0.1 to 0.9), the program will set Bit 6 of Byte 8 and adjust the actual value as described in the following section.

Pounds/Plates Setting Bytes (Byte 8 Bits 5–0 & Byte 9)

If the pounds field from Table A has a fraction (0.1 to 0.9) the program must first multiply the value by 10 to get rid of the tenths value. If the pounds field from Table A is an integer, no multiplication takes places The product is then trimmed to the 14 bits with the most significant 6 bits stored in Bits 5 to 0 of Byte 8. Bit 5 being MSB. The remaining 8-bits are stored in Byte 9. Bit 7 being MSB.

Duration Unit Code Setting Byte (Byte 10 Bits 7–4)

The dur_typ field from Table A contains a code number. Convert the code number as follows, trim to 4 bits and store in Bits 7 to 4 of Byte 10:

| dur_typ | Bits 7–4 | Units |
| --- | --- | --- |
| 1 | 0000 | sec. |
| 2 | 0001 | min. |
| 3 | 0010 | hrs. |

NOTE: Bits 3–0 of Byte 10 are set to 0

Duration Setting Byte (Byte 11)

The duration field of Table A is trimmed to 8-bits. The resultant byte is stored to Byte 11. Bit 7 being MSB.

Repetitions Setting Byte 12)

The reps field of Table A is trimmed to 8-bits. The resultant byte is stored to Byte 12. Bit 7 being MSB.

Sets Setting Byte (Byte 13 Bits 7–4)

The sets field of Table A is trimmed to 4-bits. The resultant value is stored to Bits 7 to 4 of Byte 13. Bit 7 being MSB.

# of characters in Exercise Name Setting Byte (Byte 13 Bits 3–0)

The exercise field from Table A is trimmed of leading and training blanks, the number of character are counted and the value is trimmed to 4 bits. The value is then decremented such that 16 actual characters is represented by the number 15, 14 by 13, etc. The adjusted value stored to Bits 3 to 0 of Byte 13. Bit 3 being MSB Exercise Name Packed Bytes (Bytes 14–23)

In a similar fashion as the client's Packed Last Name Bytes, the embedded exercise name ASCII character values are packed into the next 10 bytes. All ASCII characters are trimmed to 5 bits. the upper 3 bits are added by the DTA software. In the following table, the number 1 represents the bits for the trimmed ASCII value of the exercise name's first character. The number 2 for the second character, A for 10th, etc. Unused or leftover bits are set to 0.

| BYTE 14 | 222 11111 | 1st Character, partial 2nd |
| BYTE 15 | 4 33333 22 | remaining 2nd, complete 3rd & partial 4th |
| BYTE 16 | 5555 4444 | remaining 4th, partial 5th |
| BYTE 17 | 77 66666 5 | remaining 5th, complete 6th, partial 7th |
| BYTE 18 | 88888 777 | remaining 7th, complete 8th |
| BYTE 19 | AAA 99999 | complete 9th, partial 10th |
| BYTE 20 | C BBBBB AA | remaining 10th, complete 11th, partial 12th |
| BYTE 21 | DDDD CCCC | remaining 12th, partial 13th |
| BYTE 22 | FF EEEEE D | remaining 13th, complete 14th, partial 15th |
| BYTE 23 | GGGGG FFF | remaining 15th, complete 16th |

Anaerobic Exercise with Lookup Table Code Exercise Name

NOTE: The following table slits the bytes in the formatted exercise block starting with the arbitrary number 1. The actual byte number in the DTA Data Package Buffer will depend upon its actual position amongst the other re-formatted exercise blocks.

| BYTE 1 | Exercise Group | |
| --- | --- | --- |
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7–5: | # OF SETTINGS (0–7) |
| | BITS 4–0: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Spare |
| BYTE 8 | BIT 7: | 0 = POUNDS 1 = PLATES |
| | BIT 6: | 1 = Decimal in pounds/Plate |
| | | 0 = No decimal |
| | BITS 5–0: | POUNDS/PLATES MSB |
| BYTE 9 | BITS 7–0 | POUNDS/PLATES (0–16383 (1638.3)) LSB |
| BYTE 10 | BITS 7–0 | REPS (0–255) |
| BYTE 11 | BITS 7–4: | SETS (0–15) |
| | BITS 3–0 | Duration type 0 = seconds 1 = minutes 2 = hours |
| BYTE 12 | BITS 7–0 | DURATION (0–255) |
| BYTE 13 | LOOKUP TABLE # LSB | |
| BYTE 14 | LOOKUP TABLE # MSB | |

Exercise Group Byte (Byte 1)

For an Anaerobic Exercise with Lookup Table Code, this command byte base is always 0x09. The exercise set taken from the ex_set field of Table A is trimmed to three bits and inserted in the upper nibble of the Exercise Group Byte bits 0–3.

For example: The exercise belongs to set 3: Exercise Group Byte=0x39

Mechanical Setting Format Byte (Byte 2)

The lower 6 bits in this byte indicate if the corresponding mechanical/ergonomic setting is an Alpha character (A–Z) or numeric character (0–32). The program examines the seat1 through seat7 fields of Table A and if it detects an Alpha character, the corresponding bit in Byte 2 is set. If the character string in the field represents a numeric value, the character string is converted into a number (stored back into its Table A field) and the corresponding bit in Byte 2 is cleared.

NOTE: Those seatx fields that are blank (EMPTY) are set to Alpha with a numeric value of 0 (i.e. corresponding bit set in byte 2 and 0x0 in the setting byte)

Number of Settings Byte (Byte 3 Bits 7–5)

Bits 7–5 of Byte 3 represent the number of non-blank seatx fields in the Table A exercise's record. The program will trim the number to three bits and place them into the bit 7 to 5 position of Byte 3. Bit 7 being MSB.
Setting #1 Byte (Byte 3 Bits 4–0)
If the seat1 field is an Alpha character, the ASCII code is trimmed to the most significant 5-bits and stored in bits 4 to 0 of Byte 3. If the seat1 field was numeric, the converted value (ASCII numeric character to number) is also trimmed to 5-bits and stored in bits 4 to 0 of Byte 3. Bit 4 being MSB.
Remaining Settings Packed Bytes (Bytes 4–7)
NOTE: The seatx values are converted to the appropriate representation for Alpha or number and trimmed to 5 bits.

In a similar fashion as the client's Packed Last Name Bytes, the remaining mechanical/ergonomic setting values are packed into the next 4 bytes. In the following table, the number 2 represents the bits for the converted and trimmed seat2 field value, the number 3 for seat3, number 4 for seat4, etc. The last two bits in Byte 7 are unused and cleared. Any seatx field that was blank (EMPTY) has its bits all cleared (set to 0).

| | | |
|---|---|---|
| BYTE 4 | 333 22222 | complete #2, partial #3 |
| BYTE 5 | 5 44444 33 | remaining #3, complete #4, partial #5 |
| BYTE 6 | 6666 5555 | remaining #5, partial #6 |
| BYTE 7 | XX 77777 6 | remaining #6, complete #7 |
| | BIT 6: | Spare set to 0 |
| | BIT 7: | Spare set to 0 |

Pounds or Plates Type Setting Byte (Byte 8 Bit 7)
The lbs_plt field value of Table A contains a numeric value. If=1 then pounds are selected and Bit 7 of Byte 8 is cleared (0). If the value of lbs_plt is 0, set Bit 7 of Byte 8 to 1
Pounds/Plates Decimal Indicator Byte (Byte 8 Bit 6)
If the pounds field from Table A is a value with a fraction (0.1 to 0.9), the program will set Bit 6 of Byte 8 and adjust the actual value as described in the following section.
Pounds/Plates Setting Bytes (Byte 8 Bits 5–0 & Byte 9)
If the pounds field from Table A has a fraction (0.1 to 0.9) the program must first multiply the value by 10 to get rid of the tenths value. If the pounds field from Table A is an integer, no multiplication takes places The product is then trimmed to the 14 bits with the most significant 6 bits stored in Bits 5 to 0 of Byte 8. Bit 5 being MSB. The remaining 8-bits are stored in Byte 9. Bit 7 being MSB.
Repetitions Setting Byte (Byte 10)
The reps field of Table A is trimmed to 8-bits. The resultant byte is stored to Byte 10. Bit 7 being MSB.
Sets setting Byte (Byte 11 Bits 7–4)
The sets field of Table A is trimmed to 4-bits. The resultant value is stored to Bits 7 to 4 of Byte 11. Bit 7 being MSB.
Duration Unit Code Setting Byte (Byte 11 Bits 3–0)
The dur_typ field from Table A contains a code number. Convert the code number as follows, trim to 4 bits and store in Bits 3 to 0 of Byte 11:

| dur_typ | Bits 3–0 | Units |
|---|---|---|
| 1 | 0000 | sec. |
| 2 | 0001 | min. |
| 3 | 0010 | hrs. |

Duration Setting Byte (Byte 12)
The duration field of Table A is trimmed to 8-bits. The resultant byte is stored to Byte 12. Bit 7 being MSB.
Lookup Table # Bytes (Bytes 13–14)
The table_no field from Table A contains a lookup table code number. Trim to number to two bytes and store the LSB in Byte 13 and the MSB in Byte 14.

Stretch Exercise w/Embedded Exercise Name
NOTE: The following table slits the bytes in the formatted exercise block starting with the arbitrary number 1. The actual byte number in the DTA Data Package Buffer will depend upon its actual position amongst the other re-formatted exercise blocks.

| | | |
|---|---|---|
| BYTE 1 | Exercise Group | |
| BYTE 2 | BITS 7–0: | DURATION (0–255) |
| BYTE 3 | BITS 7–4: | Duration type 0 = seconds 1=minutes 2=hours |
| | BITS 3–0: | Spare |
| BYTE 4 | BIT 7–0: | REPS (0–255) |
| BYTE 5 | BITS 7–4: | SETS (0–15) |
| | BITS 3–0 | # CHARACTERS IN EQUIPMENT NAME (1–16) +1 |
| BYTE 6 | 222 11111 | |
| BYTE 7 | 4 33333 22 | |
| BYTE 8 | 5555 4444 | |
| BYTE 9 | 77 66666 5 | |
| BYTE 10 | 88888 777 | |
| BYTE 11 | AAA 99999 | |
| BYTE 12 | C BBBBB AA | |
| BYTE 13 | DDDD CCCC | |
| BYTE 14 | FF EEEEE D | |
| BYTE 15 | GGGGG FFF | |

Exercise Group Byte (Byte 1)
For an Stretch Exercise with embedded exercise name, this command byte base is always 0x0A. The exercise set taken from the ex_set field of Table A is trimmed to three bits and inserted in the upper nibble of the Exercise Group Byte bits 0–3.
For example: The exercise belongs to set 3: Exercise Group Byte=0x3A
Duration Setting Byte (Byte 2)
The duration field of Table A is trimmed to 8-bits. The resultant byte is stored to Byte 2. Bit 7 being MSB.
Duration Unit Code Setting Byte (Byte 3 Bits 7–4)
The dur_typ field from Table A contains a code number. Convert the code number as follows, trim to 4 bits and store in Bits 7 to 4 of Byte 3:

| dur_typ | Bits 7–4 | Units |
|---|---|---|
| 1 | 0000 | sec. |
| 2 | 0001 | min. |
| 3 | 0010 | hrs. |

NOTE: Bits 3–0 of Byte 10 are set to 0
Repetitions Setting Byte (Byte 4)
The reps field of Table A is trimmed to 8-bits. The resultant byte is stored to Byte 4. Bit 7 being MSB.
Sets setting Byte (Byte 5 Bits 7–4)
The sets field of Table A is trimmed to 4-bits. The resultant value is stored to Bits 7 to 4 of Byte 5. Bit 7 being MSB.
of Characters In Exercise Name Setting Byte (Byte 5 Bits 3–0)
The exercise field from Table A is trimmed of leading and training blanks, the number of character are counted and the value is trimmed to 4 bits. The value is then decremented such that 16 actual characters is represented by the number 15, 14 by 13, etc. The adjusted value stored to Bits 3 to 0 of Byte 5. Bit 3 being MSB
Exercise Name Packed Bytes (Bytes 6–15)
In a similar fashion as the client's Packed Last Name Bytes, the embedded exercise name ASCII character values are packed into the next 10 bytes. All ASCII characters are trimmed to 5 bits. the upper 3 bits are added by the DTA software. In the following table, the number 1 represents the bits for the trimmed ASCII value of the exercise name's first character. The number 2 for the second character, A for 10th, etc. Unused or leftover bits are set to 0.

| BYTE 6 | 222 11111 | 1st Character, partial 2nd |
|---|---|---|
| BYTE 7 | 4 33333 22 | remaining 2nd, complete 3rd & partial 4th |
| BYTE 8 | 5555 4444 | remaining 4th, partial 5th |
| BYTE 9 | 77 66666 5 | remaining 5th, complete 6th, partial 7th |
| BYTE 10 | 88888 777 | remaining 7th, complete 8th |
| BYTE 11 | AAA 99999 | complete 9th, partial 10th |
| BYTE 12 | C BBBBB AA | remaining 10th, complete 11th, partial 12th |
| BYTE 13 | DDDD CCCC | remaining 12th, partial 13th |
| BYTE 14 | FF EEEEE D | remaining 13th, complete 14th, partial 15th |
| BYTE 15 | GGGGG FFF | remaining 15th, complete 16th |

Stretch Exercise with Lookup Table Code Exercise Name
NOTE: The following table slits the bytes in the formatted exercise block starting with the arbitrary number 1. The actual byte number in the DTA Data Package Buffer will depend upon its actual position amongst the other re-formatted exercise blocks.

| BYTE 1 | Exercise Group |
|---|---|
| BYTE 2 | BITS 7–0: DURATION (0–255) |
| BYTE 3 | BITS 7–4: Duration type 0 = seconds 1=minutes 2=hours |
| | BITS 3–0: Spare |
| BYTE 4 | BIT 7–O: REPS (0–255) |
| BYTE 5 | BITS 7–4: SETS (0–15) |
| | BITS 3–0 spare |
| BYTE 6 | Lookup Table # LSB |
| BYTE 7 | Lookup Table # MSB |

Exercise Group Byte (Byte 1)

For an Stretch Exercise with Lookup Table Code, this command byte base is always 0x0B. The exercise set taken from the ex_set field of Table A is trimmed to three bits and inserted int the upper nibble of the Exercise Group Byte bits 0–3.

For example: The exercise belongs to set 7: Exercise Group Byte=0x7B

Duration Setting Byte (Byte 2)

The duration field of Table A is trimmed to 8-bits. The resultant byte is stored to Byte 2. Bit 7 being MSB. Duration Unit Code Setting Byte (Byte (Byte 3 Bits 7–4)

The dur_typ field from Table A contains a code number. Convert the code number as follows, trim to 4 bits and store in Bits 7 to 4 of Byte 3:

| dur_typ | Bits 7–4 | Units |
|---|---|---|
| 1 | 0000 | sec. |
| 2 | 0001 | min. |
| 3 | 0010 | hrs. |

NOTE: Bits 3–0 of Byte 10 are set to 0
Repetitions Setting Byte (Byte 4)

The reps field of Table A is trimmed to 8-bits. The resultant byte is stored to Byte 4. Bit 7 being MSB.
Sets Setting Byte (Byte 5 Bits 7–4)

The sets field of Table A is trimmed to 4-bits. The resultant value is stored to Bits 7 to 4 of Byte 5. Bit 7 being MSB.
NOTE: Bits 3–0 of Byte are set to 0
Lookup Table # Bytes (Bytes 6–7)

The table_no field from Table A contains a lookup table code number. Trim to number to two bytes and store the LSB in Byte 6 and the MSB in Byte 7.
Footer Byte After all the exercise records in Table A have been compiled into exercise blocks and added to the DTA Data Package Buffer, the Footer Byte is appended to tell the DTA that there are no more exercises to process.

Footer Byte=0x04

Checksum

Following the addition of the Footer Byte, the program will count the number of bytes starting with the Header Block's Header Command and including the Footer Byte. IF THE NUMBER OF BYTES IS GREATER THAN 960 then display the bytes.scx alert screen:

Pressing the OK button returns the user back to the screen from which the Program DTA procedure was called from.

The user must then edit the workout routine either reducing the number of exercises or replacing some of the user defined exercise names with table lookup exercises to reduce the size of exercise blocks.

Assuming the byte count was not excessive, the program starts with Header Block's Header Command performs a Modulo-256 checksum up to and including the Footer Byte. The resultant byte (all carries out of the byte are ignored) is appended to the end of the DTA Data Package Buffer (after the footer byte). The Package is now ready to be transmitted to the DTA unit.

Transmitting the Package

By operational definition, a DTA unit has been previously loaded into its Programming Stand and is initialized awaiting a data transmission. The DTA displays:

"READY TO PROGRAM"

The Program DTA Procedure will then transmit the DTA Data Package Buffer, starting with the Header Block's Header Command byte and ending with the checksum byte through the computer's COM1 port at 9600 BAUD with 8 data bits, 1 start bit, 1 stop bit and no parity.

Upon completion of the transmission, the program will sound the computer's bell and display the following:

DTA PROGRAMMED

The Program DTA Procedure then exits back to the screen from which it was called.

NOTE: Any transmission difficulties are handled either by Windows or if at the DTA end, the DTA's communication software. In either case the user should be offered the option or retrying or aborting.

Receive From DTA Subfunction

The only way to activate the Receive From DTA Subfunction is using the DTA→Receive DTA menu option from the Workout Builder Screen or the Download DTA push button from the Automatic Mode screen.

The basic procedure is a reversal of the Transmit to DTA Subfunction. The data package received from the DTA is in the exact format as the package transmitted to it. The only difference being some changes in the embedded parameter values and some of the command header bytes change to reflect the completion status of the exercise DTA Download Command By operational definition, a DTA unit has been returned to the Programming Stand and has been placed in a state such that transmission of its data is possible. The Receive From DTA Subfunction must first transmit the download command to the DTA. This is a single byte as follows:

DTA Download Request=0x03

Immediately following this transmission, the computer must be readied to receive 961 bytes from the DTA into a buffer where the Program DTA Procedure code can have access to it.

Checksum Test

The Receive From DTA Subfunction will first checksum the received data package, starting at the beginning of the buffer until the Footer Byte is detected. The checksum is compared against the checksum embedded as the byte after the Footer in the received data package. Following successful checksumming the buffer is parsed and the data elements extracted and stored in the appropriate client's CWH table.

In order for the checksumming code to detect the Footer byte, it must count bytes and look for the Footer byte code 0x04 in an expected byte position in the received DTA data buffer. A counting algorithm is used to determine what byte number in the buffer the Footer resides in. Once known a checksum can be performed up to and including the Footer byte.

The counting algorithm executes as follows:

1. Start with a byte count=19
2. Skip the first 19 Header Block Bytes
3. Mask off the upper nibble of the next byte. If it then=0x6 look at the 16th byte after this one then:

--- if the lower 4 bits of the byte = 0x0 then add 19 to current byte count
if the lower 4 bits of the byte = 0x1 then add 20 to current byte count
if the lower 4 bits of the byte = 0x2 then add 20 to current byte count
if the lower 4 bits of the byte = 0x3 then add 21 to current byte count
if the lower 4 bits of the byte = 0x4 then add 22 to current byte count
if the lower 4 bits of the byte = 0x5 then add 22 to current byte count
if the lower 4 bits of the byte = 0x6 then add 23 to current byte count
if the lower 4 bits of the byte = 0x7 then add 23 to current byte count
if the lower 4 bits of the byte = 0x8 then add 24 to current byte count
if the lower 4 bits of the byte = 0x9 then add 25 to current byte count
if the lower 4 bits of the byte = 0xA then add 25 to current byte count
if the lower 4 bits of the byte = 0xB then add 26 to current byte count
if the lower 4 bits of the byte = 0xC then add 27 to current byte count
if the lower 4 bits of the byte = 0xD then add 27 to current byte count
if the lower 4 bits of the byte = 0xE then add 28 to current byte count
if the lower 4 bits of the byte = 0xF then add 28 to current byte count
OR
Mask off the upper nibble of the next byte. If it = 0x8 look at the 12th byte after this one then:
if the lower 4 bits of the byte = 0x0 then add 15 to current byte count
if the lower 4 bits of the byte = 0x1 then add 16 to current byte count
if the lower 4 bits of the byte = 0x2 then add 16 to current byte count
if the lower 4 bits of the byte = 0x3 then add 17 to current byte count
if the lower 4 bits of the byte = 0x4 then add 18 to current byte count
if the lower 4 bits of the byte = 0x5 then add 18 to current byte count
if the lower 4 bits of the byte = 0x6 then add 19 to current byte count
if the lower 4 bits of the byte = 0x7 then add 19 to current byte count
if the lower 4 bits of the byte = 0x8 then add 20 to current byte count
if the lower 4 bits of the byte = 0x9 then add 21 to current byte count
if the lower 4 bits of the byte = 0xA then add 21 to current byte count
if the lower 4 bits of the byte = 0xB then add 22 to current byte count
if the lower 4 bits of the byte = 0xC then add 23 to current byte count
if the lower 4 bits of the byte = 0xD then add 23 to current byte count
if the lower 4 bits of the byte = 0xE then add 24 to current byte count
if the lower 4 bits of the byte = 0xF then add 24 to current byte count
OR
Mask off the upper nibble of the next byte. If it = 0xA look at the 4th byte
after this one then:
if the lower 4 bits of the byte = 0x0 then add 7 to current byte count
if the lower 4 bits of the byte = 0x1 then add 8 to current byte count
if the lower 4 bits of the byte = 0x2 then add 8 to current byte count
if the lower 4 bits of the byte = 0x3 then add 9 to current byte count
if the lower 4 bits of the byte = 0x4 then add 10 to current byte count
if the lower 4 bits of the byte = 0x5 then add 10 to current byte count
if the lower 4 bits of the byte = 0x6 then add 11 to current byte count
if the lower 4 bits of the byte = 0x7 then add 11 to current byte count
if the lower 4 bits of the byte = 0x8 then add 12 to current byte count
if the lower 4 bits of the byte = 0x9 then add 13 to current byte count
if the lower 4 bits of the byte = 0xA then add 13 to current byte count
if the lower 4 bits of the byte = 0xB then add 14 to current byte count
if the lower 4 bits of the byte = 0xC then add 15 to current byte count
if the lower 4 bits of the byte = 0xD then add 15 to current byte count
if the lower 4 bits of the byte = 0xE then add 16 to current byte count
if the lower 4 bits of the byte = 0xF then add 16 to current byte count
OR
Mask off the upper nibble of the next byte. If it = 0x7 add 19 to current byte count
OR
Mask off the upper nibble of the next byte. If it = 0x9 add 14 to current byte count
OR
Mask off the upper nibble of the next byte. If it = 0xB add 7 to current byte count
OR
Mask off the upper nibble of the next byte. If it = 0x4 then Footer Found!, note the byte number and proceed to Step 5

---

4. The process is repeated at step #3 until the footer is found or we exceed 960 bytes in which case we have a problem and the following is displayed:
   Error in Determining Checksum
   The processing is aborted and the program drops back to the screen from which it was called. The user may attempt to download again.
5. We now have the starting byte number and the Footer Byte number, perform a Modulo-256 checksum up to and including the Footer Byte, compare this value against the byte found immediately after the Footer byte in the received DTA data buffer. If a mismatch between values is detected, the following is displayed:
   Checksum Error, Try Again
   The processing is aborted and the program drops back to the screen from which it was called. The user may attempt to download again.
   If the checksum was a success, the Receive From DTA Subfunction continues with the Header Block Parsing Header Block Parsing The Receive From DTA Subfunction will first parse the received Header Block:

| Byte 1  | HEADER COMMAND       |
|---------|----------------------|
| Byte 2  | MEMBER # LSB         |
| Byte 3  | MEMBER#              |
| Byte 4  | MEMBER#              |
| Byte 5  | MEMBER# MSB          |
| Byte 6  | # OF CHARACTERS IN NAME |
| Byte 7  | 222 11111            |
| Byte 8  | 4 3333 22            |
| Byte 9  | 55555 4444           |
| Byte 10 | 77 66666 5           |
| Byte 11 | 88888 777            |
| Byte 12 | AAA 99999            |
| Byte 13 | C BBBBB AA           |
| Byte 14 | DDDD CCCC            |
| Byte 15 | FF EEEEE D           |
| Byte 16 | GGGGG FFF            |
| Byte 17 | WEIGHT LSB           |
| Byte 18 | WEIGHT MSB           |
| Byte 19 | PULSE                |

The membership number in Bytes 2 to 5 is extracted and stored in a temporary variable memberno. The weight and pulse bytes are also extracted and stored in temporary variables rweight and rpulse. All other bytes in the received Header Block are ignored.

The program the searches all the client database files in the appropriate subdirectory for a record with a member_no field value matching the membership number in memberno extracted from the Header Block. When found, the client's client Workout History filename is computed and the corresponding file in the appropriate subdirectory is opened.

Exercise Block Parsing and Decoding

Following the parsing the Header Block, the Receive From DTA Subfunction will start to decode the Exercise Blocks and create complete CWH records to be appended to the file. The 20th byte in the buffer is the first exercise header command or possibly the Footer byte.

This parsing and decoding process continues until the Footer Byte is detected. When this occurs, the CWH is closed, the following is displayed and the program returns to the screen from which it was called.

DTA Data Received and Recorded

NOTE: Each new CWH record is created with the structure described earlier. The fields are empty when created with the exception of the ex_date field using the current date, the pulse field using the value from rpulse, and the weight field using the value in rweight, for each new record created and appended to the CWH file.

Weight Data Extraction and Recording

The numeric weight value embedded in the received DTA data buffer bytes 17 and 18 needs to be slightly processed before storing in the weight field of the new CWH record. Bit 7 of Byte 18 is examined. If it is set this indicates a decimal (tenths of a pound) exists the remaining numeric value represented by in Bits 6–0 of Byte 18 (MSB) and all of Byte 17 (LSB) is divided by ten and then stored in the weight field of the CWH record. If Bit 7 of Byte 18 is 0, then the number is stored as is.

Aerobic Exercise w/Embedded Exercise Name

If the lower nibble of the exercise block command byte= 0x6, the following bytes belong to an Aerobic Exercise w/Embedded Exercise Name. If the 7th byte's most significant bit (bit—7) is cleared (0) then the completed field of the new CWH record is loaded with a logical true. For all cases of the Aerobic Exercise w/Embedded Name command byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| | | |
|---|---|---|
| BYTE 1 | Exercise Group | |
| BYTE 2 | BIT 7: | Spare |
| | BIT 6: | Setting 7 1 = ALPHA 0 = NUMERIC |
| | BIT 5: | Setting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT O: | Setting 1 1 = ALPHA 0 = NUMERIC |
| BYTE 3 | BITS 7-5: | # OF SETTINGS (0–7) |
| | BITS 4-O: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Completed Status 0=completed as prescribed 1 = modified |
| BYTE 8 | BITS 7-O: | INTENSITY beats per minute (0–255) |
| BYTE 9 | BIT 7: | 1= LEVEL IS ALPHA 0=LEVEL IS NUMERIC |
| | BITS 6-O: | LEVEL (O–127 or A–Z) |
| BYTE 10 | BITS 7-5: | RATE: O=MPH 1=KPH 2=FPM 3=MPM 4=SPM |
| | BITS 4-O: | INCLINE (0–31°) |
| BYTE 11 | BIT 7 | SPEED Decimal Indicator 1= decimal point 0 = no decimal |
| | BITS 6-O | SPEED MSB |
| BYTE 12 | BITS 7-O | SPEED LSB (O–32767) or (O.O to 3276.7) |
| BYTE 13 | BITS 7-O: | CALORIES x 10 (0 TO 2550) |
| BYTE 14 | BIT 7-6: | Distance Type O=Kilometers 1=Meters 2=Miles 3=feet |
| | BIT 5 | Distance Decimal Indicator 1 = decimal present |
| | BITS 4-O | DISTANCE MSB |
| BYTE 15: | BITS 7-O: | DISTANCE LSB (0 to 8191 or 0.0 to 819.1) |
| BYTE 16 | BITS 7-O: | DURATION (0–255 mins.) |
| BYTE 17: | BITS 7-4: | Duration type 0 = seconds 1=minutes 2=hours |
| | BITS 3-O | # CHARACTERS IN EQUIPMENT NAME (1–16)+1 |
| BYTE 18 | 222 11111 | |
| BYTE 19 | 4 33333 22 | |
| BYTE 20 | 5555 4444 | |
| BYTE 21 | 77 66666 5 | |
| BYTE 22 | 88888 777 | |
| BYTE 23 | AAA 99999 | |
| BYTE 24 | C BBBBB AA | |
| BYTE 25 | DDDD CCCC | |
| BYTE 26 | FF EEEEE D | |
| BYTE 27 | GGGGG FFF | |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte Lower Nibble | ex_group |
|---|---|
| 0x6 | Aerobic |
| 0x7 | Aerobic |
| 0x8 | Anaerobic |
| 0x9 | Anaerobic |
| OxA | Stretch |
| OxB | Stretch |

Mechanical/Ergonomic Settings Related Bytes (Bytes 2–7)

If the HEADER COMMAND=0x02 (Learn Mode) then the Level settings are decoded from Bytes 3 to 7. Extract the bits as depicted earlier. If the setting is designated as alpha by looking at the corresponding bit in Byte 2, then add 0x40 to the extracted bits. The client's CWR file is examined and the exercise record corresponding to the current exercise name (or lookup number) is accessed. The seatx fields are then updated accordingly.

If the HEADER COMMAND=0x00 (Normal Mode) then Bytes 2–7 are ignored.

Intensity Setting Byte (Byte 8)

The numeric value of the intensity byte is stored in the intensity field of the new CWH record.

Level Setting Format Byte (Byte 9 Bit 7)

The level setting format is noted by the program as Bit 7 or Byte 9 set=Alpha, bit cleared=Numeric Level Setting Byte (Byte 9 Bits 6–0)

The numeric data is extracted from the byte. If the Level Setting Format designates it as a Alpha character, then the data is treated as an ASCII byte (the 8th bit is 0 anyway) and stored to the level field of the new CWH record. If the format specifies the data value as numeric, the data must be converted to characters then stored in the level field of the new CWH record.

Speed Units Code Setting Byte (Byte 10 Bits 7–5)

The Speed Units are not stored in the CWH file and thus ignored

Incline Setting Byte (Byte 10 Bits 4–0)

The incline data is extracted from Bits 4 to 0 from Byte 10 and stored directly to the incline field of the new CWH record.

Speed Decimal Indicator Byte (Byte 11 Bit 7)

The presence of a decimal point in the speed value is noted by examining Bit 7 of Byte 11. A 1=decimal point present, 0=no decimal point.

Speed Setting Bytes (Byte 11 Bits 6–0 & Byte 12)

The speed data is extracted from Byte 11 Bits 6 to 0 (MSB) and Byte 12 (LSB). If the Speed Decimal Indicator indicates a decimal point, the extracted value is divided by 10 and then stored in the speed field of the new CWH record. If there is no decimal point indicated, the extracted value is stored without dividing first.

Calories Setting Byte (Byte 13)

The calories value is extracted from Byte 13 and first multiplied by 10 before storing directly to the calories field of the new CWH record.

Distance Unit Code Setting Byte (Byte 14 Bits 7–6)

The Distance Units are not stored in the CWH file and thus ignored

Distance Decimal Indicator Byte (Byte 14 Bit 5)

The presence of a decimal point in the distance value is noted by examining Bit 5 of Byte 14. A 1=decimal point present, 0=no decimal point.

Distance Setting Bytes (Byte 14 Bits 4–0 & Byte 15)

The distance data is extracted from Byte 14 Bits 4 to 0 (MSB) and Byte 15 (LSB). If the Distance Decimal Indicator indicates a decimal point, the extracted value is divided by 10 and then stored in the distance field of the new CWH record. If there is no decimal point indicated, the extracted value is stored without dividing first.

Duration Setting Byte (Byte 16)

The duration setting is extracted from Byte 16 and stored directly to the duration field of the new CWH record.

Duration Unit Code Setting Byte (Byte 17 Bits 7–4)

The Duration Units are not stored in the CWH file and thus ignored # of Characters In Exercise Name Setting Byte (Byte 17 Bits 3–0)

The number of Characters value is used in the following section to extract the exercise name from the packed bytes.

Exercise Name Packed Bytes (Bytes 18–27)

In a similar fashion as the packing of the exercise name, the embedded exercise name characters are extracted and unpacked.

The ASCII characters have been trimmed to 5 bits before packing and thus when extracted, the upper 3 bits are restored by adding 0x40 to each extracted character.

NOTE: The ASCII space character, 0x20, is packed as 0. When an extracted 5-bit character=0, add 0x20 instead of 0x40.

The program concatenates the exercise name string one character at a time. When the number of characters equals the Number of Characters value extracted earlier, the string is stored to the exercise field of the new CWH record.

| BYTE 18 | 222 11111   | 1st Character, partial 2nd              |
|---------|-------------|-----------------------------------------|
| BYTE 19 | 4 33333 22  | remaining 2nd, complete 3rd & partial 4th |
| BYTE 20 | 5555 4444   | remaining 4th, partial 5th              |
| BYTE 21 | 77 66666 5  | remaining 5th, complete 6th, partial 7th |
| BYTE 22 | 88888 777   | remaining 7th, complete 8th             |
| BYTE 23 | AAA 99999   | complete 9th, partial 10th              |
| BYTE 24 | C BBBBB AA  | remaining 10th, complete 11th, partial 12th |
| BYTE 25 | DDDD CCCC   | remaining 12th, partial 13th            |
| BYTE 26 | FF EEEEE D  | remaining 13th, complete 14th, partial 15th |
| BYTE 27 | GGGGG FFF   | remaining 15th, complete 16th           | ex_set Field Setting

The ex_set of the new CWH record is set by extracting the value from the lower three bits of the upper nibble of the Exercise Group Byte.

Cleanup

The new CWH exercise record is now complete and appended to the CWH file. A new, blank CWH record is made with the ex_date, pulse and weight fields filled first.

Aerobic Exercise with Lookup Table Code

If the lower nibble of the exercise block command byte= 0x7 then the following bytes belong to an Aerobic Exercise with Lookup Table Code Name.

If the 7th byte's most significant bit (bit—7) is cleared (0) then the completed field of the new CWH record is loaded with a logical true.

For all cases of the Aerobic Exercise with Lookup Table Code Name command byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| BYTE 1 | Exercise Group | |
|--------|----------------|--|
| BYTE 2 | BIT 7:         | Spare |
|        | BIT 6:         | Setting 7 1 = ALPHA 0 = NUMERIC |
|        | BIT 5:         | Setting 6 1 = ALPHA 0 = NUMERIC |
|        | BIT 4:         | Setting 5 1 = ALPHA 0 = NUMERIC |
|        | BIT 3:         | Setting 4 1 = ALPHA 0 = NUMERIC |
|        | BIT 2:         | Setting 3 1 = ALPHA 0 = NUMERIC |
|        | BIT 1:         | Setting 2 1 = ALPHA 0 = NUMERIC |
|        | BIT 0:         | Setting 1 1 = ALPHA 0 = NUMERIC |
| BYTE 3 | BITS 7–5:      | # OF SETTINGS (0–7) |
|        | BITS 4–0:      | Setting #1 (0–32 or A–Z) |
| BYTE 4 | 333 22222      | Setting #2 & #3 |
| BYTE 5 | 5 44444 33     | Setting #3, #4 & #5 |
| BYTE 6 | 6666 5555      | Setting #5 & #6 |
| BYTE 7 | XX 77777 6     | Setting #6 & #7 |
|        | BIT 6:         | Spare |

-continued

|  | BIT 7: | Completed Status 0 = completed as prescribed 1 = modified |
|---|---|---|
| BYTE 8 | BITS 7–0: | INTENSITY beats per minute (0–255) |
| BYTE 9 | BIT 7: | 1 = LEVEL IS ALPHA<br>0 = LEVEL IS NUMERIC |
|  | BITS 6–0: | LEVEL (0–127 or A–Z) |
| BYTE 10 | BITS 7–5: | RATE: 0 = MPH 1 = KPH 2 = FPM<br>3 = MPM 4 = SPM |
|  | BITS 4–0: | INCLINE (0–31°) |
| BYTE 11 | BIT 7 | SPEED Decimal indicator 1= decimal point<br>0 = no decimal |
|  | BITS 6–0 | SPEED MSB |
| BYTE 12 | BITS 7–0 | SPEED LSB (0–32767) or (0.0 to 3276.7) |
| BYTE 13 | BITS 7–0: | CALORIES × 10    (0 TO 2550) |
| BYTE 14 | BIT 7–6: | Distance Type 0 = Kilometers 1 = Meters<br>2 = Miles 3 = feet |
|  | BIT 5 | Distance Decimal Indicator<br>1 = decimal present |
|  | BITS 4–0 | DISTANCE MSB |
| BYTE 15: | BJTS 7–0: | DISTANCE LSB (0 to 8191 or 0.0 to 819.1) |
| BYTE 16 | BITS 7–0: | DURATION (0–255 mins.) |
| BYTE 17: | BITS 7–4: | Duration type 0 = seconds 1 = minutes<br>2 = hours |
|  | BITS 3–0 | spare |
| BYTE 18 | Lookup Table # LSB |  |
| BYTE 19 | Lookup Table # MSB |  |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte<br>Lower Nibble | ex_group |
|---|---|
| 0 × 6 | Aerobic |
| 0 × 7 | Aerobic |
| 0 × 8 | Anaerobic |
| 0 × 9 | Anaerobic |
| 0 × A | Stretch |
| 0 × B | Stretch |

Mechanical/Ergonomic Settings Related Bytes (Bytes 2–7)

If the HEADER COMMAND=0x02 (Learn Mode) then the Level settings are decoded from Bytes 3 to 7. Extract the bits as depicted in earlier. If the setting is designated as alpha by looking at the corresponding bit in Byte 2, then add 0x40 to the extracted bits. The client's CWR file is examined and the exercise record corresponding to the current exercise name (or lookup number) is accessed. The seatx fields are then updated accordingly.

If the HEADER COMMAND=0x00 (Normal Mode) then Bytes 2–7 are ignored.

Intensity Setting Byte (Byte 8)

The numeric value of the intensity byte is stored in the intensity field of the new CWH record.

Level Setting Format Byte (Byte 9 Bit 7)

The level setting format is noted by the program as Bit 7 or Byte 9 set=Alpha, bit cleared=Numeric Level Setting Byte (Byte 9 Bits 6–0)

The numeric data is extracted from the byte. If the Level Setting Format designates it as a Alpha character, then the data is treated as an ASCII byte (the 8th bit is 0 anyway) and stored to the level field of the new CWH record. If the format specifies the data value as numeric, the data must be converted to characters then stored in the level field of the new CWH record.

Speed Units Code Setting Byte (Byte 10 Bits 7–5)

The Speed Units are not stored in the CWH file and thus ignored

Incline Setting Byte (Byte 10 Bits 4–0)

The incline data is extracted from Bits 4 to 0 from Byte 10 and stored directly to the incline field of the new CWH record.

Speed Decimal Indicator Byte (Byte 11 Bit 7)

The presence of a decimal point in the speed value is noted by examining Bit 7 of Bytel 1. A 1=decimal point present, 0=no decimal point.

Speed Setting Bytes (Byte 11 Bits 6–0 & Byte 12)

The speed data is extracted from Byte 11 Bits 6 to 0 (MSB) and Byte 12 (LSB). If the Speed Decimal Indicator indicates a decimal point, the extracted value is divided by 10 and then stored in the speed field of the new CWH record. If there is no decimal point indicated, the extracted value is stored without dividing first.

Calories Setting Byte (Byte 13)

The calories value is extracted from Byte 13 and first multiplied by 10 before storing directly to the calories field of the new CWH record.

Distance Unit Code Setting Byte (Byte 14 Bits 7–6)

The Distance Units are not stored in the CWH file and thus ignored

Distance Decimal Indicator Byte (Byte 14 Bit 5)

The presence of a decimal point in the distance value is noted by examining Bit 5 of Byte 14. A 1=decimal point present, 0=no decimal point.

Distance Setting Bytes (Byte 14 Bits 4–0 & Byte 15)

The distance data is extracted from Byte 14 Bits 4 to 0 (MSB) and Byte 15 (LSB). If the Distance Decimal Indicator indicates a decimal point, the extracted value is divided by 10 and then stored in the distance field of the new CWH record. If there is no decimal point indicated, the extracted value is stored without dividing first.

Duration Setting Byte (Byte 16)

The duration setting is extracted from Byte 16 and stored directly to the duration field of the new CWH record.

Duration Unit Code Setting Byte (Byte 17 Bits 7–4)

The Duration Units are not stored in the CWH file and thus ignored

Lookup Table # Bytes (Bytes 18–19)

The Lookup Table code value is extracted from Byte 18 (LSB) and Byte 19 (MSB). The program opens the lookups.dbf file in the appropriate subdirectory and searches the database for a match between the table_no field and the extracted lookup code value. The matching lookups.dbf record's exercise field value is then copied to the exercise field in the new CWH record. The lookups.dbf file is then closed.

ex_set Field Setting

The ex_set of the new CWH record is set by extracting the value from the lower three bits of the upper nibble of the Exercise Group Byte.

Cleanup

The new CWH exercise record is now complete and appended to the CWH file. A new, blank CWH record is made with the ex_date, pulse and weight fields filled first.

Anaerobic Exercise w/Embedded Exercise Name

If the lower nibble of the exercise block command byte= 0x8 then the following bytes belong to an Anaerobic Exercise w/Embedded Exercise Name.

If the 7th byte's most significant bit (bit—7) is cleared (0) then the completed field of the new CWH record is loaded with a logical true.

For all cases of the Aerobic Exercise w/Embedded Name command byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| BYTE 1  | Exercise Group |                                       |
|---------|----------------|---------------------------------------|
| BYTE 2  | BIT 7:         | Spare                                 |
|         | BIT 6:         | Setting 7 1 = ALPHA 0 = NUMERIC       |
|         | BIT 5:         | Setting 6 1 = ALPHA 0 = NUMERIC       |
|         | BIT 4:         | Setting 5 1 = ALPHA 0 = NUMERIC       |
|         | BIT 3:         | Setting 4 1 = ALPHA 0 = NUMERIC       |
|         | BIT 2:         | Setting 3 1 = ALPHA 0 = NUMERIC       |
|         | BIT 1:         | Setting 2 1 = ALPHA 0 = NUMERIC       |
|         | BIT 0:         | Setting 1 1 = ALPHA 0 = NUMERIC       |
| BYTE 3  | BITS 7–5:      | # OF SETTINGS (0–7)                   |
|         | BITS 4–0:      | Setting #1 (0–32 or A–Z)              |
| BYTE 4  | 333 22222      | Setting #2 & #3                       |
| BYTE 5  | 5 44444 33     | Setting #3, #4 & #5                   |
| BYTE 6  | 6666 5555      | Setting #5 & #6                       |
| BYTE 7  | XX 77777 6     | Setting #6 & #7                       |
|         | BIT 6:         | Spare                                 |
|         | BIT 7:         | Completed Status 0 = completed as prescribed 1 = modified |
| BYTE 8  | BIT 7:         | 0 = POUNDS 1 = PLATES                 |
|         | BIT 6:         | 1 = Decimal in pounds/Plate O= No decimal |
|         | BITS 5–0:      | POUNDS/PLATES MSB                     |
| BYTE 9  | BITS 7–0       | POUNDS/PLATES (0–16383 (1638.3)) LSB  |
| BYTE 10 | BITS 7–4       | Duration type 0 = seconds 1 = minutes 2 = hours |
|         | BITS 3–0       | Spare                                 |
| BYTE 11 | BITS 7–0       | DURATION (0–255)                      |
| BYTE 12 | BITS 7–0       | REPS (0–255)                          |
| BYTE 13 | BITS 7–4:      | SETS (0–15)                           |
|         | BITS 3–0       | # CHARACTERS IN EQUIPMENT NAME (1–16) +1 |
| BYTE 14 | 222 11111      |                                       |
| BYTE 15 | 4 33333 22     |                                       |
| BYTE 16 | 5555 4444      |                                       |
| BYTE 17 | 77 66666 5     |                                       |
| BYTE 18 | 88888 777      |                                       |
| BYTE 19 | AAA 99999      |                                       |
| BYTE 20 | C BBBBB AA     |                                       |
| BYTE 21 | DDDD CCCC      |                                       |
| BYTE 22 | FF EEEEE D     |                                       |
| BYTE 23 | GGGGG FFF      |                                       |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte Lower Nibble | ex_group  |
|---------------------------|-----------|
| 0x6                       | Aerobic   |
| 0x7                       | Aerobic   |
| 0x8                       | Anaerobic |
| 0x9                       | Anaerobic |
| 0xA                       | Stretch   |
| 0xB                       | Stretch   |

Mechanical/Ergonomic Settings Related Bytes (Bytes 2–7)

If the HEADER COMMAND=0x02 (Learn Mode) then the Level settings are decoded from Bytes 3 to 7. Extract the bits as depicted earlier. If the setting is designated as alpha by looking at the corresponding bit in Byte 2, then add 0x40 to the extracted bits. The client's CWR file is examined and the exercise record corresponding to the current exercise name (or lookup number) is accessed. The seatx fields are then updated accordingly.

If the HEADER COMMAND=0x0 (Normal Mode) then Bytes 2–7 are ignored.

Pounds/Plates Type Setting Byte (Byte 8 Bit 7)
The Pounds/Plates Type Setting is not stored in the CWH and thus ignored
Pounds/Plates Decimal Indicator Byte (Byte 8 Bit 6)
The presence of a decimal point in the pounds value is noted by examining Bit 6 of Byte 8. A 1=decimal point present, 0=no decimal point.
Pounds/Plates Setting Bytes (Byte 8 Bits 5–0 & Byte 9)
The pounds data is extracted from Byte 8 Bits 5 to 0 (MSB) and Byte 9 (LSB). If the Pounds/Plates Decimal Indicator indicates a decimal point, the extracted value is divided by 10 and then stored in the pounds field of the new CWH record. If there is no decimal point indicated, the extracted value is stored without dividing first.
Duration Unit Code Setting Byte (Byte 10 Bits 7–4)
The Duration Units are not stored in the CWH file and thus ignored
Duration Setting Byte (Byte 11)
The duration setting is extracted from Byte 11 and stored directly to the duration field of the new CWH record.
Repetitions Setting Byte (Byte 12)
The repetitions value is extracted from Byte 12 and stored directly to the reps field of the new CWH record.
Sets setting Byte (Byte 13 Bits 7–4)
The sets value is extracted from Byte 12 and stored directly to the reps field of the new CWH record.
of Characters In Exercise Name Setting Byte (Byte 13 Bits 3–0)
The number of Characters value is used in the following section to extract the exercise name from the packed bytes.
Exercise Name Packed Bytes (Bytes 14–23)
In a similar fashion as the packing of the exercise name, the embedded exercise name characters are extracted and unpacked.
The ASCII characters have been trimmed to 5 bits before packing and thus when extracted, the upper 3 bits are restored by adding 0x40 to each extracted character.
NOTE: The ASCII space character, 0x20, is packed as 0. When an extracted 5-bit character=0, add 0x20 instead of 0x40.
The program concatenates the exercise name string one character at a time. When the number of characters equals the Number of Characters value extracted, the string is stored to the exercise field of the new CWH record.

| BYTE 14 | 222 11111  | 1st Character, partial 2nd                 |
| BYTE 15 | 4 33333 22 | remaining 2nd, complete 3rd & partial 4th  |
| BYTE 16 | 5555 4444  | remaining 4th, partial 5th                 |
| BYTE 17 | 77 66666 5 | remaining 5th, complete 6th, partial 7th   |
| BYTE 18 | 88888 777  | remaining 7th, complete 8th                |
| BYTE 19 | AAA 99999  | complete 9th, partial 10th                 |
| BYTE 20 | C BBBBB AA | remaining 10th, complete 11th, partial 12th|
| BYTE 21 | DDDD CCCC  | remaining 12th, partial 13th               |
| BYTE 22 | FF EEEEE D | remaining 13th, complete 14th, partial 15th|
| BYTE 23 | GGGGG FFF  | remaining 15th, complete 16th              | ex_set Field Setting
The ex_set of the new CWH record is set by extracting the value from the lower three bits of the upper nibble of the Exercise Group Byte.
Cleanup
The new CWH exercise record is now complete and appended to the CWH file. A new, blank CWH record is made with the ex_date, pulse and weight fields filled first.
Anaerobic Exercise with Lookup Table Code Exercise Name
If the lower nibble of the exercise block command byte= 0x9 then the following bytes belong to an Anaerobic Exercise with Lookup Table Code Exercise Name If the 7th byte's most significant bit (bit—7) is cleared (0) then the completed field of the new CWH record is loaded with a logical true.

For all cases of the Aerobic Exercise with Lookup Table Code Exercise Name command byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| BYTE 1 | Exercise Group | |
|---|---|---|
| BYTE 2 | BIT 7: | Spare |
| | BIT 6: | Setting 7 1 = ALPHA 0 = NUMERIC |
| | BIT 5: | Seyting 6 1 = ALPHA 0 = NUMERIC |
| | BIT 4: | Setting 5 1 = ALPHA 0 = NUMERIC |
| | BIT 3: | Setting 4 1 = ALPHA 0 = NUMERIC |
| | BIT 2: | Setting 3 1 = ALPHA 0 = NUMERIC |
| | BIT 1: | Setting 2 1 = ALPHA 0 = NUMERIC |
| | BIT 0: | Setting 1 1 = ALPHA 0 = NUMERIC |
| BYTE 3 | BITS 7–5: | # OF SETTINGS (0–7) |
| | BITS 4–0: | Setting #1 (0–32 or A–Z) |
| BYTE 4 | 333 22222 | Setting #2 & #3 |
| BYTE 5 | 5 44444 33 | Setting #3, #4 & #5 |
| BYTE 6 | 6666 5555 | Setting #5 & #6 |
| BYTE 7 | XX 77777 6 | Setting #6 & #7 |
| | BIT 6: | Spare |
| | BIT 7: | Completed Status 0 = completed as prescribed 1 = modified |
| BYTE 8 | BIT 7: | 0 = POUNDS 1 = PLATES |
| | BIT 6: | 1 = Decimal in pounds/Plate 0 = No decimal |
| | BITS 5–0: | POUNDS/PLATES MSB |
| BYTE 9 | BITS 7–0 | POUNDS/PLATES (0–16383 (1638.3)) LSB |
| BYTE 10 | BITS7–0 | REPS (0–255) |
| BYTE 11 | BITS 7–4: | SETS (0–15) |
| | BITS 3–0 | Duration type 0 = seconds 1 = minutes 2 = hours |
| BYTE 12 | BITS 7–0 | DURATION (0–255) |
| BYTE 13 | LOOKUP TABLE # LSB | |
| BYTE 14 | LOOKUP TABLE # MSB | |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte Lower Nibble | ex_group |
|---|---|
| 0 × 6 | Aerobic |
| 0 × 7 | Aerobic |
| 0 × 8 | Anaerobic |
| 0 × 9 | Anaerobic |
| 0 × A | Stretch |
| 0 × B | Stretch |

Mechanical/Ergonomic Settings Related Bytes (Bytes 2–7)
These bytes are not stored in the CWH and thus ignored.
Pounds/Plates Type Setting Byte (Byte 8 Bit 7)
The Pounds/Plates Type Setting is not stored in the CWH and thus ignored
Pounds/Plates Decimal Indicator Byte (Byte 8 Bit 6)

The presence of a decimal point in the pounds value is noted by examining Bit 6 of Byte 8. A 1=decimal point present, 0=no decimal point.
Pounds/Plates Setting Bytes (Byte 8 Bits 5–0 & Byte 9)

The pounds data is extracted from Byte 8 Bits 5 to 0 (MSB) and Byte 9 (LSB). If the Pounds/Plates Decimal Indicator indicates a decimal point, the extracted value is divided by 10 and then stored in the pounds field of the new CWH record. If there is no decimal point indicated, the extracted value is stored without dividing first.
Repetitions Setting Byte (Byte 10)

The repetitions value is extracted from Byte 10 and stored directly to the reps field of the new CWH record.
Sets setting Byte (Byte 1 Bits 7–4)

The sets value is extracted from Byte 11 Bits 7 to 4 and stored directly to the sets field of the new CWH record.
Duration Unit Code Setting Byte (Byte 11 Bits 3–0)
The Duration Units are not stored in the CWH file and thus ignored
Duration Setting Byte (Byte 12)

The duration setting is extracted from Byte 11 and stored directly to the duration field of the new CWH record.
Lookup Table # Bytes (Bytes 13–14)

The Lookup Table code value is extracted from Byte 13 (LSB) and Byte 14 (MSB).The program opens the lookups-.dbf file in the appropriate subdirectory and searches the database for a match between the table_no field and the extracted lookup code value. The matching lookups.dbf record's exercise field value is then copied to the exercise field in the new CWH record. The lookups.dbf file is then closed.
ex_set Field Setting The ex_set of the new CWH record is set by extracting the value from the lower three bits of the upper nibble of the Exercise Group Byte.
Cleanup The new CWH exercise record is now complete and appended to the CWH file. A new, blank CWH record is made with the ex_date, pulse and weight fields filled first.
Stretch Exercise w/Embedded Exercise Name If the lower nibble of the exercise block command byte= 0xA then the following bytes belong to an Stretch Exercise w/Embedded Exercise Name.

If the 3rd byte's least significant bit (bit 0) is cleared (0) then the completed field of the new CWH record is loaded with a logical true.

For all cases of the Stretch Exercise w/Embedded Name command byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| BYTE 1 | Exercise Group | |
|---|---|---|
| BYTE 2 | BITS 7–0: | DURATION (0–255) |
| BYTE 3 | BITS 7–4: | Duration type 0 = seconds 1 =minutes 2=hours |
| | BITS 3–1: | Spare |
| | BIT 0: | Completed Status 0 = completed as prescribed 1 = modified |
| BYTE 4 | BIT 7–0: | REPS (0–255) |
| BYTE 5 | BITS 7–4: | SETS (0–15) |
| | BITS 3–0 | # CHARACTERS IN EQUIPMENT NAME (1–16) +1 |
| BYTE 6 | 222 11111 | a |
| BYTE 7 | 4 33333 22 | b |
| BYTE 8 | 5555 4444 | c |
| BYTE 9 | 77 66666 5 | d |
| BYTE 10 | 88888 777 | e |
| BYTE 11 | AAA 99999 | a |
| BYTE 12 | C BBBBB AA | b |

-continued

| BYTE 13 | DDDD CCCC | c |
| BYTE 14 | FF EEEEE D | d |
| BYTE 15 | GGGGG FFF | e |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte Lower Nibble | ex_group |
| --- | --- |
| 0 × 6 | Aerobic |
| 0 × 7 | Aerobic |
| 0 × 8 | Anaerobic |
| 0 × 9 | Anaerobic |
| 0 × A | Stretch |
| 0 × B | Stretch |

Duration Setting Byte (Byte 2)

The duration setting is extracted from Byte 2 and stored directly to the duration field of the new CWH record.

Duration Unit Code Setting Byte (Byte 3 Bits 7–4)

The Duration Units are not stored in the CWH file and thus ignored

Repetitions Setting Byte (Byte 4)

The repetitions value is extracted from Byte 4 and stored directly to the reps field of the new CWH record.

Sets setting Byte (Byte 5 Bits 7–4)

The sets value is extracted from Byte 5 Bits 7 to 4 and stored directly to the sets field of the new CWH record.

of Characters In Exercise Name Setting Byte (Byte 5 Bits 3–0)

The number of Characters value is used in the following section to extract the exercise name from the packed bytes.

Exercise Name Packed Bytes (Bytes 6–15)

In a similar fashion as the packing of the exercise name, the embedded exercise name characters are extracted and unpacked.

The ASCII characters have been trimmed to 5 bits before packing and thus when extracted, the upper 3 bits are restored by adding 0x40 to each extracted character.

NOTE: The ASCII space character, 0x20, is packed as 0. When an extracted 5-bit character=0, add 0x20 instead of 0x40.

The program concatenates the exercise name string one character at a time. When the number of characters equals the Number of Characters value extracted, the string is stored to the exercise field of the new CWH record.

| BYTE 6 | 222 11111 | 1st Character, partial 2nd |
| BYTE 7 | 4 33333 22 | remaining 2nd, complete 3rd & partial 4th |
| BYTE 8 | 5555 4444 | remaining 4th, partial 5th |
| BYTE 9 | 77 66666 5 | remaining 5th, complete 6th, partial 7th |
| BYTE 10 | 88888 777 | remaining 7th, complete 8th |
| BYTE 11 | AAA 99999 | complete 9th, partial 10th |
| BYTE 12 | C BBBBB AA | remaining 10th, complete 11th, partial 12th |
| BYTE 13 | DDDD CCCC | remaining 12th, partial 13th |
| BYTE 14 | FF EEEEE D | remaining 13th, complete 14th, partial 15th |
| BYTE 15 | GGGGG FFF | remaining 15th, complete 16th | ex_set field Setting

The ex_set of the new CWH record is set by extracting the value from the lower three bits of the upper nibble of the Exercise Group Byte.

Cleanup

The new CWH exercise record is now complete and appended to the CWH file. A new, blank CWH record is made with the ex_date, pulse and weight fields filled first.

Stretch Exercise with Lookup Table Code Exercise Name

If the lower nibble of the exercise block command byte= 0xB then the following bytes belong to an Stretch Exercise with Lookup Table Code Exercise Name.

If the 3rd byte's least significant bit (bit 0) is cleared (0) then the completed field of the new CWH record is loaded with a logical true.

For all cases of the Stretch Exercise with Lookup Table Code Exercise Name exercise group byte, the following extraction and recording procedure is performed.

NOTE: The following procedure description refers to specific byte numbers. For clarification, the bytes in the described exercise block start with the arbitrary number 1. The actual byte number in the Received DTA Data Package Buffer will depend upon its actual position amongst the other exercise blocks.

| BYTE 1 | Exercise Group | |
| BYTE 2 | BITS 7–0: | DURATION (0–255) |
| BYTE 3 | BITS 7–4: | Duration type 0 = seconds 1 = minutes 2 = hours |
| | BITS 3–1: | Spare |
| | BIT 0: | Completed Status 0 = completed as prescribed 1 = modified |
| BYTE 4 | BIT 7–0: | REPS (0–255) |
| BYTE 5 | BITS 7–4: | SETS (0–15) |
| | BITS 3–0 | spare |
| BYTE 6 | Lookup Table # LSB | |
| BYTE 7 | Lookup Table # MSB | |

Exercise Group Byte (Byte 1)

The Exercise Group byte is decoded to determine what exercise group the block represents. The lower nibble is used to determine the exercise group. The resultant decoded value is stored to the ex_group field of the new CWH record as follows:

| Command Byte Lower Nibble | ex_group |
| --- | --- |
| 0 × 6 | Aerobic |
| 0 × 7 | Aerobic |
| 0 × 8 | Anaerobic |
| 0 × 9 | Anaerobic |
| 0 × A | Stretch |
| 0 × B | Stretch |

Duration Setting Byte (Byte 2)

The duration setting is extracted from Byte 2 and stored directly to the duration field of the new CWH record.

Duration Unit Code Sting Byte (Byte 3 Bits 7–4)

The Duration Units are not stored in the CWH file and thus ignored

Repetitions Setting Byte (Byte 4)

The repetitions value is extracted from Byte 4 and stored directly to the reps field of the new CWH record.

Sets setting Byte (Byte 5 Bits 7–4)

The sets value is extracted from Byte 5 Bits 7 to 4 and stored directly to the sets field of the new CWH record.

Lookup Table # Bytes (Bytes 6–7)

The Lookup Table code value is extracted from Byte 6 (LSB) and Byte 7 (MSB). The program opens the lookups.dbf file in the appropriate subdirectory and searches the database for a match between the table_no field and the extracted lookup code value. The matching lookups.dbf record's exercise field value is then copied to the exercise field in the new CWH record. The lookups.dbf file is then closed.

ex_set Field Setting

The ex_set of the new CWH record is set by extracting the value from the lower three bits of the upper nibble of the Exercise Group Byte.

Cleanup

The new CWH exercise record is now complete and appended to the CWH file. A new, blank CWH record is made with the ex_date, pulse and weight fields filled first.

I claim:

1. An exercise guidance system for guiding an individual through a workout schedule using an adaptive workout routine that includes a series of selected exercises and a progressive series of intermediate performance goals for each of the exercises, each of the progressive series of intermediate performance goals being calculated, for each exercise, based upon the individual's current performance of the exercise, a previous intermediate performance goal for the exercise and a selected final performance goal for the exercise using a preselected, but variable, set of calculation parameters, said system comprising:

a portable data recorder/display unit having
 data input means for manually entering data into said portable data recorder/display unit representative of an individual's current performance of an exercise,
 recorder memory means capable of storing data for later retrieval,
 display means capable for displaying data,
 input/output port means for communicating data between said recorder memory means and an external device, and
 data controller means for storing in and retrieving from said recorder memory means data entered from the data input means and displaying from said recorder memory means selected data on said display means, said controller means also capable of sending data stored in said recorder memory means to, and receiving data from, said external device through said input/output port means; and a separate base programming unit having
 processing means, external from said portable data recorder/display unit, having memory means containing a control program and stored data representing, for each of the exercises to be performed by the individual, and individual's current performance of the exercise, a preselected initial intermediate performance goal and a final performance goal, a preselected plurality of calculation parameters, said processing means calculating a subsequent intermediate performance goal using said individual's current performance of the exercise, a previous intermediate performance goal for the exercise and said final performance goal for the exercise using said plurality of calculation parameters, wherein said processing means communicating said subsequent performance goal to said portable data recorder/display unit for display thereon for guidance of the individual in performing the exercise for each exercise to be performed by the individual, and
 a docking station unit adapted to mate electrically with said input/output port means of said portable data recorder/display unit for communicating data between said portable data recorder/display unit and said processing means of said base programming unit.

2. The exercise guidance system as in claim 1 wherein said base programming unit further comprises:
 data input means for manually entering modified data representing said initial and said subsequent intermediate performance and said final performance goals and said plurality of calculation parameters in said memory means of said processing means.

3. The exercise guidance system as in claim 1 wherein said base programming unit further comprises:
 display means capable of visually displaying selected data from said memory means.

4. The exercise guidance system as in claim 1 wherein said programming unit further comprises:
 docking station unit having a shape adapted to receive and retain releasably said portable data recorder/display unit.

5. The exercise guidance system as in claim 1 wherein said base programming unit further comprises:
 connection means for connecting said processing means of said base programming unit to said docking station unit for communicating data therebetween.

6. The exercise guidance system as in claim 5 wherein said connection means comprises a cable means.

7. The exercise guidance system as in claim 1 wherein said memory means of said processing means of said base programming unit is further operable for storing an historical database of data representative of said individual's current performance of the exercise for evaluation with respect to some further exercise activity.

8. The exercise guidance system as in claim 1 wherein said processing means of said base programming unit includes a programmed microcomputer.

9. The exercise guidance system as in claim 1 wherein said display means of said portable data recorder/display unit includes an alphanumeric display means.

10. The exercise guidance system as in claim 9 wherein said alphanumeric display means comprises a liquid crystal display.

11. The exercise guidance system as in claim 10 wherein said memory means of said processing means of said base programming unit is further operable for storing an historical database of data representative of said individual's current performance of the exercise for evaluation with respect to some further exercise activity.

12. The exercise guidance system as in claim 10 wherein said processing means of said base programming unit includes a programmed microcomputer.

13. The exercise guidance system as in claim 10 wherein said controller means of said portable data recorder/display unit is adapted to store and retrieve separately data entered by a plurality of individuals.

14. The exercise guidance system as in claim 10 wherein said processing means of said base programming unit and stored data in said memory means of said processing means are adapted to calculate subsequent intermediate performance goals for a plurality of individuals.

15. The exercise guidance system as in claim 10 wherein said processing means of said base programming unit and stored data in said memory means of said processing means are adapted to calculate subsequent intermediate performance goals for a plurality of exercises.

16. The exercise guidance system as in claim 1 wherein said controller means of said portable data recorder/display unit is adapted to store and retrieve separately data entered by a plurality of individuals.

17. The exercise guidance system as in claim 1 wherein said processing means of said base programming unit and stored data in said memory means of said processing means are adapted to calculate subsequent intermediate performance goals for a plurality of individuals.

18. The exercise guidance system as in claim 1 wherein said processing means of said base programming unit and stored data in said memory means of said processing means are adapted to calculate subsequent intermediate performance goals for a plurality of exercises.

19. An exercise guidance system for guiding an individual through a workout schedule using an adaptive workout routine that includes a series of selected exercises and a progressive series of intermediate performance goals for each of the exercises, each of the progressive series of intermediate performance goals being calculated, for each exercise, based upon the individual's current performance of the exercise, a previous intermediate performance goal for the exercise and a selected final performance goal for the exercise using a preselected, but variable, set of calculation parameters, said system comprising:

a portable data recorder/display unit having data input means for manually entering data into said portable data recorder/display unit representative of an individual's current performance of an exercise, recorder memory means capable of storing data for later retrieval, display means capable for displaying data, input/output port means for communicating data between said recorder memory means and an external device, and data controller means for storing in and retrieving from said recorder memory means data entered from the data input means and displaying from said recorder memory means selected data on said display means, said controller means also capable of sending data stored in said recorder memory means to, and receiving data from, said external device through said input/output port means; and a separate base programming unit having processing means, external from said portable data recorder/display unit, having memory means containing a control program and stored data representing, for each of the exercises to be performed by the individual, and individual's current performance of the exercise, a preselected initial intermediate performance goal and a final performance goal, a preselected plurality of calculation parameters, said processing means calculating a subsequent intermediate performance goal using said individual's current performance of the exercise, a previous intermediate performance goal for the exercise and said final performance goal for the exercise using said plurality of calculation parameters, wherein said processing means communicating said subsequent performance goal to said portable data recorder/display unit for display thereon for guidance of the individual in performing the exercise for each exercise to be performed by the individual, data input means for manually entering modified data representing said initial and said subsequent intermediate performance and said final performance goals and said plurality of calculation parameters in said memory means of said processing means;

display means capable of visually displaying selected data from said memory means; and a docking station unit adapted to mate electrically with said input/output port means of said portable data recorder/display unit for communicating data between said portable data recorder/display unit and said processing means of said base programming unit, and having a shape adapted to receive and retain releasably said portable data recorder/display unit.

20. The exercise guidance system as in claim 19 wherein said base programming unit further comprises:

connection means for connecting said processing means of said base programming unit to said docking station unit for communicating data therebetween.

21. The exercise guidance system as in claim 20 wherein said connection means comprises a cable means.

22. The exercise guidance system as in claim 20 wherein said display means of said portable data recorder/display unit includes an alphanumeric display means.

23. The exercise guidance system as in claim 22 wherein said alphanumeric display means comprises a liquid crystal display.

\* \* \* \* \*